United States Patent
Witschel et al.

(10) Patent No.: US 12,133,529 B2
(45) Date of Patent: Nov. 5, 2024

(54) HERBICIDAL PHENYLETHERS

(71) Applicant: BASF SE, Ludwigshafen (DE)

(72) Inventors: Matthias Witschel, Ludwigshafen (DE); Laetitia Souillart, Wuppertal (DE); Tobias Seiser, Ludwigshafen (DE); Trevor William Newton, Limburgerhof (DE); Liliana Parra Rapado, Limburgerhof (DE); Dario Massa, Limburgerhof (DE); Raphael Aponte, Mannheim (DE); Thomas Mietzner, Annweiler (DE); Thomas Seitz, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 18/140,395

(22) Filed: Apr. 27, 2023

(65) Prior Publication Data
US 2023/0345941 A1    Nov. 2, 2023

Related U.S. Application Data

(63) Continuation of application No. 16/765,526, filed as application No. PCT/EP2018/080856 on Nov. 12, 2018, now abandoned.

(30) Foreign Application Priority Data

Nov. 23, 2017    (EP) .................................... 17203283

(51) Int. Cl.
| | |
|---|---|
| *A01N 43/54* | (2006.01) |
| *A01N 25/04* | (2006.01) |
| *A01N 25/08* | (2006.01) |
| *A01N 43/40* | (2006.01) |
| *A01N 43/56* | (2006.01) |
| *A01N 43/58* | (2006.01) |
| *A01N 43/653* | (2006.01) |
| *A01N 43/66* | (2006.01) |
| *A01N 43/90* | (2006.01) |

(52) U.S. Cl.
CPC ............. *A01N 43/54* (2013.01); *A01N 25/04* (2013.01); *A01N 25/08* (2013.01); *A01N 43/40* (2013.01); *A01N 43/56* (2013.01); *A01N 43/58* (2013.01); *A01N 43/653* (2013.01); *A01N 43/66* (2013.01); *A01N 43/90* (2013.01)

(58) Field of Classification Search
CPC ........ A01N 43/54; A01N 25/04; A01N 25/08; A01N 43/40; A01N 43/56; A01N 43/58; A01N 43/653; A01N 43/66; A01N 43/90
See application file for complete search history.

(56) References Cited

U.S. PATENT DOCUMENTS

| | | | |
|---|---|---|---|
| 5,486,521 A | 1/1996 | Brouwer et al. | |
| 5,527,764 A | 6/1996 | Dao-cong et al. | |
| 6,121,201 A | 9/2000 | Pulman et al. | |
| 6,992,044 B1 | 1/2006 | Andree et al. | |

FOREIGN PATENT DOCUMENTS

| | | |
|---|---|---|
| EP | 1106607 A2 | 6/2001 |
| EP | 1122244 B1 | 9/2004 |
| JP | 2001-270867 A | 10/2001 |
| WO | WO-98/41093 A1 | 9/1998 |
| WO | WO-02/098227 A1 | 12/2002 |
| WO | WO-03/029255 A1 | 4/2003 |
| WO | WO-2017/102275 A1 | 6/2017 |
| WO | WO-2017/198859 A1 | 11/2017 |
| WO | WO-2017/202768 A1 | 11/2017 |
| WO | WO-2017/207358 A1 | 12/2017 |
| WO | WO-2018/015180 A1 | 1/2018 |
| WO | WO-2018/019552 A1 | 2/2018 |
| WO | WO-2018/019554 A1 | 2/2018 |
| WO | WO-2018/019555 A1 | 2/2018 |
| WO | WO-2018/019574 A1 | 2/2018 |
| WO | WO-2018/019721 A1 | 2/2018 |
| WO | WO-2018/019755 A1 | 2/2018 |
| WO | WO-2018/019758 A1 | 2/2018 |
| WO | WO-2018/019765 A1 | 2/2018 |
| WO | WO-2018/019767 A1 | 2/2018 |
| WO | WO-2018/019770 A1 | 2/2018 |
| WO | WO-2018/019842 A1 | 2/2018 |
| WO | WO-2018/019845 A1 | 2/2018 |
| WO | WO-2018/019860 A1 | 2/2018 |
| WO | WO-2018/024695 A1 | 2/2018 |
| WO | WO-2018/024696 A1 | 2/2018 |
| WO | WO-2018/029029 A1 | 2/2018 |

(Continued)

OTHER PUBLICATIONS

International Application No. PCT/EP2018/080856, International Search Report and Written Opinion, mailed Jan. 16, 2019.

(Continued)

*Primary Examiner* — Mina Haghighatian
*Assistant Examiner* — Nathan W Schlientz
(74) *Attorney, Agent, or Firm* — ArentFox Schiff LLP

(57) ABSTRACT

The present invention relates to phenylethers of formula (I)

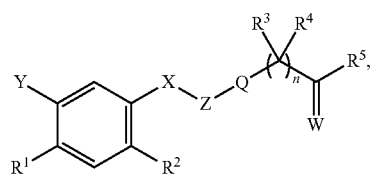

or their agriculturally acceptable salts or derivatives, wherein the variables are defined according to the description, processes and intermediates for preparing the phenylethers of formula (I), compositions comprising them and their use as herbicides, i.e. for controlling harmful plants, and also a method for controlling unwanted vegetation which comprises allowing a herbicidal effective amount of at least one phenylether of formula (I) to act on plants, their seed and/or their habitat.

10 Claims, No Drawings

(56) References Cited

FOREIGN PATENT DOCUMENTS

| WO | WO-2018/029030 A1 | 2/2018 |
|----|-------------------|--------|
| WO | WO-2018/029031 A1 | 2/2018 |
| WO | WO-2018/095811 A1 | 5/2018 |
| WO | WO-2018/108612 A1 | 6/2018 |
| WO | WO-2018/108695 A1 | 6/2018 |
| WO | WO-2018/114759 A1 | 6/2018 |
| WO | WO-2018/141594 A1 | 8/2018 |
| WO | WO-2018/166822 A1 | 9/2018 |
| WO | WO-2018/178039 A1 | 10/2018 |
| WO | WO-2018/219935 A1 | 12/2018 |
| WO | WO-2018/219936 A1 | 12/2018 |
| WO | WO-2018/229041 A1 | 12/2018 |
| WO | WO-2018/234371 A1 | 12/2018 |
| WO | WO-2018/235005 A1 | 12/2018 |
| WO | WO-2019/016385 A1 | 1/2019 |
| WO | WO-2019/101513 A1 | 5/2019 |
| WO | WO-2019/101560 A1 | 5/2019 |
| WO | WO-2019101551 A1 | 5/2019 |

OTHER PUBLICATIONS

European Search Report for EP Patent Application No. 17203283.1, Issued on Feb. 5, 2018, 4 pages.

HERBICIDAL PHENYLETHERS

CROSS-REFERENCE TO RELATED APPLICATIONS

This is a continuation of U.S. patent application Ser. No. 16/765,526, which is the U.S. national phase of International Application No. PCT/EP2018/080856, filed Nov. 12, 2018, which claims the benefit of European Application No. 17203283.1, filed Nov. 23, 2017.

The present invention relates to phenylethers of the general formula (I) defined below and to their use as herbicides. Moreover, the invention relates to compositions for crop protection and to a method for controlling unwanted vegetation.

WO 02/098227, EP1 106 607 and EP 1 122 244 describe structurally similar compounds, whereas the compounds according to the invention are characterized by a different heterocycle Y.

However, the herbicidal properties of these known compounds regarding the harmful plants are not always entirely satisfactory.

It is therefore an object of the present invention to provide phenylethers of formula (I) having improved herbicidal action. To be provided are in particular phenylethers of formula (I) which have high herbicidal activity, in particular even at low application rates, and which are sufficiently compatible with crop plants for commercial utilization.

These and further objects are achieved by the phenylethers of formula (I), defined below, and by their agriculturally suitable salts.

Accordingly, the present invention provides phenylethers of formula (I)

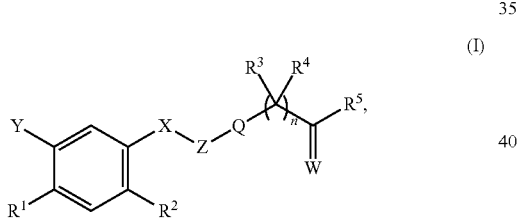

(I)

wherein the substituents have the following meanings:
$R^1$ H or halogen;
$R^2$ H, halogen, CN, $NO_2$, $NH_2$, $CF_3$ or C(=S)$NH_2$;
$R^3$ H, halogen, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, ($C_1$-$C_3$-alkyl)amino, di($C_1$-$C_3$-alkyl)amino, $C_1$-$C_3$-alkoxy-$C_1$-$C_3$-alkyl, $C_1$-$C_3$-alkoxycarbonyl;
$R^4$ H, halogen, $C_1$-$C_3$-alkyl, $C_1$-$C_3$-alkoxy;
$R^5$ $OR^6$, $SR^6$, $NR^7R^8$, $NR^6OR^6$, $NR^6S(O)_2R^7$ or $NR^6S(O)_2NR^7R^8$, wherein
  $R^6$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
  —N=$CR^9R^{10}$, wherein $R^9$ and $R^{10}$ independently of one another are H, $C_1$-$C_4$-alkyl or phenyl;
  $C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6- membered heteroaryl,
    wherein each cycloalkyl, heterocyclyl, phenyl or heteroaryl ring can be substituted by one to four substituents selected from $R^{13}$ or a 3- to 7-membered carbocycle,
    which carbocycle optionally has in addition to carbon atoms one or two ring members selected from the group consisting of
      —N($R^9$)—, —N=N—, —C(=O)—, —O— and —S—, and
    which carbocycle is optionally substituted with one to four substituents selected from $R^{11}$;
    wherein $R^{11}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
$R^7$, $R^8$ independently of one another are $R^6$, or together form a 3- to 7-membered carbocycle,
  which carbocycle optionally has in addition to carbon atoms one or two ring members selected from the group consisting of —N($R^9$)—, —N=N—, —C(=O)—, —O— and —S—, and
  which carbocycle is optionally substituted with one to four substituents selected from $R^{11}$;
n 1 to 3;
Q O, S, SO, $SO_2$, NH or ($C_1$-$C_3$-alkyl)N;
W O or S;
X O or S;
Y is a heterocycle selected from the group consisting of $Y^1$ to $Y^{73}$

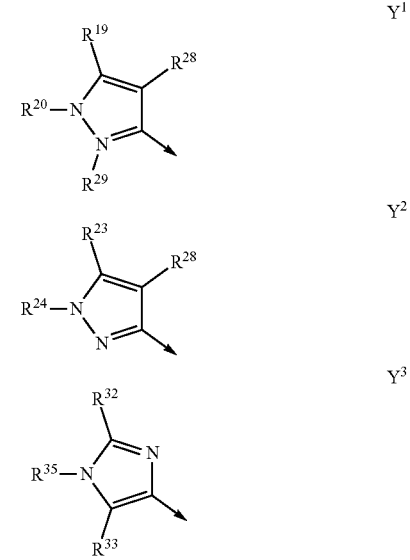

| | |
|---|---|
| (structure) | $Y^4$ |
| (structure) | $Y^5$ |
| (structure) | $Y^6$ |
| (structure) | $Y^7$ |
| (structure) | $Y^8$ |
| (structure) | $Y^9$ |
| (structure) | $Y^{10}$ |
| (structure) | $Y^{11}$ |
| (structure) | $Y^{12}$ |
| (structure) | $Y^{13}$ |
| (structure) | $Y^{14}$ |
| (structure) | $Y^{15}$ |
| (structure) | $Y^{16}$ |
| (structure) | $Y^{17}$ |
| (structure) | $Y^{18}$ |
| (structure) | $Y^{19}$ |
| (structure) | $Y^{20}$ |
| (structure) | $Y^{21}$ |

-continued
Y²²
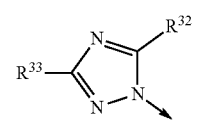
Y²³
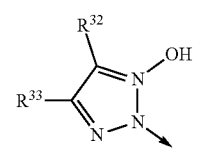
Y²⁴
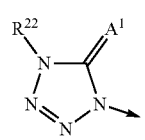
Y²⁵
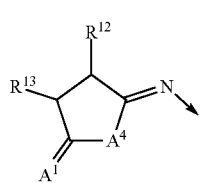
Y²⁶
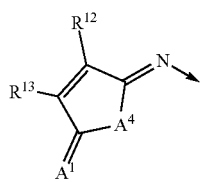
Y²⁷
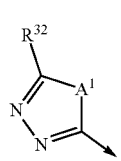
Y²⁸
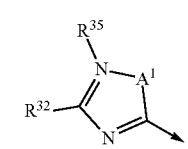
Y²⁹
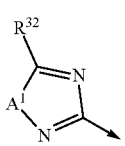
Y³⁰
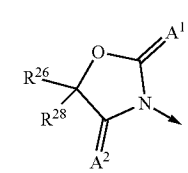
Y³¹
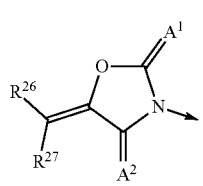
-continued
Y³²
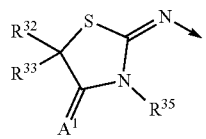
Y³³
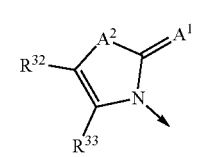
Y³⁴
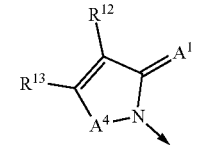
Y³⁵
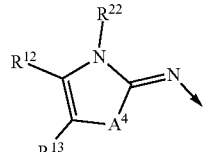
Y³⁶
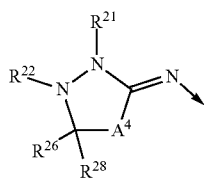
Y³⁷
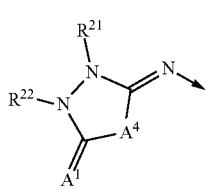
Y³⁸
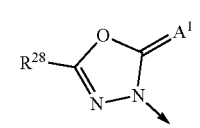
Y³⁹
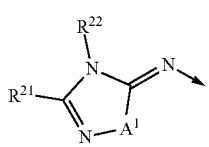
Y⁴⁰
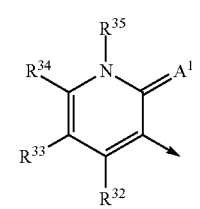

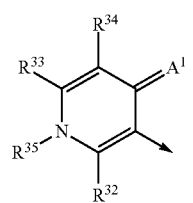
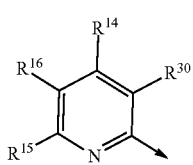
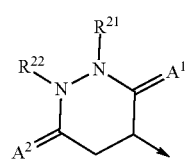
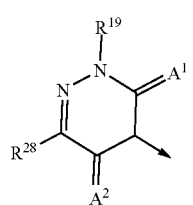
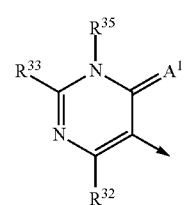
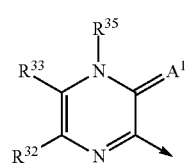
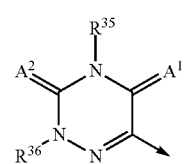
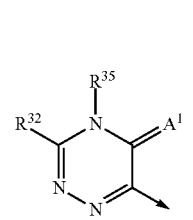
$Y^{41}$
$Y^{42}$
$Y^{43}$
$Y^{44}$
$Y^{45}$
$Y^{46}$
$Y^{47}$
$Y^{48}$
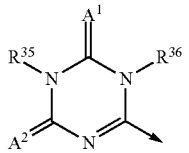
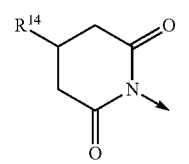
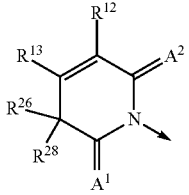
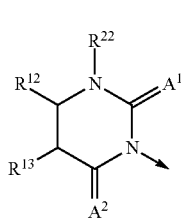
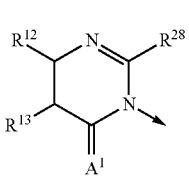
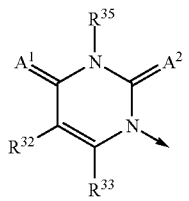
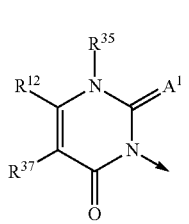
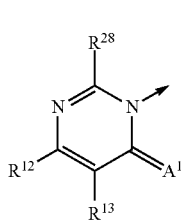
$Y^{49}$
$Y^{50}$
$Y^{51}$
$Y^{52}$
$Y^{53}$
$Y^{54}$
$Y^{55}$
$Y^{56}$ -continued
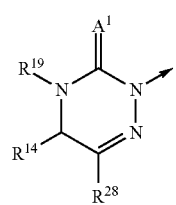 $Y^{57}$
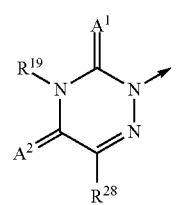 $Y^{58}$
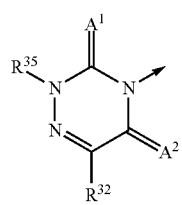 $Y^{59}$
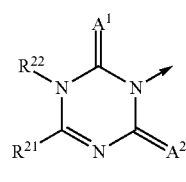 $Y^{60}$
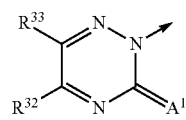 $Y^{61}$
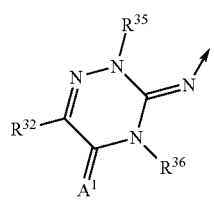 $Y^{62}$
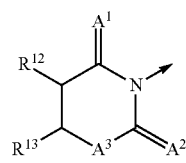 $Y^{63}$
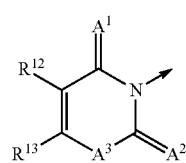 $Y^{64}$
-continued
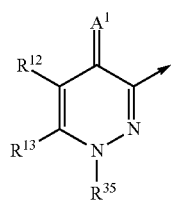 $Y^{65}$
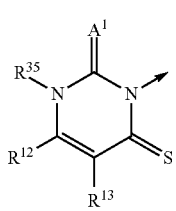 $Y^{66}$
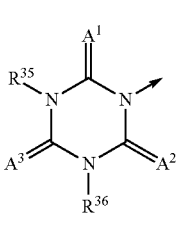 $Y^{67}$
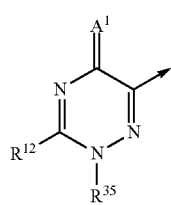 $Y^{68}$
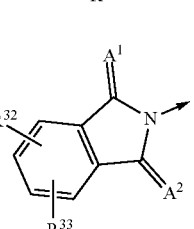 $Y^{69}$
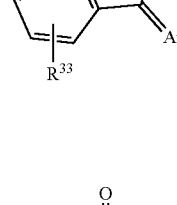
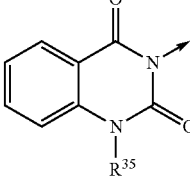 $Y^{70}$
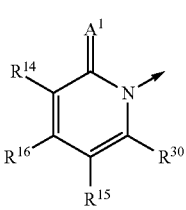 $Y^{71}$ -continued

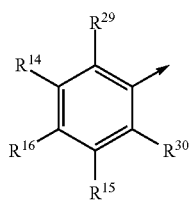
Y⁷²

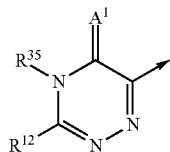
Y⁷³ wherein
$A^1$, $A^2$, $A^3$ are oxygen or sulfur;
$A^4$ is oxygen, sulphur, SO or $SO_2$;
$R^{12}$, $R^{13}$, $R^{14}$, $R^{15}$, $R^{16}$, $R^{17}$ and $R^{18}$
  are hydrogen, hydroxy, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkenyloxy, $C_3$-$C_6$-alkynyl, $C_3$-$C_6$-alkynyloxy, $C_1$-$C_6$-alkylthio, $C_1$-$C_6$-alkylsulfinyl, $C_1$-$C_6$-alkylsulfonyl, $C_1$-$C_6$-alkoxysulfonyl, $C_1$-$C_6$-alkylsulfonyloxy, amino, $C_1$-$C_6$-alkylamino or di($C_1$-$C_6$-alkyl)amino; or
$R^{12}$ and $R^{13}$ together with the atoms to which they are attached, form a three- to six-membered cycle, which is saturated, partial unsaturated or aromatic, which may comprise apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, and which for its part may be partially or fully halogenated and/or substituted by one to three radicals from the group consisting of $C_1$-$C_6$-alkyl and $C_1$-$C_6$-alkoxy;
$R^{19}$, $R^{20}$, $R^{21}$, $R^{22}$, $R^{23}$, $R^{24}$ are hydrogen, cyano, hydroxy, $C_1$-$C_6$-alkyl, $C_1$-$C_6$-cyanoalkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkenyloxy, $C_3$-$C_6$-alkynyl, $C_3$-$C_6$-alkynyloxy, $C_1$-$C_6$-alkylsulfinyl, $C_1$-$C_6$-alkylsulfonyl, phenyl-$C_1$-$C_6$-alkyl, amino, $C_1$-$C_6$-alkylamino or di($C_1$-$C_6$-alkyl)amino; or
$R^{21}$ and $R^{22}$ together with the atoms to which they are attached, form a three- to six-membered cycle, which is saturated, partial unsaturated or aromatic, which may comprise apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, and which for its part may be partially or fully halogenated and/or substituted by one to three radicals from the group consisting of $C_1$-$C_6$-alkyl and $C_1$-$C_6$-alkoxy;
$R^{25}$ is hydrogen, $C_1$-$C_6$-alkyl, $C_1$-$C_6$-haloalkyl, $C_2$-$C_6$-alkenyl, $C_3$-$C_6$-alkynyl, $C_1$-$C_6$-haloalkoxy, amino, $C_1$-$C_6$-alkylamino or di($C_1$-$C_6$-alkyl)amino;

$R^{26}$ and $R^{27}$
  are hydrogen, halogen or $C_1$-$C_6$-alkyl;
$R^{28}$, $R^{29}$ and $R^{30}$
  are hydrogen, halogen, hydroxy, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkenyloxy, $C_3$-$C_6$-alkynyl or $C_3$-$C_6$-alkynyloxy; and
$R^{31}$ is hydrogen, $NH_2$, $C_1$-$C_6$-alkyl or $C_3$-$C_6$-alkynyl;
$R^{32}$, $R^{33}$ and $R^{34}$
  are hydrogen, amino, nitro, cyano, carboxy, carbamoyl, thiocarmbamoyl, halogen, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkenyloxy, $C_3$-$C_6$-alkynyl, $C_3$-$C_6$-alkynyloxy, $C_1$-$C_6$-alkoxycarbonyl, $C_2$-$C_6$-alkenylthio, $C_3$-$C_6$-alkynylthio, $C_1$-$C_6$-alkylamino, di($C_1$-$C_6$-alkyl)amino or $C_3$-$C_7$-cycloalkyl-$C_1$-$C_3$-alkyl;
$R^{35}$ and $R^{36}$
  are hydrogen, cyano, hydroxyl, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_2$-$C_6$-alkenyl, $C_3$-$C_6$-alkynyl, $C_1$-$C_6$-alkoxycarbonyl, amino, $C_1$-$C_6$-alkylamino, di($C_1$-$C_6$-alkyl)amino, $C_3$-$C_7$-cycloalkyl-$C_1$-$C_3$-alkyl, phenyl or phenyl-$C_1$-$C_6$-alkyl;
$R^{37}$ halogen or $C_1$-$C_6$-alkyl;
Z phenyl, pyridyl, pyridazinyl, pyrimidinyl or pyrazinyl,
  each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy;
including their agriculturally acceptable salts or derivatives, provided the compounds of formula (I) have a carboxyl group.

The present invention also provides agrochemical compositions comprising at least one phenylether of formula (I) and auxiliaries customary for formulating crop protection agents.

The present invention also provides herbicidal compositions comprising at least one phenylether of formula (I) (component A) and at least one further compound selected from the herbicidal compounds B (component B) and safeners C (component C).

The present invention also provides the use of phenylethers of formula (I) as herbicides, i.e. for controlling harmful plants.

The present invention furthermore provides a method for controlling unwanted vegetation where a herbicidal effective amount of at least one phenylethers of the formula (I) is allowed to act on plants, their seeds and/or their habitat. Application can be done before, during and/or after, preferably during and/or after, the emergence of the undesirable plants.

Moreover, the invention relates to processes and intermediates for preparing phenylethers of formula (I).

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the phenylethers of formula (I), the herbicidal compounds B and/or the safeners C as described herein are capable of forming geometrical isomers, for example E/Z isomers, it is possible to use both, the pure isomers and mixtures thereof, in the compositions according to the invention.

If the phenylethers of formula (I), the herbicidal compounds B and/or the safeners C as described herein have one or more centres of chirality and, as a consequence, are present as enantiomers or diastereomers, it is possible to use both, the pure enantiomers and diastereomers and their mixtures, in the compositions according to the invention.

If the phenylethers of formula (I), the herbicidal compounds B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diethylammonium, diisopropylammonium, trimethylammonium, triethylammonium, tris(isopropyl)ammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Phenylethers of formula (I), herbicidal compounds B and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides.

Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The organic moieties mentioned in the definition of the variables $R^3$ to $R^{37}$ and $R^a$ to $R^e$ are—like the term halogen—collective terms for individual enumerations of the individual group members.

The term halogen denotes in each case fluorine, chlorine, bromine or iodine. All hydrocarbon chains, e.g. all alkyl, alkenyl, alkynyl, alkoxy chains, can be straight-chain or branched, the prefix $C_n$-$C_m$ denoting in each case the possible number of carbon atoms in the group.

Examples of such meanings are:

$C_1$-$C_3$-alkyl and also the $C_1$-$C_3$-alkyl moieties of di($C_1$-$C_3$-alkyl)amino, $C_1$-$C_3$-alkoxy-$C_1$-$C_3$-alkyl: for example $CH_3$, $C_2H_5$, n-propyl and $CH(CH_3)_2$;

$C_1$-$C_4$-alkyl and also the $C_1$-$C_4$-alkyl moieties of phenyl-$C_1$-$C_4$-alkyl: for example $CH_3$, $C_2H_5$, n-propyl, $CH(CH_3)_2$, n-butyl, $CH(CH_3)$—$C_2H_5$, $CH_2$—CH$(CH_3)_2$ and $C(CH_3)_3$;

$C_1$-$C_6$-alkyl and also the $C_1$-$C_6$-alkyl moieties of $C_1$-$C_6$-cyanoalkyl, $C_1$-$C_6$-alkyoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl, $C_3$-$C_6$-cycloalkyl-$C_1$-$C_6$-alkyl, $C_3$-$C_6$-heterocyclyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_3$-haloalkyl: $C_1$-$C_3$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl;

$C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-alkenyl and also the $C_3$-$C_6$-alkenyl moieties of $C_3$-$C_6$-alkenyloxy-$C_1$-$C_6$-alkyl, $C_3$-$C_6$-alkenyloxy-$C_1$-$C_6$-alkoxy-$C_1$-$C_6$-alkyl, $C_3$-$C_6$-alkenyloxycarbonyl-$C_1$-$C_6$-alkyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl and also the $C_3$-$C_6$-haloalkenyl moieties of $C_3$-$C_6$-haloalkenyloxy-$C_1$-$C_6$-alkyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl and also the $C_3$-$C_6$-alkynyl moieties of $C_3$-$C_6$-alkynyloxycarbonyl-$C_1$-$C_6$-alkyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_3$-alkoxy and also the $C_1$-$C_3$-alkoxy moieties of $C_1$-$C_3$-alkoxy-$C_1$-$C_3$-alkyl, $C_1$-$C_3$-alkoxycarbonyl: for example methoxy, ethoxy, propoxy;

$C_1$-$C_4$-alkoxy and also the $C_1$-$C_4$-alkoxy moieties of $C_1$-$C_4$-alkoxycarbonyl: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkyoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_3$-$C_6$-alkenyloxy-$C_1$-$C_6$-alkoxy-$C_1$-$C_6$-alkyl, $C_1$-$C_6$-alkoxycarbonyl-$C_1$-$C_6$-alkyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_1$-$C_3$-haloalkoxy: a $C_1$-$C_3$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromo-methyl)-2-bromoethoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromo-methyl)-2-bromoethoxy, 4-fluorobutoxy, 4-chlorobutoxy, 4-bromobutoxy and nonafluorobutoxy;

$C_1$-$C_6$-haloalkoxy and also the $C_1$-$C_6$-haloalkoxy moieties of $C_1$-$C_6$-haloalkoxy-$C_1$-$C_6$-alkyl, $C_1$-$C_6$-haloalkoxycarbonyl-$C_1$-$C_6$-alkyl: a $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_3$-alkylthio: for example methylthio, ethylthio, propylthio, 1-methylethylthio;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio and also the $C_1$-$C_6$-alkylthio moieties of $C_1$-$C_6$-alkylthio-$C_1$-$C_6$-alkyl: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—) and also the $C_1$-$C_6$-alkylsulfinyl moieties of $C_1$-$C_6$-alkylsulfinyl-$C_1$-$C_6$-alkyl: for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—) and also the $C_1$-$C_6$-alkylsulfonyl moieties of $C_1$-$C_6$-alkylsulfonyl-$C_1$-$C_6$-alkyl: for example methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

($C_1$-$C_3$-alkyl)amino: for example methylamino, ethylamino, propylamino, 1-methylethyl-amino;

($C_1$-$C_4$-alkyl)amino: for example methylamino, ethylamino, propylamino, 1-methylethyl-amino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1- methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methyl-pentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_3$-$C_6$-cycloalkyl and also the cycloalkyl moieties of $C_1$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

$C_3$-$C_6$-heterocyclyl and also the heterocyclyl moieties of $C_3$-$C_6$-heterocyclyl-$C_1$-$C_6$-alkyl: aliphatic heterocycle having 3 to 6 ring members which, in addition to carbon atoms, contains 1 to 4 nitrogen atoms, or 1 to 3 nitrogen atoms and an oxygen or sulphur atom, or an oxygen or a sulphur atom, for example three- or four-membered heterocycles like 2-oxetanyl, 3-oxetanyl, 2-thietanyl, 3-thietanyl, 1-azetidinyl, 2-azetidinyl, 1-azetinyl, 2-azetinyl; five-membered saturated heterocycles like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4-thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, 1,3,4-triazolidin-2-yl; six-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydopyranyl, 4-tetrahydropyranyl, 2-tetrahydrothiopyranyl, 3-tetrahydrothiopyranyl, 4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, 2-morpholinyl, 3-morpholinyl;

5- or 6 membered heteroaryl: aromatic heteroaryl having 5 or 6 ring members which, in addition to carbon atoms, contains 1 to 4 nitrogen atoms, or 1 to 3 nitrogen atoms and an oxygen or sulphur atom, or an oxygen or a sulphur atom, for example 5-membered aromatic rings like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl); 1-tetrazolyl; 6-membered aromatic rings like pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl);

3- to 7-membered carbocycle: a three- to seven-membered monocyclic, saturated, partial unsaturated or aromatic cycle having three to seven ring members which comprises apart from carbon atoms optionally one or two ring members selected from the group consisting of —N($R^{12}$)—, —N=N—, —C(=O)—, —O— and —S—.

The preferred embodiments of the invention mentioned herein below have to be understood as being preferred either independently from each other or in combination with one another.

According to a preferred embodiment of the invention preference is also given to those phenylethers of formula (I), wherein the variables, either independently of one another or in combination with one another, have the following meanings:

Preferred are the phenylethers of formula (I) wherein $R^1$ is H, F or Cl;
  particularly preferred is H or F;
  especially preferred is H;
  also particularly preferred is H or Cl;
  especially preferred is Cl;
  also particularly preferred is F or Cl;
  especially preferred is F.

Also preferred are the phenylethers of formula (I) wherein $R^2$ is halogen or CN;
  preferably F, Cl, Br or CN;
  particularly preferred is F, Cl or CN;
  especially preferred is Cl or CN;
  more preferred is Cl;
  also more preferred is CN;
  also especially preferred is F or Cl;
  more preferred is F.

Also preferred are the phenylethers of formula (I) wherein $R^3$ is H, $C_1$-$C_3$-alkyl, $C_1$-$C_3$-haloalkyl, $C_1$-$C_3$-alkoxy, $C_1$-$C_3$-haloalkoxy or $C_1$-$C_3$-alkylthio;

particularly preferred is H, $C_1$-$C_3$-alkyl, $C_1$-$C_3$-haloalkyl or $C_1$-$C_3$-alkoxy;
  especially preferred is H, $C_1$-$C_3$-alkyl or $C_1$-$C_3$-alkoxy;
  more preferred is H, $CH_3$ or $OCH_3$.
Also preferred are the phenylethers of formula (I) wherein $R^4$ is H, halogen or $C_1$-$C_3$-alkyl;
  particularly preferred is H, F or $CH_3$;
  especially preferred is H.
Also preferred are the phenylethers of formula (I) wherein $R^5$ is $OR^6$, $SR^6$, $NR^7R^8$, $NR^6S(O)_2R^7$ or $NR^6S(O)_2NR^7R^8$;
  particularly preferred is $OR^6$, $NR^7R^8$, $NR^6S(O)_2R^7$ or $NR^6S(O)_2NR^7R^8$;
  especially preferred $OR^6$, $NR^6S(O)_2R^7$ or $NR^6S(O)_2NR^7R^8$;
  especially preferred is $OR^6$ or $NR^6S(O)_2R^7$.
Also preferred are the phenylethers of formula (I) wherein $R^6$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxy-carbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
  —N=$CR^9R^{10}$,
    wherein $R^9$ and $R^{10}$ independently of one another are H, $C_1$-$C_4$-alkyl or phenyl;
  $C_3$-$C_6$-cycloalkyl, $C_3$-$C_6$-cycloalkyl-$C_1$-$C_6$-alkyl, $C_3$-$C_6$-heterocyclyl, phenyl, phenyl-$C_1$-$C_4$-alkyl or a 5- or 6 membered heteroaryl,
    wherein each cycloalkyl, heterocyclyl, phenyl or heteroaryl ring can be substituted by one to four substituents selected from $R^{11}$ or a 3- to 7-membered carbocycle,
      which carbocycle optionally has in addition to carbon atoms one or two ring members selected from the group consisting of —N($R^9$)—, —N=N—, —C(=O)—, —O— and —S—, and
      which carbocycle is optionally substituted with one to four substituents selected from $R^{11}$, wherein $R^{11}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
    preferably is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
    particularly preferred is hydrogen, $C_1$-$C_6$-alkyl, $C_3$-$C_6$-alkenyl, $C_3$-$C_6$-alkynyl or $C_1$-$C_6$-haloalkyl;
    especially preferred is hydrogen, $C_1$-$C_6$-alkyl, or $C_3$-$C_6$-alkynyl;
    more preferred is hydrogen, $CH_3$, $C_2H_5$ or $CH_2C\equiv CH$.

Also preferred are the phenylethers of formula (I) wherein $R^7$ is H or $C_1$-$C_6$-alkyl;
  more preferred is H;
  also more preferred is $C_1$-$C_6$-alkyl.
Also preferred are the phenylethers of formula (I) wherein $R^8$ is H or $C_1$-$C_6$-alkyl;
  more preferred is H;
  also more preferred is $C_1$-$C_6$-alkyl.
Also preferred are the phenylethers of formula (I) wherein $R^9$ is phenyl or $C_1$-$C_4$-alkyl;
  particularly preferred is phenyl or $CH_3$;
  also particularly preferred is phenyl;
  also particularly preferred is $C_1$-$C_4$-alkyl.
Also preferred are the phenylethers of formula (I) wherein $R^{10}$ is phenyl or $C_1$-$C_4$-alkyl;
  particularly preferred is phenyl or $CH_3$;
  also particularly preferred is phenyl;
  also particularly preferred is $C_1$-$C_4$-alkyl.
Also preferred are the phenylethers of formula (I) wherein $R^{11}$ is halogen or $C_1$-$C_6$-alkyl;
  particularly preferred is F, Cl or $CH_3$;
  also particularly preferred is halogen;
  especially preferred is F or Cl;
  also particularly preferred is $C_1$-$C_6$-alkyl;
  especially preferred is $CH_3$.
Also preferred are the phenylethers of formula (I) wherein n is 1 or 2;
  particularly preferred is 2;
  also particularly preferred is 1.
Also preferred are the phenylethers of formula (I) wherein Q is O or S;
  particularly preferred is O.
Also preferred are the phenylethers of formula (I) wherein W is O,
  also preferably is S.
Also preferred are the phenylethers of formula (I) wherein X is O,
  also preferably is S.
According to a preferred embodiment of the invention preference is also given to those phenylethers of formula (I), wherein the variables, either independently of one another or in combination with one another, have the following meanings:
  Y is preferably $Y^2$, $Y^{13}$, $Y^{20}$, $Y^{31}$, $Y^{37}$, $Y^{38}$, $Y^{39}$, $Y^{42}$, $Y^{48}$, $Y^{55}$, $Y^{65}$, $Y^{66}$, $Y^{67}$ or $Y^{68}$;
    is particularly preferred $Y^2$, $Y^{20}$, $Y^{26}$, $Y^{31}$, $Y^{37}$, $Y^{38}$, $Y^{42}$, $Y^{48}$, $Y^{55}$, $Y^{65}$, $Y^{66}$, $Y^{67}$ or $Y^{68}$;
    is especially preferred $Y^2$, $Y^{20}$, $Y^{26}$, $Y^{37}$, $Y^{42}$, $Y^{55}$, $Y^{65}$, $Y^{66}$ or $Y^{67}$;
    is more preferred $Y^2$, $Y^{20}$, $Y^{55}$, $Y^{65}$ or $Y^{67}$;
  $A^1$ and $A^2$ preferably are oxygen;
    also preferably are sulphur;
  $A^3$ preferably is oxygen,
    also more preferably is sulphur;
  $A^4$ preferably is oxygen,
    also preferably is sulphur;
  $R^{12}$, $R^{13}$, $R^{14}$, $R^{15}$, $R^{16}$, $R^{17}$ and $R^{18}$
    preferably are H, $C_1$-$C_6$-alkyl, $C_1$-$C_6$-haloalkyl, $C_1$-$C_6$-alkylthio, $C_1$-$C_6$-alkylsulfonyl,
    or
    $R^{12}$ and $R^{13}$ together with the atoms to which they are attached, form a five- to six-membered cycle,
      which is saturated, partial unsaturated or aromatic,
      which may comprise apart from carbon atoms one to four nitrogen atoms, or one oxygen atoms, or one sulfur atoms, and which for its part may be partially or fully halogenated and/or substituted by one to three $C_1$-$C_6$-alkyl groups;
particularly preferred are preferably are H, $C_1$-$C_6$-alkyl, $C_1$-$C_6$-haloalkyl,
or
$R^{12}$ and $R^{13}$ together with the atoms to which they are attached, form a six-membered cycle, which is saturated,
especially preferred are H, $C_1$-$C_6$-alkyl, $C_1$-$C_6$-haloalkyl;
more preferred are H, $CH_3$ or $CF_3$;
$R^{16}$ and $R^{11}$ are most preferably $C_1$-$C_6$-haloalkyl;
$R^{18}$ is most preferably $CH_3$;
$R^{19}$, $R^{20}$, $R^{21}$, $R^{22}$, $R^{23}$ and $R^{24}$
preferably are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfinyl, $C_1$-$C_6$-alkylsulfonyl,
or
$R^{21}$ and $R^{22}$ together with the atoms to which they are attached, form a five- to six-membered cycle,
which is saturated, partial unsaturated or aromatic,
which may comprise apart from carbon atoms one to four nitrogen atoms, or one or two oxygen atoms, or one or two sulfur atoms, and
which for its part may be partially or fully halogenated and/or substituted by one or more $C_1$-$C_6$-alkyl groups;
particularly preferred are hydrogen, halogen, $C_1$-$C_6$-alkyl, $C_1$-$C_6$-haloalkyl or $C_1$-$C_6$-haloalkoxy,
or
$R^{21}$ and $R^{22}$ together with the atoms to which they are attached, form a five- to six-membered cycle,
which is saturated, and
which for its part may be partially or fully halogenated and/or substituted by one or more $C_1$-$C_6$-alkyl groups;
especially preferred are $C_1$-$C_6$-alkyl, $C_1$-$C_6$-haloalkyl or $C_1$-$C_6$-haloalkoxy,
or
$R^{21}$ and $R^{22}$ together with the atoms to which they are attached, form six-membered cycle, which is saturated;
more preferred are $CH_3$, $CF_3$, $CF_2H$ or $OCF_2H$;
$R^{25}$ is preferably $C_1$-$C_6$-alkyl or $C_1$-$C_6$-haloalkyl;
$R^{26}$ and $R^{27}$
preferably are hydrogen, halogen or $C_1$-$C_6$-alkyl;
particularly preferred are $C_1$-$C_6$-alkyl;
$R^{28}$, $R^{29}$ and $R^{30}$
preferably are hydrogen, halogen or $C_1$-$C_6$-alkyl;
more preferably are halogen or $C_1$-$C_6$-alkyl;
most preferably are halogen;
also most preferably are $C_1$-$C_6$-alkyl;
also most preferably are hydrogen;
$R^{31}$ preferably is $C_1$-$C_6$-alkyl;
$R^{32}$, $R^{33}$ and $R^{34}$
preferably are hydrogen, halogen, $C_1$-$C_6$-alkyl or $C_1$-$C_6$-haloalkyl;
particularly preferred are $C_1$-$C_6$-haloalkyl;
$R^{35}$ and $R^{36}$ preferably are hydrogen, amino, $C_1$-$C_6$-alkyl or $C_1$-$C_6$-haloalkyl;
particularly preferred are $C_1$-$C_6$-alkyl;
$R^{37}$ preferably is Cl or $CH_3$;
particularly preferred is $CH_3$.

Also preferred are the phenylethers of formula (I) wherein Z is phenyl or pyridyl,
each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
preferably is phenyl,
which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
also preferably is pyridyl,
which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy.
Also preferred are the phenylethers of formula (I) wherein Z is phenyl or pyridyl,
each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
preferably is phenyl or pyridyl,
each of which is optionally substituted by 1 to 4 substituents selected from the group consisting of halogen, $C_1$-$C_6$-alkyl, $C_1$-$C_6$-haloalkyl, $C_1$-$C_6$-alkoxy or $C_1$-$C_6$-haloalkoxy;
particularly preferred is phenyl or pyridyl,
each of which is optionally substituted by 1 to 4 substituents selected from the group consisting of halogen or $C_1$-$C_6$-alkyl;
especially preferred is phenyl or pyridyl,
each of which is optionally substituted by 1 to 4 substituents selected from the group consisting of F, Cl or $CH_3$;
more preferred is phenyl or pyridyl,
each of which is unsubstituted.
Also preferred are the phenylethers of formula (I) wherein Z is phenyl,
which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
preferably is phenyl,
which is optionally substituted by 1 to 4 substituents selected from the group consisting of halogen, $C_1$-$C_6$-alkyl, $C_1$-$C_6$-haloalkyl, $C_1$-$C_6$-alkoxy or $C_1$-$C_6$-haloalkoxy;
particularly preferred is phenyl,
which is optionally substituted by 1 to 4 substituents selected from the group consisting of halogen or $C_1$-$C_6$-alkyl;
especially preferred is phenyl,
which is optionally substituted by 1 to 4 substituents selected from the group consisting of F, Cl or $CH_3$;
more preferred is unsubstituted phenyl.
Also preferred are the phenylethers of formula (I) wherein Z is pyridyl,
which is optionally substituted by 1 to 3 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
preferably is pyridyl,
which is optionally substituted by 1 to 3 substituents selected from the group consisting of halogen, $C_1$-$C_6$-alkyl, $C_1$-$C_6$-haloalkyl, $C_1$-$C_6$-alkoxy or $C_1$-$C_6$-haloalkoxy;
particularly preferred is pyridyl, which is optionally substituted by 1 to 3 substituents selected from the group consisting of halogen or $C_1$-$C_6$-alkyl;

especially preferred is pyridyl,
which is optionally substituted by 1 to 3 substituents selected from the group consisting of F, Cl or $CH_3$;
more preferred is unsubstituted.

Also preferred are the phenylethers of formula (I) wherein Z is selected from the group consisting of $Z^1$ to $Z^{29}$ Z-1
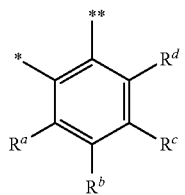

Z-2
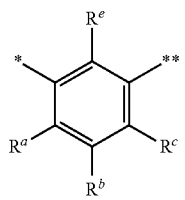

Z-3
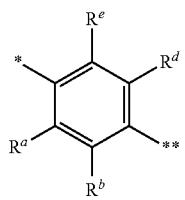

Z-4
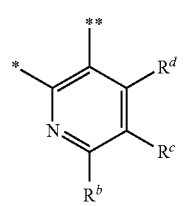

Z-5
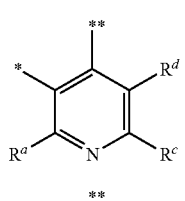

Z-6
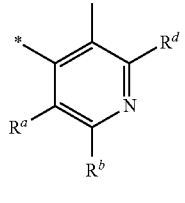

Z-7
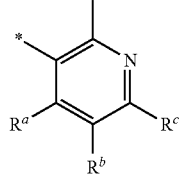

Z-8
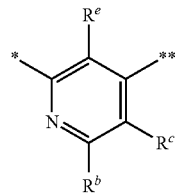

Z-9
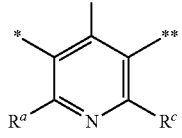

Z-10
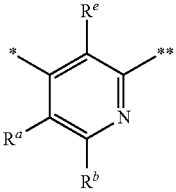

Z-11
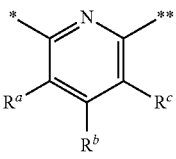

Z-12
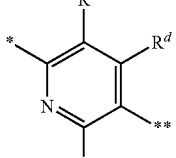

Z-13
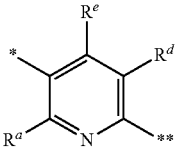

Z-14
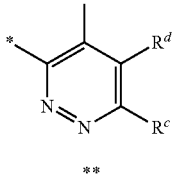

Z-15
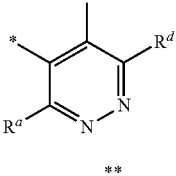

Z-16
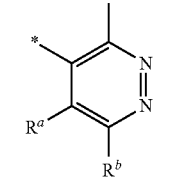

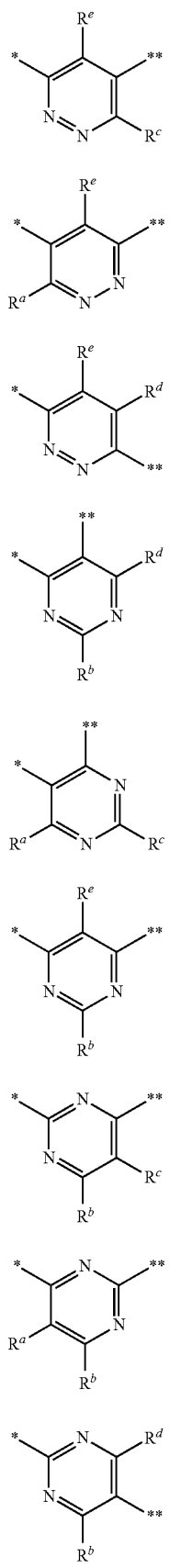

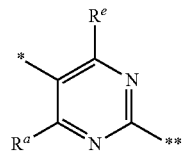

wherein
* denotes the point of attachment of Z to X;
* denotes the point of attachment of Z to Q; and
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H.

Also preferred are the phenylethers of formula (I) wherein Z is selected from the group consisting of $Z^1$, $Z^2$, $Z^3$, $Z^4$, $Z^5$, $Z^6$, $Z^7$, $Z^8$, $Z^9$, $Z^{10}$, $Z^{11}$, $Z^{12}$, $Z^{13}$ and $Z^{21}$ as defined above;
particularly preferred is selected from the group consisting of $Z^1$, $Z^2$, $Z^4$, $Z^5$, $Z^6$, $Z^7$, $Z^8$, $Z^9$, $Z^{10}$, $Z^{11}$ and $Z^{21}$ as defined above;
especially preferred is selected from the group consisting of $Z^1$, $Z^4$, $Z^5$, $Z^6$ and $Z^7$ as defined above;
more preferred is selected from the group consisting of $Z^1$ and $Z^7$ as defined above.

Also preferred are the phenylethers of formula (I) wherein Z is selected from the group consisting of $Z^1$, $Z^2$, $Z^3$, $Z^4$, $Z^5$, $Z^6$, $Z^7$, $Z^8$, $Z^9$, $Z^{10}$, $Z^{11}$, $Z^{12}$, $Z^{13}$ and $Z^{21}$ as defined above; wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;
particularly preferred is selected from the group consisting of $Z^1$, $Z^2$, $Z^4$, $Z^5$, $Z^6$, $Z^7$, $Z^8$, $Z^9$, $Z^{10}$, $Z^{11}$ and $Z^{21}$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;

especially preferred is selected from the group consisting of $Z^1$, $Z^4$, $Z^5$, $Z^6$ and $Z^7$ as defined above, wherein
$R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;

more preferred is selected from the group consisting of $Z^1$ and $Z^7$ as defined above, wherein
$R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H.

Also preferred are the phenylethers of formula (I) wherein $R^1$ is H or F, and
$R^2$ is F, Cl or CN.

Also preferred are the phenylethers of formula (I) wherein $R^3$ is H, $C_1$-$C_3$-alkyl or $C_1$-$C_3$-alkoxy, and
$R^4$ is H.

Also preferred are the phenylethers of formula (I) wherein $R^5$ is $OR^6$, $NR^6S(O)_2R^7$ or $NR^6S(O)_2NR^7R^8$, wherein
$R^6$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl; and
$R^7$, $R^8$ are $C_1$-$C_6$-alkyl.

Also preferred are the phenylethers of formula (I) wherein n is 1.

Also preferred are the phenylethers of formula (I) wherein Q, W and X are O.

Also preferred are the phenylethers of formula (I) wherein
$R^1$ is H or halogen;
$R^2$ is halogen or CN;
$R^3$ is H, $C_1$-$C_3$-alkyl, $C_1$-$C_3$-haloalkyl, $C_1$-$C_3$-alkoxy, $C_1$-$C_3$-haloalkoxy or $C_1$-$C_3$-alkylthio;
$R^4$ is H;
$R^5$ is $OR^6$, $SR^6$, $NR^7R^8$, $NR^6S(O)_2R^7$ or $NR^6S(O)_2NR^7R^8$; wherein
$R^6$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)amino-carbonyl-$C_1$-$C_6$-alkyl, di($C_1$-$C_6$-alkyl)aminocarbonyl-$C_1$-$C_6$-alkyl,
—N=$CR^9R^{10}$,
wherein $R^9$ and $R^{10}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, phenyl, phenyl-$C_1$-$C_4$-alkyl or a 5- or 6 membered heteroaryl,
wherein each cycloalkyl, heterocyclyl, phenyl or heteroaryl ring can be substituted by one to four substituents selected from $R^{11}$ or a 3- to 7-membered carbocycle,
which carbocycle optionally has in addition to carbon atoms one or two ring members selected from the group consisting of —N($R^{11}$)—, —N=N—, —C(=O)—, —O— and —S—, and
which carbocycle is optionally substituted with one to four substituents selected from $R^{11}$;
$R^7$ is $C_1$-$C_6$-alkyl;
$R^8$ is H or $C_1$-$C_6$-alkyl;
$R^9$ is phenyl or $CH_3$;
$R^{10}$ is phenyl or $CH_3$;
$R^{11}$ is halogen or $C_1$-$C_6$-alkyl;
n is 1 or 2;
Q is O, S, SO, $SO_2$, NH or ($C_1$-$C_3$-alkyl)N;
W is O;
X is O;
Z $Z^1$, $Z^2$, $Z^3$, $Z^4$, $Z^5$, $Z^6$, $Z^7$, $Z^8$, $Z^9$, $Z^{10}$, $Z^{11}$, $Z^{12}$, $Z^{13}$ and $Z^{21}$ as defined above, wherein
$R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
particularly preferred are the phenylethers of formula (I) wherein
$R^1$ is H or halogen;
$R^2$ is halogen or CN;
$R^3$ is H, $C_1$-$C_3$-alkyl, $C_1$-$C_3$-haloalkyl or $C_1$-$C_3$-alkoxy;
$R^4$ is H;
$R^5$ $OR^6$, $NR^7R^8$, $NR^6S(O)_2R^7$ or $NR^6S(O)_2NR^7R^8$; wherein
$R^6$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
$R^7$ is $C_1$-$C_6$-alkyl;
$R^8$ is H or $C_1$-$C_6$-alkyl;
n is 1;
Q is O, S, SO, $SO_2$, NH or ($C_1$-$C_3$-alkyl)N;
W is O;
X is O;
Z is selected from the group consisting of $Z^1$, $Z^2$, $Z^4$, $Z^5$, $Z^6$, $Z^7$, $Z^8$, $Z^9$, $Z^{10}$, $Z^{11}$ and $Z^{21}$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
especially preferred are the phenylethers of formula (I) wherein
$R^1$ is H, F or Cl;
$R^2$ is F, Cl or CN;
$R^3$ is H, $C_1$-$C_3$-alkyl or $C_1$-$C_3$-alkoxy;

$R^4$ is H;
$R^5$ is $OR^6$ or $NR^6S(O)_2R^7$, wherein
  $R^6$ is hydrogen, $C_1$-$C_6$-alkyl, $C_3$-$C_6$-alkenyl, $C_3$-$C_6$-alkynyl or $C_1$-$C_6$-haloalkyl, and
  $R^7$ is $C_1$-$C_6$-alkyl;
n is 1;
Q is O or S;
W is O;
X is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
more preferred are the phenylethers of formula (I) wherein
$R^1$ is H, F or Cl;
$R^2$ is F, Cl or CN;
$R^3$ is H, $CH_3$ or $OCH_3$;
$R^4$ is H;
$R^5$ is $OR^6$ or $NR^6S(O)_2R^7$; wherein
  $R^6$ is hydrogen, $C_1$-$C_6$-alkyl, or $C_3$-$C_6$-alkynyl, and
  $R^7$ is $C_1$-$C_6$-alkyl;
n is 1;
Q is O;
W is O;
X is O;
Z is selected from the group consisting of $Z^1$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy.
Also preferred are the phenylethers of formula (I) wherein
$R^1$ is H, F or Cl;
$R^2$ is F, C or CN;
$R^3$ is H, $CH_3$ or $OCH_3$;
$R^4$ is H;
$R^5$ $OR^6$, $SR^6$, $NR^7R^8$, $NR^6OR^6$, $NR^6S(O)_2R^7$ or $NR^6S(O)_2NR^7R^8$, wherein
  $R^6$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl. $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
  —N=$CR^9R^{10}$, wherein $R^9$ and $R^{10}$ independently of one another are H, $C_1$-$C_4$-alkyl or phenyl;
  $C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6 membered heteroaryl,
  wherein each cycloalkyl, heterocyclyl, phenyl or heteroaryl ring can be substituted by one to four substituents selected from $R^{14}$ or a 3- to 7-membered carbocycle,
  which carbocycle optionally has in addition to carbon atoms one or two ring members selected from the group consisting of
  —N($R^9$)—, —N=N—, —C(=O)—, —O— and —S—, and
  which carbocycle is optionally substituted with one to four substituents selected from $R^{11}$;
  wherein $R^{11}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
$R^7$, $R^8$ independently of one another are $R^9$, or together form a 3- to 7-membered carbocycle,
  which carbocycle optionally has in addition to carbon atoms one or two ring members selected from the group consisting of —N($R^{10}$)—, —N=N—, —C(=O)—, —O— and —S—, and
  which carbocycle is optionally substituted with one to four substituents selected from $R^{11}$;
n is 1;
Q is O;
W is O;
X is O;
Z is selected from the group consisting of $Z^1$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy.

Particular preference is given to phenylethers of formula (I.a) (corresponds to formula (I) wherein Y is $Y^2$, wherein $R^{19}$ is Br, $R^{20}$ is $CF_3$ and $R^{21}$ is $CH_3$ and $R^4$ is H, n is 1, Q, W and X are O, and Z is Z-1 as defined, wherein $R^a$, $R^b$, $R^c$ and $R^d$ are H:

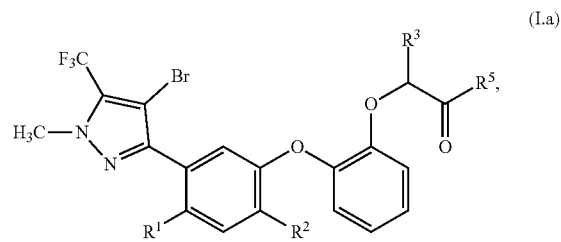

(I.a)

wherein the variables $R^1$, $R^2$, $R^3$ and $R^5$ have the meanings, in particular the preferred meanings, as defined above.

Special preference is given to the compounds of the formulae I.a.1 to I.a.36 of Table A, where the definitions of the variables $R^1$, $R^2$, $R^3$ and $R^5$ are of particular importance for the compounds according to the invention not only in combination with one another but in each case also on their own:

TABLE A

| No. | $R^1$ | $R^2$ | $R^3$ | $R^5$ |
|---|---|---|---|---|
| I.a.1. | H | F | H | OH |
| I.a.2. | H | F | H | $OCH_3$ |
| I.a.3. | H | F | H | $OC_2H_5$ |
| I.a.4. | H | F | H | $NHSO_2CH_3$ |
| I.a.5. | H | Cl | H | OH |
| I.a.6. | H | Cl | H | $OCH_3$ |

TABLE A-continued

| No. | $R^1$ | $R^2$ | $R^3$ | $R^5$ |
|---|---|---|---|---|
| I.a.7. | H | Cl | H | $OC_2H_5$ |
| I.a.8. | H | Cl | H | $NHSO_2CH_3$ |
| I.a.9. | H | CN | H | OH |
| I.a.10. | H | CN | H | $OCH_3$ |
| I.a.11. | H | CN | H | $OC_2H_5$ |
| I.a.12. | H | CN | H | $NHSO_2CH_3$ |
| I.a.13. | F | F | H | OH |
| I.a.14. | F | F | H | $OCH_3$ |
| I.a.15. | F | F | H | $OC_2H_5$ |
| I.a.16. | F | F | H | $NHSO_2CH_3$ |
| I.a.17. | F | Cl | H | OH |
| I.a.18. | F | Cl | H | $OCH_3$ |
| I.a.19. | F | Cl | H | $OC_2H_5$ |
| I.a.20. | F | Cl | H | $NHSO_2CH_3$ |
| I.a.21. | F | CN | H | OH |
| I.a.22. | F | CN | H | $OCH_3$ |
| I.a.23. | F | CN | H | $OC_2H_5$ |
| I.a.24. | F | CN | H | $NHSO_2CH_3$ |
| I.a.25. | Cl | F | H | OH |
| I.a.26. | Cl | F | H | $OCH_3$ |
| I.a.27. | Cl | F | H | $OC_2H_5$ |
| I.a.28. | Cl | F | H | $NHSO_2CH_3$ |
| I.a.29. | Cl | Cl | H | OH |
| I.a.30. | Cl | Cl | H | $OCH_3$ |
| I.a.31. | Cl | Cl | H | $OC_2H_5$ |
| I.a.32. | Cl | Cl | H | $NHSO_2CH_3$ |
| I.a.33. | Cl | CN | H | OH |
| I.a.34. | Cl | CN | H | $OCH_3$ |
| I.a.35. | Cl | CN | H | $OC_2H_5$ |
| I.a.36. | Cl | CN | H | $NHSO_2CH_3$ |

Also preferred are the phenylethers of formula (I.b), particularly preferred the phenylethers of formulae (I.b.1) to (I.b.36), which differ from the corresponding phenylethers of formulae (I.a.1) to (I.a.36) only in that Y is $Y^2$, wherein $R^{21}$ is Cl, $R^{23}$ is $OCHF_2$ and $R^{21}$ is $OH_3$:

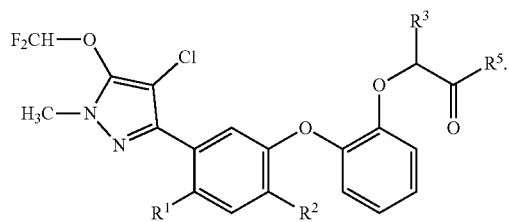

(I.b)

Also preferred are the phenylethers of formula (I.c), particularly preferred the phenylethers of formulae (I.c.1) to (I.c.36), which differ from the corresponding phenylethers of formulae (I.a.1) to (I.a.36) only in that Y is $Y^{13}$, wherein $A^1$ and $A^2$ are O, $R^{19}$ is H and $R^{21}$ and $R^{22}$ together form —$(CH_2$—CHF—$CH_2)$—:

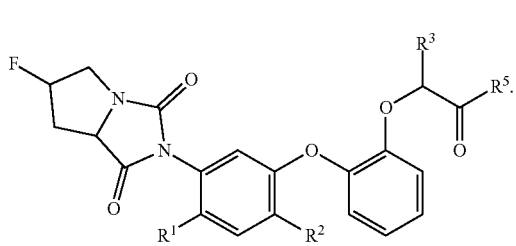

(I.c)

Also preferred are the phenylethers of formula (I.d), particularly preferred the phenylethers of formulae (I.d.1) to (I.d.36), which differ from the corresponding phenylethers of formulae (I.a.1) to (I.a.36) only in that Y is $Y^{13}$, wherein $A^1$ and $A^2$ are O, $R^{19}$ is H and $R^{21}$ and $R^{22}$ together form —$(CH_2$—CHF—$CH_2)$— in form of the (6S,7aR) stereoisomer:

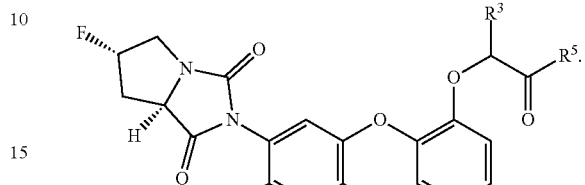

(I.d)

Also preferred are the pyridylethers of formula (I.e), particularly preferred the pyridylethers of formulae (I.e.1) to (I.e.36), which differ from the corresponding pyridylethers of formulae (I.a.1) to (I.a.36) only in that Y is $Y^{68}$ with $A^1$ is O, $R^{12}$ is $CF_3$, $R^{35}$ is $CH_3$:

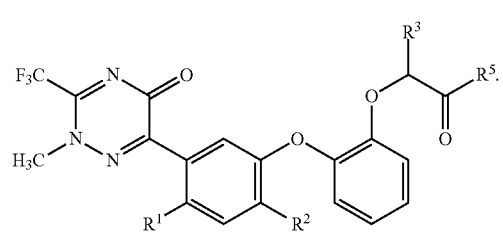

(I.e)

Also preferred are the phenylethers of formula (I.f), particularly preferred the phenylethers of formulae (I.f.1) to (I.f.36), which differ from the corresponding phenylethers of formulae (I.a.1) to (I.a.36) only in that Y is $Y^{20}$ herein $A^1$ is O:

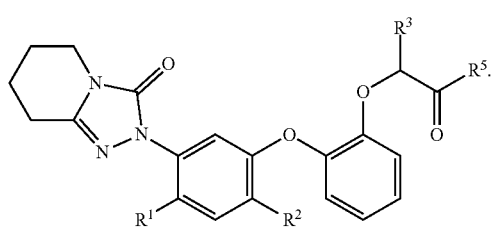

(I.f)

Also preferred are the phenylethers of formula (I.g), particularly preferred the phenylethers of formulae (I.g.1) to (I.g.36), which differ from the corresponding phenylethers of formulae (I.a.1) to (I.a.36) only in that Y is $Y^{31}$, wherein $A^1$ and $A^2$ are O, and $R^{26}$ and $R^{27}$ are $CH_3$:

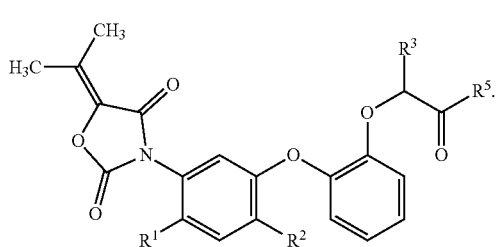
(I.g)

Also preferred are the phenylethers of formula (I.h), particularly preferred the phenylethers of formulae (I.h.1) to (I.h.36), which differ from the corresponding phenylethers of formulae (I.a.1) to (I.a.36) only in that Y is $Y^{37}$, wherein $A^1$ is O, $A^4$ is S and $R^{21}$ and $R^{22}$ together form —(CH$_2$)$_4$—:

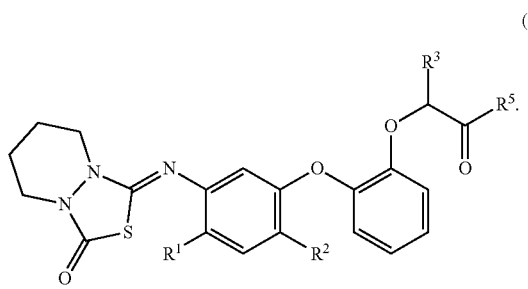
(I.h)

Also preferred are the phenylethers of formula (I.i), particularly preferred the phenylethers of formulae (I.i.1) to (I.i.36), which differ from the corresponding phenylethers of formulae (I.a.1) to (I.a.36) only in that Y is $Y^{38}$, wherein $A^1$ is O and $R^{28}$ is C(CH$_3$)$_3$:

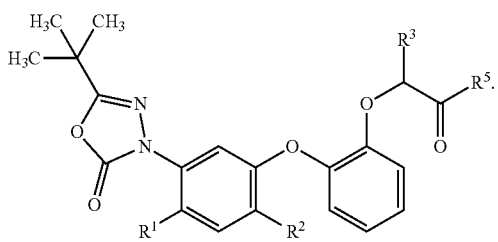
(I.i)

Also preferred are the phenylethers of formula (I.k), particularly preferred the phenylethers of formulae (I.k.1) to (I.k.36), which differ from the corresponding phenylethers of formulae (I.a.1) to (I.a.36) only in that Y is $Y^{39}$, wherein $A^1$ is S and $R^{21}$ and $R^{22}$ together form

—(CH$_2$—C(CH$_3$)$_2$—CH$_2$)—:

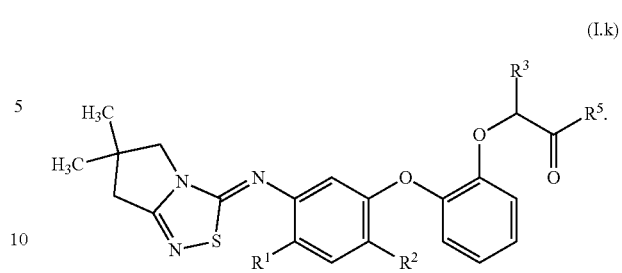
(I.k)

Also preferred are the phenylethers of formula (I.k), particularly preferred the phenylethers of formulae (I.l.1) to (I.k.36), which differ from the corresponding phenylethers of formulae (I.a.1) to (I.a.36) only in that Y is $Y^{42}$, wherein $R^{30}$ is Cl, $R^{14}$ is H, $R^{16}$ is CF$_3$ and $R^{15}$ is H:

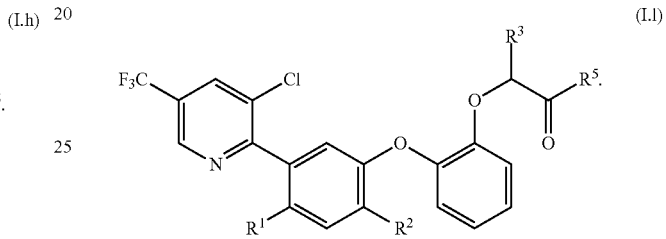
(I.l)

Also preferred are the phenylethers of formula (I.m), particularly preferred the phenylethers of formulae (I.m.1) to (I.m.36), which differ from the corresponding phenylethers of formulae (I.a.1) to (I.a.36) only in that Y is $Y^{48}$, wherein $A^1$ is O, $R^{32}$ is CF$_3$ and $R^{35}$ is CH$_3$:

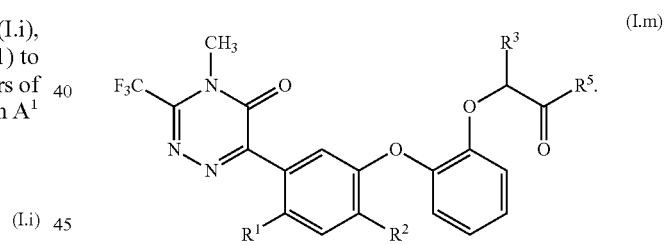
(I.m)

Also preferred are the phenylethers of formula (I.n), particularly preferred the phenylethers of formulae (I.n.1) to (I.n.36), which differ from the corresponding phenylethers of formulae (I.a.1) to (I.a.36) only in that Y is $Y^{55}$, wherein $A^1$ is O, $R^{12}$ is CF$_3$ and $R^{35}$ and $R^{37}$ are CH$_3$:

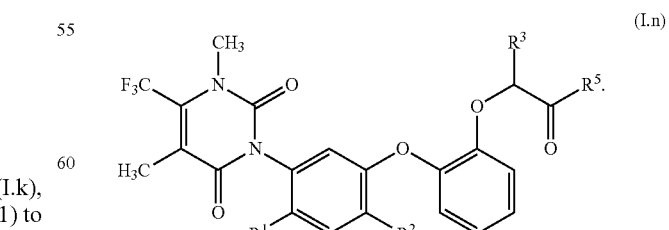
(I.n)

Also preferred are the phenylethers of formula (I.o), particularly preferred the phenylethers of formulae (I.o.1) to (I.o.36), which differ from the corresponding phenylethers of formulae (I.a.1) to (I.a.36) only in that Y is Y$^{65}$, wherein A$^1$ is O, R$^{12}$ is H, R$^{13}$ is CF$_3$ and R$^{35}$ is CH$_3$:

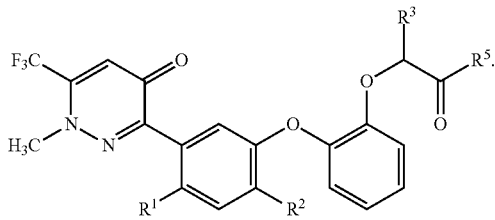

(I.o)

Also preferred are the phenylethers of formula (I.p), particularly preferred the phenylethers of formulae (I.p.1) to (I.p.36), which differ from the corresponding phenylethers of formulae (I.a.1) to (I.a.36) only in that Y is Y$^{66}$, wherein A$^1$ is O, R$^{12}$ is CF$_3$, R$^{13}$ is H and R$^{35}$ is CH$_3$:

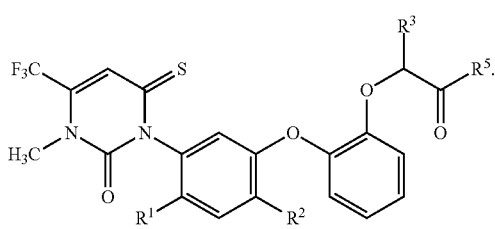

(I.p)

Also preferred are the phenylethers of formula (I.q), particularly preferred the phenylethers of formulae (I.q.1) to (I.q.36), which differ from the corresponding phenylethers of formulae (I.a.1) to (I.a.36) only in that Y is Y$^{67}$, wherein A$^1$ and A$^2$ are O, A$^3$ is S, R$^{35}$ and R$^{36}$ is CH$_3$:

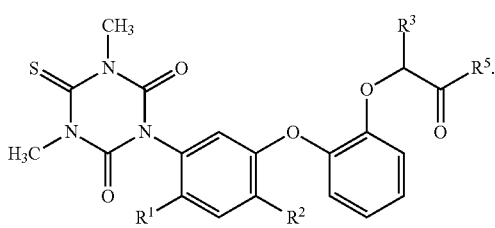

(I.q)

Also preferred are the phenylethers of formula (I.r), particularly preferred the phenylethers of formulae (I.r.1) to (I.r.36), which differ from the corresponding phenylethers of formulae (I.a.1) to (I.a.36) only in that Y is Y$^{69}$, wherein A$^1$ and A$^2$ are O and R$^{32}$ and R$^{33}$ are H

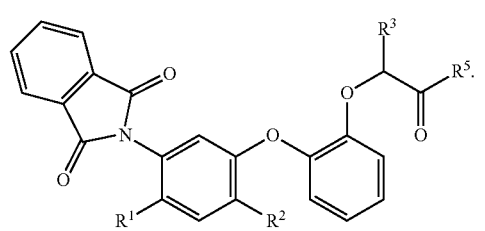

(I.r)

Also preferred are the phenylethers of formula (I.s), particularly preferred the phenylethers of formulae (I.s.1) to (I.s.36), which differ from the corresponding phenylethers of formulae (I.a.1) to (I.a.36) only in that Z is Z-7 as defined, wherein R$^a$, R$^b$ and R$^c$ are H:

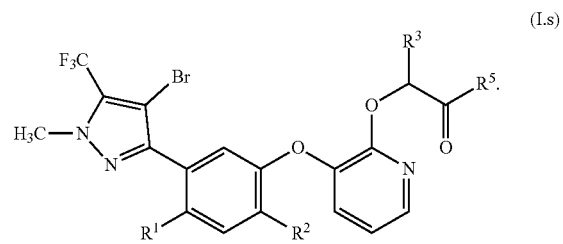

(I.s)

Also preferred are the phenylethers of formula (I.t), particularly preferred the phenylethers of formulae (I.t.1) to (I.t.36), which differ from the corresponding phenylethers of formulae (I.a.1) to (I.a.36) only in that Y is Y$^2$, wherein R$^{28}$ is Cl, R$^{23}$ is OCHF$_2$ and R$^{24}$ is CH$_3$, and Z is Z-7 as defined, wherein R$^a$, R$^b$ and R$^c$ are H:

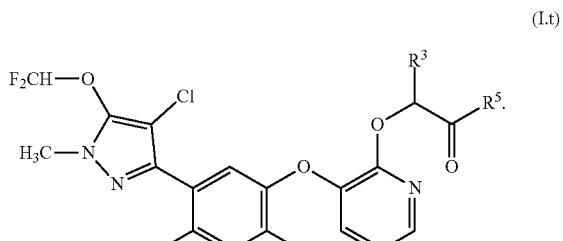

(I.t)

Also preferred are the phenylethers of formula (I.u), particularly preferred the phenylethers of formulae (I.u.1) to (I.u.36), which differ from the corresponding phenylethers of formulae (I.a.1) to (I.a.36) only in that Y is Y$^{13}$, wherein A$^1$ and A$^2$ are O, R$^{19}$ is H and R$^{21}$ and R$^{22}$ together form —(CH$_2$—CHF—CH$_2$)—, and Z is Z-7 as defined, wherein R$^a$, R$^b$ and R$^c$ are H:

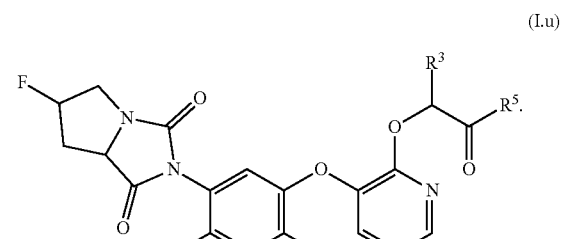

(I.u)

Also preferred are the phenylethers of formula (I.v), particularly preferred the phenylethers of formulae (I.v.1) to (I.v.36), which differ from the corresponding phenylethers of formulae (I.a.1) to (I.a.36) only in that Y is Y$^{13}$, wherein A$^1$ and A$^2$ are O, R$^{19}$ is H and R$^{21}$ and R$^{22}$ together form —(CH$_2$—CHF—CH$_2$)—, in form of the (6S,7aR) stereoisomer and Z is Z-7 as defined, wherein R$^a$, R$^b$ and R$^c$ are H:

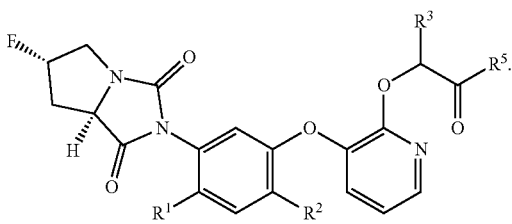

(I.v)

Also preferred are the pyridylethers of formula (I.w), particularly preferred the pyridylethers of formulae (I.w.1) to (I.w.36), which differ from the corresponding pyridylethers of formulae (I.a.1) to (I.a.36) only in that Y is $Y^{68}$ with $A^1$ is O, $R^{12}$ is $CF_3$ and $R^{35}$ is $CH_3$, and Z is Z-7 as defined, wherein $R^a$, $R^b$ and $R^c$ are H:

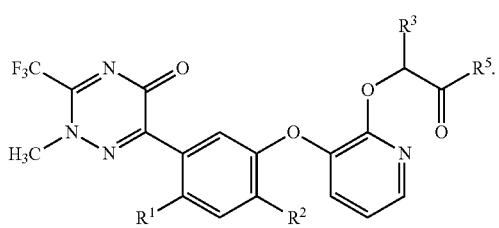

(I.w)

Also preferred are the phenylethers of formula (I.x), particularly preferred the phenylethers of formulae (I.x.1) to (I.x.36), which differ from the corresponding phenylethers of formulae (I.a.1) to (I.a.36) only in that Y is $Y^{20}$ with $A^1$ is O and $R^{21}$ and $R^{22}$ together form —$(CH_2)_4$—, and Z is Z-7 as defined, wherein $R^a$, $R^b$ and $R^c$ are H:

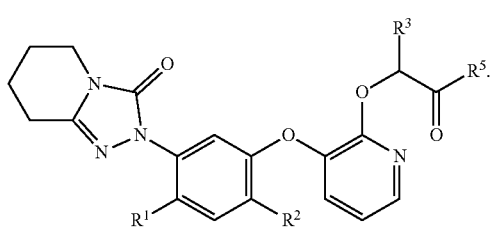

(I.x)

Also preferred are the phenylethers of formula (I.y), particularly preferred the phenylethers of formulae (I.y.1) to (I.y.36), which differ from the corresponding phenylethers of formulae (I.a.1) to (I.a.36) only in that Y is $Y^{31}$, wherein $A^1$ and $A^2$ are O, and $R^{26}$ and $R^{27}$ are $CH_3$, and Z is Z-7 as defined, wherein $R^a$, $R^b$ and $R^c$ are H:

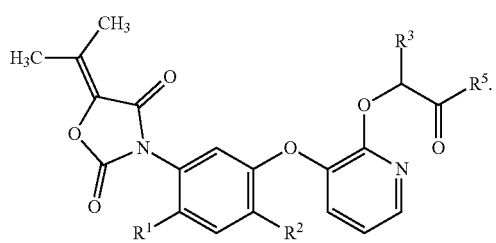

(I.y)

Also preferred are the phenylethers of formula (I.z), particularly preferred the phenylethers of formulae (I.z.1) to (I.z.36), which differ from the corresponding phenylethers of formulae (I.a.1) to (I.a.36) only in that Y is $Y^{37}$, wherein $A^1$ is O, $A^4$ is S and $R^{21}$ and $R^{22}$ together form —$(CH_2)_4$—, and Z is Z-7 as defined, wherein $R^a$, $R^b$ and $R^c$ are H:

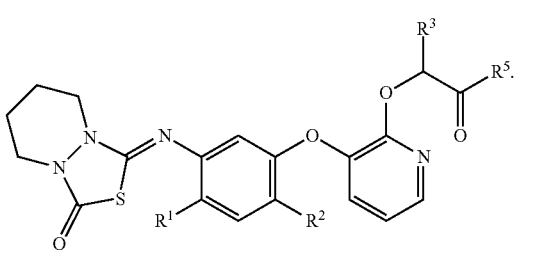

(I.z)

Also preferred are the phenylethers of formula (I.aa), particularly preferred the phenylethers of formulae (I.aa.1) to (I.aa.36), which differ from the corresponding phenylethers of formulae (I.a.1) to (I.a.36) only in that Y is $Y^{38}$, wherein $A^1$ is O and $R^{28}$ is $C(CH_3)_3$, and Z is Z-7 as defined, wherein $R^a$, $R^b$ and $R^c$ are H:

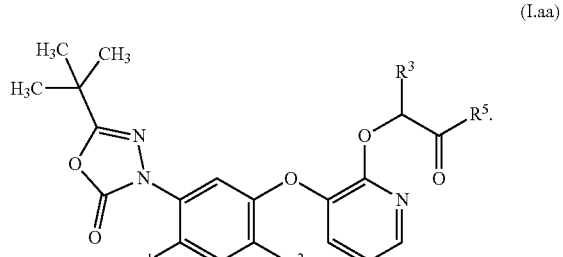

(I.aa)

Also preferred are the phenylethers of formula (I.ab), particularly preferred the phenylethers of formulae (I.ab.1) to (I.ab.36), which differ from the corresponding phenylethers of formulae (I.a.1) to (I.a.36) only in that Y is $Y^{39}$, wherein $A^1$ is S and $R^{21}$ and $R^{22}$ together form —$(CH_2—C(CH_3)_2—CH_2)$—, and Z is Z-7 as defined, wherein $R^a$, $R^b$ and $R^c$ are H:

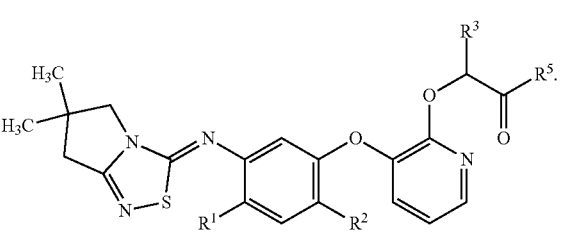

(I.ab)

Also preferred are the phenylethers of formula (I.ac), particularly preferred the phenylethers of formulae (I.ac.1) to (I.ac.36), which differ from the corresponding phenylethers of formulae (I.a.1) to (I.a.36) only in that Y is $Y^{42}$, wherein $R^{30}$ is Cl, $R^{14}$ is H, $R^{16}$ is $CF_3$ and $R^{15}$ is H, and Z is Z-7 as defined, wherein $R^a$, $R^b$ and $R^c$ are H:

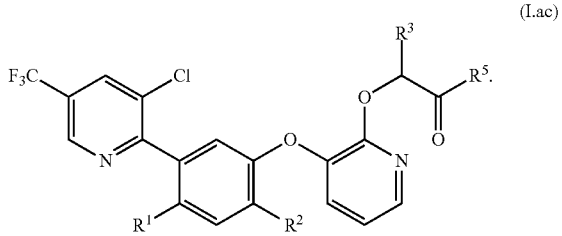

(I.ac)

Also preferred are the phenylethers of formula (I.ad), particularly preferred the phenylethers of formulae (I.ad.1) to (I.ad.36), which differ from the corresponding phenylethers of formulae (I.a.1) to (I.a.36) only in that Y is $Y^{48}$, wherein $A^1$ is O, $R^{32}$ is $CF_3$ and $R^{35}$ is $CH_3$, and Z is Z-7 as defined, wherein $R^a$, $R^b$ and $R^c$ are H:

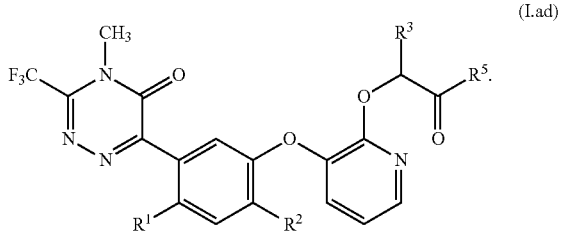

(I.ad)

Also preferred are the phenylethers of formula (I.ae), particularly preferred the phenylethers of formulae (I.ae.1) to (I.ae.36), which differ from the corresponding phenylethers of formulae (I.a.1) to (I.a.36) only in that Y is $Y^{55}$, wherein $A^1$ is O, $R^{12}$ is $CF_3$, $R^{35}$ and $R^{37}$ are $CH_3$, and Z is Z-7 as defined, wherein $R^a$, $R^b$ and $R^c$ are H:

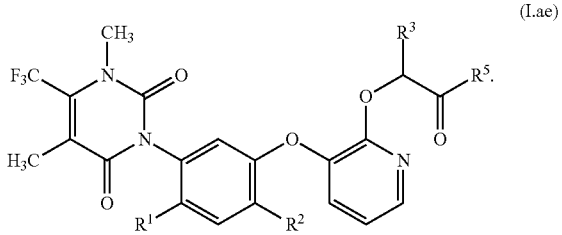

(I.ae)

Also preferred are the phenylethers of formula (I.af), particularly preferred the phenylethers of formulae (I.af.1) to (I.af.36), which differ from the corresponding phenylethers of formulae (I.a.1) to (I.a.36) only in that Y is $Y^{65}$, wherein $A^1$ is O, $R^{12}$ is H, $R^{13}$ is $CF_3$ and $R^{35}$ is $CH_3$, and Z is Z-7 as defined, wherein $R^a$, $R^b$ and $R^c$ are H:

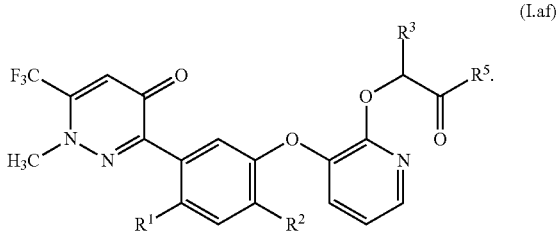

(I.af)

Also preferred are the phenylethers of formula (I.ag), particularly preferred the phenylethers of formulae (I.ag.1) to (I.ag.36), which differ from the corresponding phenylethers of formulae (I.a.1) to (I.a.36) only in that Y is $Y^{66}$, wherein $A^1$ is O, $R^{12}$ is $CF_3$, $R^{13}$ is H and $R^{35}$ is $CH_3$, and Z is Z-7 as defined, wherein $R^a$, $R^b$ and $R^c$ are H:

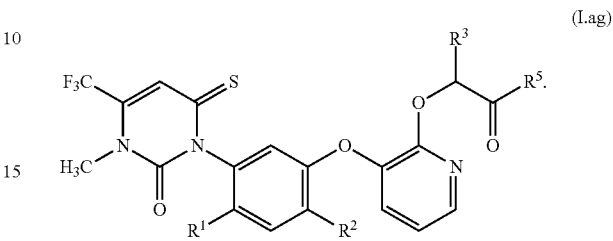

(I.ag)

Also preferred are the phenylethers of formula (I.ah), particularly preferred the phenylethers of formulae (I.ah.1) to (I.ah.36), which differ from the corresponding phenylethers of formulae (I.a.1) to (I.a.36) only in that Y is $Y^{67}$, wherein $A^1$ and $A^2$ are O, $A^3$ is S, $R^{35}$ and $R^{36}$ is $CH_3$, and Z is Z-7 as defined, wherein $R^a$, $R^b$ and $R^c$ are H:

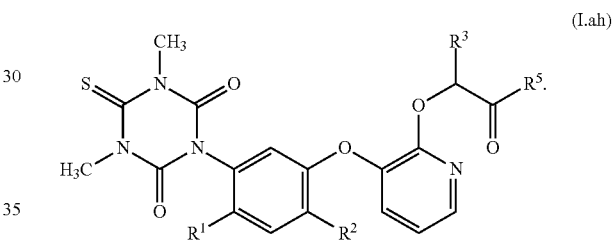

(I.ah)

Also preferred are the phenylethers of formula (I.ai), particularly preferred the phenylethers of formulae (I.ai.1) to (I.ai.36), which differ from the corresponding phenylethers of formulae (I.a.1) to (I.a.36) only in that Y is $Y^{69}$, wherein $A^1$ and $A^2$ are O, $R^{32}$ and $R^{33}$ are H, and Z is Z-7 as defined, wherein $R^a$, $R^b$ and $R^c$ are H:

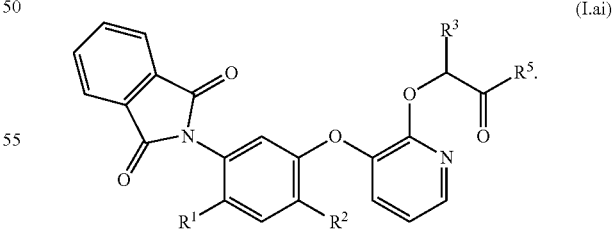

(I.ai)

The phenylethers of formula (I) according to the invention can be prepared by standard processes of organic chemistry, for example by the following processes A and B:

Phenylethers of formula (I), wherein Y is a hereocycle, which is bond via a N-atom to the central phenyl ring, can be prepared from amino compounds of formula (II) in analogy to known processes:

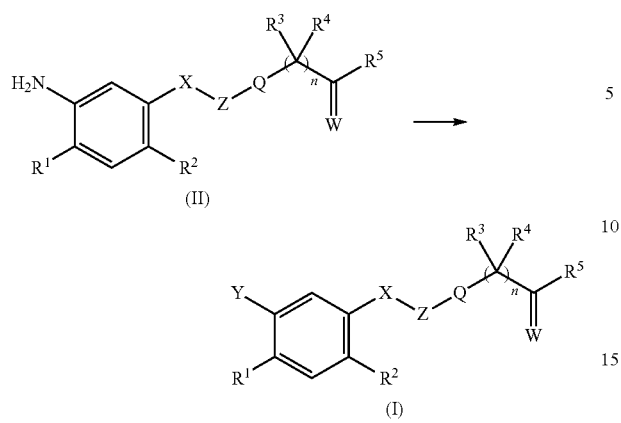

(II)

(I)

The methods used to convert compounds (II) into phenylethers of formula (I) depend on the nature of the group Y.

These methods are described inter alia in Chemical Biology & Drug Design 2014, 84 (4), 431-442 (Y8, Y9), Bioorganic & Medicinal Chemistry 2010, 18 (22), 7948-7956 (Y10), JP 01139580 (Y11), EP 1 157 991 (Y12), EP 311 135 (Y13, Y17, Y38, Y39), DE 39 22 107 (Y14, Y31), JP 11292720 (Y15), U.S. Pat. No. 4,670,043 (Y16), EP 334 055 (Y17, Y38), U.S. Pat. No. 4,213,773 (Y20), EP 75 267 (Y18), EP 863 142 (Y19), WO 96/18618 (Y21), EP 282 303 (Y22), EP 305 923 (Y23), U.S. Pat. No. 6,333,296 (Y24), Bioorganic & Medicinal Chemistry Letters 2010, 20 (5), 1510-1515 (Y25, Y26), WO 2008/011072 (Y30), DE 39 22 107 (Y14, Y31), JP 07304759 (Y32), JP 06016664 (Y33), WO 2008/030902 (Y34), EP 683 160 (Y35), U.S. Pat. No. 5,726,126 (Y36), WO 96/02523 (Y37), WO 92/21684 (Y37), EP 334 055 (Y17, Y20, Y38), WO 93/03043 (Y39, 62), EP 454 444 (Y50), CN 1687061 (Y51), EP 1 095 935 (Y52), EP 985 670 (Y53), J. Chem. Soc., Perkin Trans. 1: Organic and Bio-Organic Chemistry 1993, (6), 731-5 (Y54), EP 869 123 (Y55), WO 2010/100189 (Y56), WO 99/11634 (Y57), WO 86/00072 (Y58), WO 2012/002096 (Y59), EP 640 600 (Y60, Y67), Zeitschrift für Chemie 1986, 26(4), 134-136 (Y61), EP 371 240 (Y63, Y64), WO 98/41093 (Y66), WO 10/145992 (Y67), WO 2000/013508 (Y69), CN 1355164 (Y70).

Phenylethers of formula (I), wherein Y is a hereocycle, which is bond via a C-atom to the central phenyl ring, can also be prepared by a cross-coupling reaction of compounds of formula (III) with compounds of formula (IV) in the presence of a transition metal catalyst in analogy to known processes (e.g. WO 95/22547 ($Y^2$), WO 98/07720 ($Y^{42}$), WO 02/042275 ($Y^{42}$), JP 2009137851 ($Y^{45}$) and WO 17/036266 ($Y^{65}$):

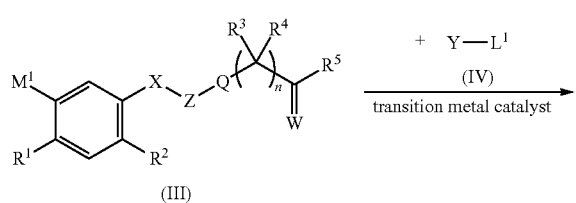

(III)

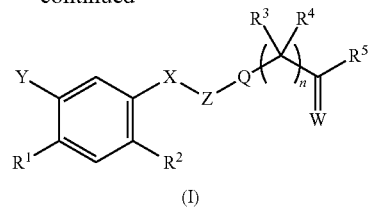

(I)

Within the compounds of formula (III),
$M^1$ is a boronic acid, boronic acid alkyl ester, Sn-tri($C_1$-$C_4$-alkyl);
especially preferred $B(OH)_2$, $B(O(C_1$-$C_{10}$-alkyl))$_2$ or Sn-tri($C_1$-$C_4$-alkyl);
more preferred $BO_2C_2(CH_3)_4$ (="B-pin") or Sn-tri($C_1$-$C_4$-alkyl).

Within the compounds of formula (VIII),
$L^1$ is a leaving group such halogen or $OSO_2CF_3$ (triflate);
especially preferred I, Br, Cl, or $OSO_2CF_3$;
more preferred I or Br.

The reaction is usually carried out from 0° C. to the boiling point of the reaction mixture, preferably from 15° C. to 110° C., particularly from 40° C. to 100° C., in an inert organic solvent in the presence of a base and a catalyst.

The reaction may in principle be carried out in substance. However, preference is given to reacting the compounds of formula (VII) with the compounds of formula (VIII) in an organic solvent with or without water as co-solvent.

Suitable solvents are those capable of dissolving the compounds of formula (VII) and the compounds of formula (VIII) at least partly and preferably fully under reaction conditions.

Examples of suitable solvents are aromatic hydrocarbons such as benzene, chlorobenzene, toluene, cresols, o-, m- and p-xylene; ethers such as diethyl ether, diisopropyl ether, tert.-butyl methylether (TBME), dioxane, anisole and tetrahydrofuran (THF); as well as dipolar aprotic solvents such as sulfolane, N,N-dimethylformamide (DMF), N,N-dimethylacetamide (DMAC), 1,3-dimethyl-2-imidazolinone (DMI), N,N'-dimethylpropylene urea (DMPU), dimethyl sulfoxide (DMSO) and 1-methyl-2-pyrrolidinone (NMP).

Preferred solvents are ethers such as diethyl ether, diisopropyl ether, tert.-butyl methylether (TBME), dioxane, anisole and tetrahydrofuran (THF) and dipolar aprotic solvents such as sulfolane, N,N-dimethylformamide (DMF), N,N-dimethylacetamide (DMAC), 1,3-dimethyl-2-imidazolinone (DMI), N,N'-dimethylpropylene urea (DMPU), dimethyl sulfoxide (DMSO) and 1-methyl-2-pyrrolidinone (NMP). More preferred solvents are ethers such as diethyl ether, diisopropyl ether, tert.-butyl methylether (TBME), dioxane, anisole and tetrahydrofuran (THF). It is also possible to use mixtures of the solvents mentioned.

Examples of suitable metal-containing bases are inorganic compounds including metal-containing bases such as alkali metal and alkaline earth metal hydroxides, and other metal hydroxides, such as LiOH, NaOH, KOH, $Mg(OH)_2$, $Ca(OH)_2$ and $Al(OH)_3$; alkali metal and alkaline earth metal oxide, and other metal oxides, such as $Li_2O$, $Na_2O$, $K_2O$, MgO, and CaO, $Fe_2O_3$, $Ag_2O$; alkali metal and alkaline earth metal carbonates such as $Li_2CO_3$, $Na_2CO_3$, $K_2CO_3$, $Cs2CO_3$, $MgCO_3$, and $CaCO_3$, as well as alkali metal bicarbonates such as $LiHCO_3$, $NaHCO_3$, $KHCO_3$; alkali metal and alkaline earth metal phosphates such as $K_3PO_4$, $Ca_3(PO_4)_2$; alkali metal and alkaline earth metal acetates such as sodium acetate or potassium acetate.

Preferred bases are inorganic compounds such as alkali metal and alkaline earth metal hydroxides, and other metal hydroxides, such as LiOH, NaOH, KOH, Mg(OH)$_2$, Ca(OH)$_2$ and Al(OH)$_3$ and alkali metal or alkaline earth metal carbonates such as Li$_2$CO$_3$, Na$_2$CO$_3$, K$_2$CO$_3$, Cs2CO$_3$, MgCO$_3$, and CaCO$_3$ and alkaline earth metal phosphates such as K$_3$PO$_4$; alkali metal and alkaline earth metal acetates such as sodium acetate. Especially preferred bases are inorganic compounds such as alkali metal and alkaline earth metal hydroxides, and other metal hydroxides, such as LiOH, NaOH, KOH, Mg(OH)$_2$, Ca(OH)$_2$ and Al(OH)$_3$ and alkaline earth metal phosphates such as K$_3$PO$_4$.

The term base as used herein also includes mixtures of two or more, preferably two of the above compounds. Particular preference is given to the use of one base.

The bases are used preferably at from 1 to 10 equivalents based on the compound of formula (III), more preferably at from 1.0 to 5.0 equivalents based on the compound of formula (III), most preferably from 1.2 to 2.5 equivalents based on the compound of formula (III It may be advantageous to add the base offset over a period of time.

The reaction of compounds of formula (III) with the compounds of formula (IV) is carried out in the presence of a catalyst. Examples of suitable catalysts include e.g., palladium based catalysts like, e.g., palladium(II)acetate, tetrakis(triphenylphosphine)-palladium(0), bis(triphenyl-phosphine)palladium(II)chloride or (1,1,-bis(diphenylphosphino)-ferrocene)-dichloropalladium(II), and optionally suitable additives such as, e.g., phosphines like, e.g., P(o-tolyl)$_3$, triphenylphosphine or BINAP (2,2'-Bis(diphenylphospino)-1,1'-binaphthyl).

The amount of catalyst is usually 0.01 to 20 mol % (0.0001 to 0.2 equivalents) based on the compounds of formula (III).

The intermediates necessary for preparation of the phenylethers of formula (I) according to the invention, and mentioned in processes A and B above, are commercially available or can be prepared by standard processes of organic chemistry, for example by the following processes:

Amino compounds of formula (II) (necessary for process A mentioned above) can be prepared by reduction from the respective nitro compounds (V):

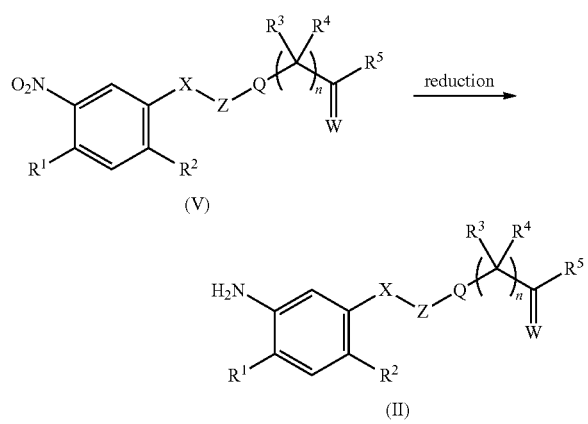

The reduction can for example be achieved by treatment with iron powder in acetic acid at a temperature ranging from 0° C. to 100° C. Alternatively, the reduction can be carried out by catalytic hydrogenation in hydrogen gas at a pressure of 70 to 700 kPa, preferably 270 to 350 kPa, in the presence of a metal catalyst such as palladium supported on an inert carrier such as activated carbon, in a weight ratio of 5 to 20% of metal to carrier, suspended in a solvent such as ethanol at ambient temperature (see e.g. WO 2011/137088).

Compounds of formula (III) can be prepared from compounds of formula (VII) in presence of a transition metal catalyst:

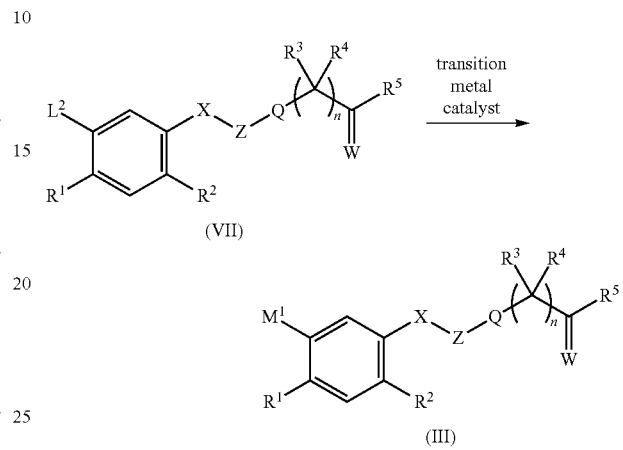

Within the compounds of formula (VII),
L$^2$ is a leaving group such halogen or OSO$_2$CF$_3$ (triflate); especially preferred I, Br, Cl, or OSO$_2$CF$_3$;
more preferred I or Br.

Compounds of formula (IV) required for the preparation of the compounds of formula (I) according to process B are commercially available or known from literature.

Nitro compounds of formula (V) can be prepared by nitration reaction of the respective compounds of formula (VI) following the known literature procedures (Langlois, B. in Introduction of Nitrogen group by exchange of hydrogen for the nitro group; Baasner, B., Hagemann, H., Tatlow, J. C., Eds.; Houben-Weyl, Methods of Organic Chemistry; 1974; 4th Edition, Vol. 11, R—NH$_2$ Compounds, pp 479-870):

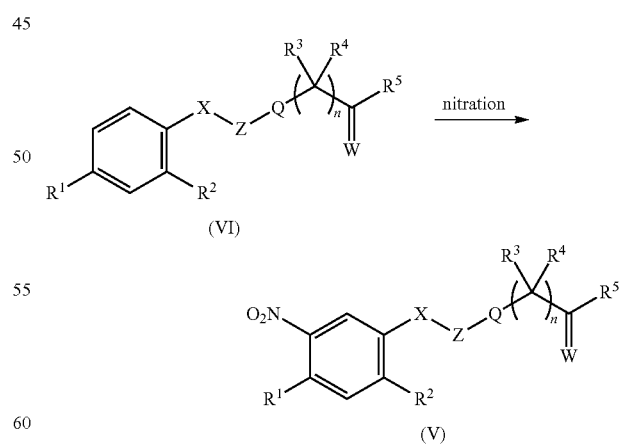

Compounds of formula (VI) required for the preparation of the nitro compounds of formula (V) are commercially available or known from literature.

Compounds of formula (VII) can be prepared by reaction of compounds of formula (VIII) with alkylating agents of formula (IX) in the presence of a base in analogy to known processes (e.g. WO 11/137088):

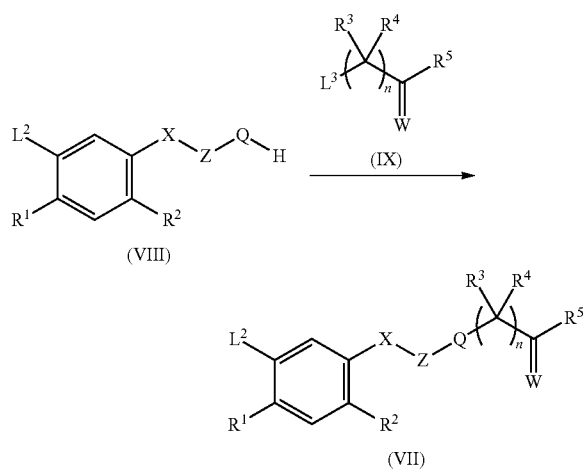

Within the alkylating agents of formula (IX),
$L^3$ is a leaving group such halogen, $C_1$-$C_6$-alkylsulfonate or arylsulfonate;
preferably Cl, Br, I, $C_1$-$C_6$-alkylsulfonate or arylsulfonate;
especially preferred Cl, Br or I;
more preferred Cl or Br.

Compounds of formula (VIII) required for the preparation of the compounds of formula (VII) are commercially available, known from literature or can be prepared by known methods (e.g. WO 11/137088).

Alkylating agents of formula (IX) are commercially available or can be prepared by known methods (e.g. Lowell, Andrew N. et al, Tetrahedron, 6(30), 5573-5582, 2010; WO 11/137088).

To widen the spectrum of action and to achieve synergistic effects, the phenylethers of formula (I) may be mixed with a large number of representatives of other herbicidal or growth-regulating active ingredient groups and then applied concomitantly. Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the phenylethers of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

In one embodiment of the present invention the compositions according to the present invention comprise at least one phenylether of formula (I) (compound A) and at least one further active compound selected from herbicides B, preferably herbicides B of class b1) to b15), and safeners C (compound C).

In another embodiment of the present invention the compositions according to the present invention comprise at least one phenylether of formula (I) and at least one further active compound B (herbicide B).

The further herbicidal compound B (component B) is preferably selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives.

Preference is given to those compositions according to the present invention comprising at least one herbicide B selected from herbicides of class b2, b3, b4, b5, b6, b7, b9, b10 and b13.

Specific preference is given to those compositions according to the present invention which comprise at least one herbicide B selected from the herbicides of class b4, b6, b7, b9, b10 and b13.

Particular preference is given to those compositions according to the present invention which comprise at least one herbicide B selected from the herbicides of class b4, b6, b10 and b13.

Examples of herbicides B which can be used in combination with the phenylethers of formula (I) according to the present invention are:
b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl] amino]-benzoic acid-1-methylethyl ester (CAS 420138-41-6), 4-[[[2-[(4,6-dimethoxy-2-pyrimidinyl) oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl] imidazolidin-2-one; (CAS 2023785-78-4), 4-hydroxy-1,5-dimethyl-3-[4-(trifluoromethyl)-2-pyridyl] imidazolidin-2-one (CAS 2023785-79-5), 5-ethoxy-4-hydroxy-1-methyl-3-[4-(trifluoromethyl)-2-pyridyl] imidazolidin-2-one (CAS 1701416-69-4), 4-hydroxy-1-methyl-3-[4-(trifluoromethyl)-2-pyridyl] imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, chlorphthalim, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoro-methylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoro-methylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole, flumeturon, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:

chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae I1.1, I1.2, I1.3, I1.4, I1.5, I1.6, I1.7, I1.8 and I1.9

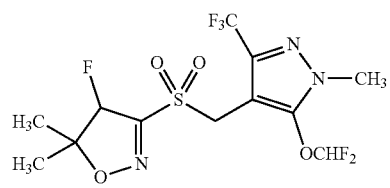

II.1

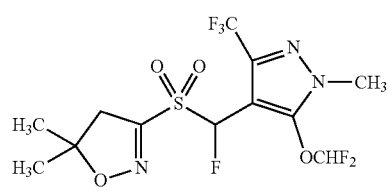

II.2

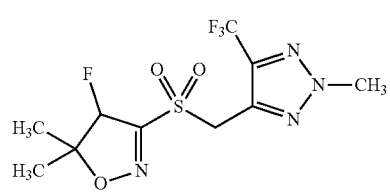

II.3

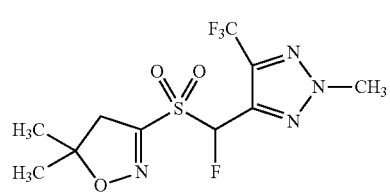

II.4

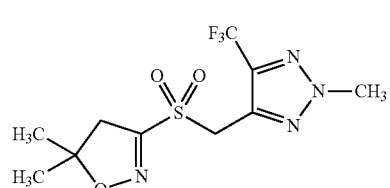

II.5

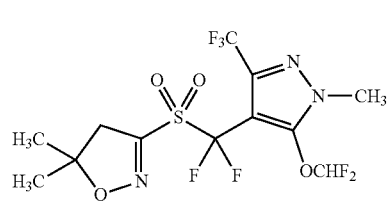

II.6

-continued

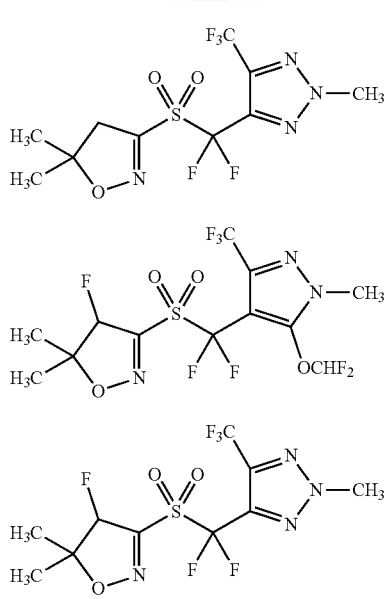

the isoxazoline compounds of the formula (I)I are known in the art, e.g. from WO 2006/024820, WO 2006/037945, WO 2007/071900 and WO 2007/096576; among the VLCFA inhibitors, preference is given to chloroacetamides and oxyacetamides;
b11) from the group of the cellulose biosynthesis inhibitors:
chlorthiamid, dichlobenil, flupoxam, indaziflam, isoxaben, triaziflam and 1-cyclohexyl-5-pentafluorphenyloxy-14-[1,2,4,6]thiatriazin-3-ylamine (CAS 175899-01-1); b12) from the group of the decoupler herbicides:
dinoseb, dinoterb and DNOC and its salts;
b13) from the group of the auxinic herbicides:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);
b14) from the group of the auxin transport inhibitors:
diflufenzopyr, diflufenzopyr-sodium, naptalam and naptalam-sodium;
b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinmerac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicides B are the herbicides B as defined above; in particular the herbicides B.1-B.202 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |

TABLE B-continued

Herbicide B

| | |
|---|---|
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | pyraflufen |
| B.93 | pyraflufen-ethyl |
| B.94 | saflufenacil |
| B.95 | sulfentrazone |
| B.96 | trifludimoxazin |
| B.97 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) |
| B.98 | benzobicyclon |
| B.99 | bicyclopyrone |
| B.100 | clomazone |
| B.101 | diflufenican |
| B.102 | flurochloridone |
| B.103 | isoxaflutole |
| B.104 | mesotrione |
| B.105 | norflurazone |
| B.106 | picolinafen |
| B.107 | sulcotrione |
| B.108 | tefuryltrione |
| B.109 | tembotrione |
| B.110 | tolpyralate |
| B.111 | topramezone |
| B.112 | topramezone-sodium |
| B.113 | amitrole |
| B.114 | fluometuron |
| B.115 | fenquinotrione |
| B.116 | glyphosate |
| B.117 | glyphosate-ammonium |
| B.118 | glyphosate-dimethylammonium |
| B.119 | glyphosate-isopropylammonium |
| B.120 | glyphosate-trimesium (sulfosate) |
| B.121 | glyphosate-potassium |
| B.122 | glufosinate |
| B.123 | glufosinate-ammonium |
| B.124 | glufosinate-P |
| B.125 | glufosinate-P-ammonium |
| B.126 | pendimethalin |
| B.127 | trifluralin |
| B.128 | acetochlor |
| B.129 | butachlor |
| B.130 | cafenstrole |
| B.131 | dimethenamid-P |
| B.132 | fentrazamide |
| B.133 | flufenacet |
| B.134 | mefenacet |
| B.135 | metazachlor |
| B.136 | metolachlor |
| B.137 | S-metolachlor |
| B.138 | pretilachlor |
| B.139 | fenoxasulfone |
| B.140 | indaziflam |
| B.141 | isoxaben |
| B.142 | triaziflam |
| B.143 | ipfencarbazone |
| B.144 | pyroxasulfone |
| B.145 | 2,4-D |
| B.146 | 2,4-D-isobutyl |
| B.147 | 2,4-D-dimethylammonium |
| B.148 | 2,4-D-N,N,N-trimethylethanolammonium |
| B.149 | aminopyralid |
| B.150 | aminopyralid-methyl |
| B.151 | aminopyralid-dimethyl-ammonium |
| B.152 | aminopyralid-tris(2-hydroxypropyl)ammonium |
| B.153 | clopyralid |
| B.154 | clopyralid-methyl |
| B.155 | clopyralid-olamine |
| B.156 | dicamba |
| B.157 | dicamba-butotyl |
| B.158 | dicamba-diglycolamine |
| B.159 | dicamba-dimethylammonium |
| B.160 | dicamba-diolamine |
| B.161 | dicamba-isopropylammonium |
| B.162 | dicamba-potassium |
| B.163 | dicamba-sodium |
| B.164 | dicamba-trolamine |
| B.165 | dicamba-N,N-bis-(3-aminopropyl)methylamine |
| B.166 | dicamba-diethylenetriamine |
| B.167 | fluroxypyr |
| B.168 | fluroxypyr-meptyl |
| B.169 | halauxifen |
| B.170 | halauxifen-methyl |
| B.171 | MCPA |
| B.172 | MCPA-2-ethylhexyl |
| B.173 | MCPA-dimethylammonium |
| B.174 | quinclorac |
| B.175 | quinclorac-dimethylammonium |
| B.176 | quinmerac |
| B.177 | quinmerac-dimethylammonium |
| B.178 | florpyrauxifen |
| B.179 | florpyrauxifen-benzyl (CAS 1390661-72-9) |
| B.180 | aminocyclopyrachlor |
| B.181 | aminocyclopyrachlor-potassium |
| B.182 | aminocyclopyrachlor-methyl |
| B.183 | diflufenzopyr |
| B.184 | diflufenzopyr-sodium |
| B.185 | dymron |
| B.186 | indanofan |
| B.187 | oxaziclomefone |
| B.188 | II.1 |
| B.189 | II.2 |
| B.190 | II.3 |
| B.191 | II.4 |
| B.192 | II.5 |
| B.193 | II.6 |
| B.194 | II.7 |
| B.195 | II.8 |
| B.196 | II.9 |
| B.197 | 4-amino-3-chloro-5-fluoro-6-(7-fluoro-1H-indol-6-yl)picolinic acid (CAS 1629965-65-6) |
| B.198 | flopyrauxifen |
| B.199 | oxotrione (CAS 1486617-21-3) |
| B.200 | cinmethylin |
| B.201 | 2-chloro-3-methylsulfanyl-N-(1-methyltetrazol-5-yl)-4-(trifluoromethyl)benzamide (CAS 1361139-71-0) |
| B.202 | 2-(2,4-dichlorophenyl)-methyl-4,4-dimethyl-3-isoxazolidone (CAS 81777-95-9) |

Moreover, it may be useful to apply the phenylethers of formula (I) in combination with safeners. Safeners are chemical compounds which prevent or reduce damage on useful plants without having a major impact on the herbicidal action of the phenylethers of the formula (I) towards unwanted plants. They can be applied either before sowings (e.g. on seed treatments, shoots or seedlings) or in the pre-emergence application or post-emergence application of the useful plant. The safeners and the phenylethers of formula (I) and optionally the herbicides B can be applied simultaneously or in succession.

In another embodiment of the present invention the compositions according to the present invention comprise at least one phenylether of formula (I) and at least one safener C (component C).

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4), metcamifen (CAS 129531-12-0) and BPCMS.

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | metcamifen |

The active compounds B of groups b1) to b15) and the active compounds C are known herbicides and safeners, see, for example, The Compendium of Pesticide Common Names (www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as herbicidal active compounds B or component B at least four, preferably exactly four herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one, preferably exactly one compound of formula (I), preferably of formula (I.a), (I.b), (I.l), (I.n), (I.p), (I.q), (I.s), (I.t), (I.ac), (I.ae), (I.ag) or (I.ah), and as component B at least one, preferably exactly one, herbicide B.

According to another preferred embodiment of the invention, the composition comprises as component A at least one, preferably exactly one compound of formula (I), preferably of formula (I.a), (I.b), (I.l), (I.n), (I.p), (I.q), (I.s), (I.t), (I.ac), (I.ae), (I.ag) or (I.ah), and at least two, preferably exactly two, herbicides B different from each other.

According to another preferred embodiment of the invention, the composition comprises as component A at least one, preferably exactly one compound of formula (I), preferably of formula (I.a), (I.b), (I.l), (I.n), (I.p), (I.q), (I.s), (I.t), (I.ac), (I.ae), (I.ag) or (I.ah), and at least three, preferably exactly three, herbicides B different from each other.

According to another preferred embodiment of the invention, the composition comprises as component A at least one, preferably exactly one compound of formula (I), preferably of formula (I.a), (I.b), (1.1), (I.n), (I.p), (I.q), (I.s), (I.t), (I.ac), (I.ae), (I.ag) or (I.ah), and at least four, preferably exactly four, herbicides B different from each other.

According to another preferred embodiment of the invention, the composition comprises as component A at least one, preferably exactly one compound of formula (I), preferably of formula (I.a), (I.b), (1.1), (I.n), (I.p), (I.q), (I.s), (I.t), (I.ac), (I.ae), (I.ag) or (I.ah), and as component C at least one, preferably exactly one, safener C.

According to another preferred embodiment of the invention, the composition comprises as component A at least one, preferably exactly one compound of formula (I), preferably of formula (I.a), (I.b), (1.1), (I.n), (I.p), (I.q), (I.s), (I.t), (I.ac), (I.ae), (I.ag) or (I.ah), as component B at least one, preferably exactly one, herbicide B, and as component C at least one, preferably exactly one safener C.

According to another preferred embodiment of the invention, the composition comprises as component A at least one, preferably exactly one compound of formula (I), preferably of formula (I.a), (I.b), (1.1), (I.n), (I.p), (I.q), (I.s), (I.t), (I.ac), (I.ae), (I.ag) or (I.ah), at least two, preferably exactly two herbicides B different from each other, and as component C at least one, preferably exactly one, safener C.

According to another preferred embodiment of the invention, the composition comprises as component A at least one, preferably exactly one compound of formula (I), preferably of formula (I.a), (I.b), (1.1), (I.n), (I.p), (I.q), (I.s), (I.t), (I.ac), (I.ae), (I.ag) or (I.ah), at least three, preferably exactly three herbicides B different from each other, and as component C at least one, preferably exactly one, safener C.

According to another preferred embodiment of the invention, the composition comprises, in addition to an phenylether of formula (I), especially an active compound from the group consisting of (I.a.18), (I.a.19), (I.b.18), (I.b.19), (1.1.18), (1.1.19), (I.n.18), (I.n.19), (I.p.18), (I.p.19), (I.q.18), (I.q.19), (I.s.18), (I.s.19), (I.t.18), (I.t.19), (I.ac.18), (I.ac.19), (I.ae.18), (I.ae.19), (I.ag.18), (I.ag.19), (I.ah.18) and (I.ah.19), at least one and especially exactly one herbicidally active compound from group b4), in particular selected from the group consisting of acifluorfen, butafencil, carfenetrazone-ethyl, flumioxazin, fomesafen, oxadiargyl, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100).

According to another preferred embodiment of the invention, the composition comprises, in addition to an phenylether of formula (I), especially an active compound from the group consisting of (I.a.18), (I.a.19), (I.b.18), (I.b.19), (1.1.18), (1.1.19), (I.n.18), (I.n.19), (I.p.18), (I.p.19), (I.q.18), (I.q.19), (I.s.18), (I.s.19), (I.t.18), (I.t.19), (I.ac.18), (I.ac.19), (I.ae.18), (I.ae.19), (I.ag.18), (I.ag.19), (I.ah.18) and (I.ah.19), at least one and especially exactly one herbicidally active compound from group b6), in particular selected from the group consisting of glyphosate, glyphosate-ammonium, glyphosate-dimethylammonium, glyphosate-isopropylammonium and glyphosate-trimesium (sulfosate) and glyphosate-potassium.

According to another preferred embodiment of the invention, the composition comprises, in addition to an phenylether of formula (I), especially an active compound from the group consisting of (I.a.18), (I.a.19), (I.b.18), (I.b.19), (I.l.18), (I.l.19), (I.n.18), (I.n.19), (I.p.18), (I.p.19), (I.q.18), (I.q.19), (I.s.18), (I.s.19), (I.t.18), (I.t.19), (I.ac.18), (I.ac.19), (I.ae.18), (I.ae.19), (I.ag.18), (I.ag.19), (I.ah.18) and (I.ah.19), at least one and especially exactly one herbicidally active compound from group b10), in particular selected from the group consisting of acetochlor, butachlor, cafenstrole, dimethenamid-P, fentrazamide, flufenacet, mefenacet, metazachlor, metolachlor, S-metolachlor, fenoxasulfone, ipfencarbazone and pyroxasulfone. Likewise, preference is given to compositions comprising in addition to an phenylether of formula (I), especially an active compound from the group consisting of (I.a.18), (I.a.19), (I.b.18), (I.b.19), (I.l.18), (I.l.19), (I.n.18), (I.n.19), (I.p.18), (I.p.19), (I.q.18), (I.q.19), (I.s.18), (I.s.19), (I.t.18), (I.t.19), (I.ac.18), (I.ac.19), (I.ae.18), (I.ae.19), (I.ag.18), (I.ag.19), (I.ah.18) and (I.ah.19), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to an phenylether of formula (I), especially an active compound from the group consisting of (I.a.18), (I.a.19), (I.b.18), (I.b.19), (I.l.18), (I.l.19), (I.n.18), (I.n.19), (I.p.18), (I.p.19), (I.q.18), (I.q.19), (I.s.18), (I.s.19), (I.t.18), (I.t.19), (I.ac.18), (I.ac.19), (I.ae.18), (I.ae.19), (I.ag.18), (I.ag.19), (I.ah.18) and (I.ah.19), at least one and especially exactly one herbicidally active compound from group b13), in particular selected from the group consisting of 2,4-D, 2,4-D-isobutyl, 2,4-D-dimethylammonium, 2,4-D-N,N,N-trimethylethanolammonium, aminocyclopyrachlor, aminocyclopyrachlor-potassium, aminocyclopyrachlor-methyl, aminopyralid, aminopyralid-methyl, aminopyralid-dimethylammonium, aminopyralid-tris(2-hydroxypropyl)ammonium, clopyralid, clopyralid-methyl, clopyralid-olamine, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine, dicamba-diethylenetriamine, flopyrauxifen, fluroxypyr, fluroxypyr-meptyl, halauxifen, halauxifen-methyl, MCPA, MCPA-2-ethylhexyl, MCPA-dimethylammonium, quinclorac, quinclorac-dimethylammonium, quinmerac, quinmerac-dimethylammonium, florpyrauxifen, florpyrauxifen-benzyl (CAS 1390661-72-9), and 4-amino-3-chloro-5-fluoro-6-(7-fluoro-1H-indol-6-yl)picolinic acid.

Here and below, the term "binary compositions" includes compositions comprising one or more, for example 1, 2 or 3, active compounds of the formula (I) and either one or more, for example 1, 2 or 3, herbicides B or one or more safeners C.

Correspondingly, the term "ternary compositions" includes compositions comprising one or more, for example 1, 2 or 3, active compounds of the formula (I), one or more, for example 1, 2 or 3, herbicides B and one or more, for example 1, 2 or 3, safeners C.

In binary compositions comprising at least one compound of the formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:125 to 125:1.

In binary compositions comprising at least one compound of the formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one phenylether of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:125 to 125:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given herein, in particular within the preferred limits.

Particularly preferred are the compositions mentioned below comprising the phenylethers of formula (I) as defined and the substance(s) as defined in the respective row of table 1;

- especially preferred comprising as only herbicidal active compounds the phenylethers of formula (I) as defined and the substance(s) as defined in the respective row of table 1;
- most preferably comprising as only active compounds the phenylethers of formula (I) as defined and the substance(s) as defined in the respective row of table 1.

Particularly preferred are compositions 1.1 to 1.3653, comprising the phenylether (I.a.18) and the substance(s) as defined in the respective row of table 1:

TABLE 1

(compositions 1.1 to 1.3653):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58 | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |

TABLE 1-continued (compositions 1.1 to 1.3653):

| comp. no. | herbicide B | safener C |
|---|---|---|
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |
| 1.196 | B.196 | — |
| 1.197 | B.197 | — |
| 1.198 | B.198 | — |
| 1.199 | B.199 | — |
| 1.200 | B.200 | — |
| 1.201 | B.201 | — |
| 1.202 | B.202 | — |
| 1.203 | B.1 | C.1 |
| 1.204 | B.2 | C.1 |
| 1.205 | B.3 | C.1 |
| 1.206 | B.4 | C.1 |
| 1.207 | B.5 | C.1 |
| 1.208 | B.6 | C.1 |
| 1.209 | B.7 | C.1 |
| 1.210 | B.8 | C.1 |
| 1.211 | B.9 | C.1 |
| 1.212 | B.10 | C.1 |
| 1.213 | B.11 | C.1 |
| 1.214 | B.12 | C.1 |
| 1.215 | B.13 | C.1 |
| 1.216 | B.14 | C.1 |
| 1.217 | B.15 | C.1 |
| 1.218 | B.16 | C.1 |
| 1.219 | B.17 | C.1 |
| 1.220 | B.18 | C.1 |
| 1.221 | B.19 | C.1 |
| 1.222 | B.20 | C.1 |
| 1.223 | B.21 | C.1 |
| 1.224 | B.22 | C.1 |
| 1.225 | B.23 | C.1 |
| 1.226 | B.24 | C.1 |
| 1.227 | B.25 | C.1 |
| 1.228 | B.26 | C.1 |
| 1.229 | B.27 | C.1 |
| 1.230 | B.28 | C.1 |
| 1.231 | B.29 | C.1 |
| 1.232 | B.30 | C.1 |
| 1.233 | B.31 | C.1 |
| 1.234 | B.32 | C.1 |
| 1.235 | B.33 | C.1 |
| 1.236 | B.34 | C.1 |
| 1.237 | B.35 | C.1 |
| 1.238 | B.36 | C.1 |
| 1.239 | B.37 | C.1 |
| 1.240 | B.38 | C.1 |
| 1.241 | B.39 | C.1 |
| 1.242 | B.40 | C.1 |
| 1.243 | B.41 | C.1 |
| 1.244 | B.42 | C.1 |
| 1.245 | B.43 | C.1 |
| 1.246 | B.44 | C.1 |
| 1.247 | B.45 | C.1 |
| 1.248 | B.46 | C.1 |
| 1.249 | B.47 | C.1 |
| 1.250 | B.48 | C.1 |
| 1.251 | B.49 | C.1 |
| 1.252 | B.50 | C.1 |
| 1.253 | B.51 | C.1 |
| 1.254 | B.52 | C.1 |
| 1.255 | B.53 | C.1 |
| 1.256 | B.54 | C.1 |
| 1.257 | B.55 | C.1 |
| 1.258 | B.56 | C.1 |
| 1.259 | B.57 | C.1 |
| 1.260 | B.58 | C.1 |
| 1.261 | B.59 | C.1 |
| 1.262 | B.60 | C.1 |
| 1.263 | B.61 | C.1 |
| 1.264 | B.62 | C.1 |
| 1.265 | B.63 | C.1 |
| 1.266 | B.64 | C.1 |
| 1.267 | B.65 | C.1 |
| 1.268 | B.66 | C.1 |
| 1.269 | B.67 | C.1 |
| 1.270 | B.68 | C.1 |
| 1.271 | B.69 | C.1 |
| 1.272 | B.70 | C.1 |
| 1.273 | B.71 | C.1 |
| 1.274 | B.72 | C.1 |
| 1.275 | B.73 | C.1 |
| 1.276 | B.74 | C.1 |
| 1.277 | B.75 | C.1 |
| 1.278 | B.76 | C.1 |
| 1.279 | B.77 | C.1 |
| 1.280 | B.78 | C.1 |
| 1.281 | B.79 | C.1 |
| 1.282 | B.80 | C.1 |
| 1.283 | B.81 | C.1 |
| 1.284 | B.82 | C.1 |
| 1.285 | B.83 | C.1 |

TABLE 1-continued (compositions 1.1 to 1.3653):

| comp. no. | herbicide B | safener C |
|---|---|---|
| 1.286 | B.84 | C.1 |
| 1.287 | B.85 | C.1 |
| 1.288 | B.86 | C.1 |
| 1.289 | B.87 | C.1 |
| 1.290 | B.88 | C.1 |
| 1.291 | B.89 | C.1 |
| 1.292 | B.90 | C.1 |
| 1.293 | B.91 | C.1 |
| 1.294 | B.92 | C.1 |
| 1.295 | B.93 | C.1 |
| 1.296 | B.94 | C.1 |
| 1.297 | B.95 | C.1 |
| 1.298 | B.96 | C.1 |
| 1.299 | B.97 | C.1 |
| 1.300 | B.98 | C.1 |
| 1.301 | B.99 | C.1 |
| 1.302 | B.100 | C.1 |
| 1.303 | B.101 | C.1 |
| 1.304 | B.102 | C.1 |
| 1.305 | B.103 | C.1 |
| 1.306 | B.104 | C.1 |
| 1.307 | B.105 | C.1 |
| 1.308 | B.106 | C.1 |
| 1.309 | B.107 | C.1 |
| 1.310 | B.108 | C.1 |
| 1.311 | B.109 | C.1 |
| 1.312 | B.110 | C.1 |
| 1.313 | B.111 | C.1 |
| 1.314 | B.112 | C.1 |
| 1.315 | B.113 | C.1 |
| 1.316 | B.114 | C.1 |
| 1.317 | B.115 | C.1 |
| 1.318 | B.116 | C.1 |
| 1.319 | B.117 | C.1 |
| 1.320 | B.118 | C.1 |
| 1.321 | B.119 | C.1 |
| 1.322 | B.120 | C.1 |
| 1.323 | B.121 | C.1 |
| 1.324 | B.122 | C.1 |
| 1.325 | B.123 | C.1 |
| 1.326 | B.124 | C.1 |
| 1.327 | B.125 | C.1 |
| 1.328 | B.126 | C.1 |
| 1.329 | B.127 | C.1 |
| 1.330 | B.128 | C.1 |
| 1.331 | B.129 | C.1 |
| 1.332 | B.130 | C.1 |
| 1.333 | B.131 | C.1 |
| 1.334 | B.132 | C.1 |
| 1.335 | B.133 | C.1 |
| 1.336 | B.134 | C.1 |
| 1.337 | B.135 | C.1 |
| 1.338 | B.136 | C.1 |
| 1.339 | B.137 | C.1 |
| 1.340 | B.138 | C.1 |
| 1.341 | B.139 | C.1 |
| 1.342 | B.140 | C.1 |
| 1.343 | B.141 | C.1 |
| 1.344 | B.142 | C.1 |
| 1.345 | B.143 | C.1 |
| 1.346 | B.144 | C.1 |
| 1.347 | B.145 | C.1 |
| 1.348 | B.146 | C.1 |
| 1.349 | B.147 | C.1 |
| 1.350 | B.148 | C.1 |
| 1.351 | B.149 | C.1 |
| 1.352 | B.150 | C.1 |
| 1.353 | B.151 | C.1 |
| 1.354 | B.152 | C.1 |
| 1.355 | B.153 | C.1 |
| 1.356 | B.154 | C.1 |
| 1.357 | B.155 | C.1 |
| 1.358 | B.156 | C.1 |
| 1.359 | B.157 | C.1 |
| 1.360 | B.158 | C.1 |
| 1.361 | B.159 | C.1 |
| 1.362 | B.160 | C.1 |
| 1.363 | B.161 | C.1 |
| 1.364 | B.162 | C.1 |
| 1.365 | B.163 | C.1 |
| 1.366 | B.164 | C.1 |
| 1.367 | B.165 | C.1 |
| 1.368 | B.166 | C.1 |
| 1.369 | B.167 | C.1 |
| 1.370 | B.168 | C.1 |
| 1.371 | B.169 | C.1 |
| 1.372 | B.170 | C.1 |
| 1.373 | B.171 | C.1 |
| 1.374 | B.172 | C.1 |
| 1.375 | B.173 | C.1 |
| 1.376 | B.174 | C.1 |
| 1.377 | B.175 | C.1 |
| 1.378 | B.176 | C.1 |
| 1.379 | B.177 | C.1 |
| 1.380 | B.178 | C.1 |
| 1.381 | B.179 | C.1 |
| 1.382 | B.180 | C.1 |
| 1.383 | B.181 | C.1 |
| 1.384 | B.182 | C.1 |
| 1.385 | B.183 | C.1 |
| 1.386 | B.184 | C.1 |
| 1.387 | B.185 | C.1 |
| 1.388 | B.186 | C.1 |
| 1.389 | B.187 | C.1 |
| 1.390 | B.188 | C.1 |
| 1.391 | B.189 | C.1 |
| 1.392 | B.190 | C.1 |
| 1.393 | B.191 | C.1 |
| 1.394 | B.192 | C.1 |
| 1.395 | B.193 | C.1 |
| 1.396 | B.194 | C.1 |
| 1.397 | B.195 | C.1 |
| 1.398 | B.196 | C.1 |
| 1.399 | B.197 | C.1 |
| 1.400 | B.198 | C.1 |
| 1.401 | B.199 | C.1 |
| 1.402 | B.200 | C.1 |
| 1.403 | B.201 | C.1 |
| 1.404 | B.202 | C.1 |
| 1.405 | B.1 | C.2 |
| 1.406 | B.2 | C.2 |
| 1.407 | B.3 | C.2 |
| 1.408 | B.4 | C.2 |
| 1.409 | B.5 | C.2 |
| 1.410 | B.6 | C.2 |
| 1.411 | B.7 | C.2 |
| 1.412 | B.8 | C.2 |
| 1.413 | B.9 | C.2 |
| 1.414 | B.10 | C.2 |
| 1.415 | B.11 | C.2 |
| 1.416 | B.12 | C.2 |
| 1.417 | B.13 | C.2 |
| 1.418 | B.14 | C.2 |
| 1.419 | B.15 | C.2 |
| 1.420 | B.16 | C.2 |
| 1.421 | B.17 | C.2 |
| 1.422 | B.18 | C.2 |
| 1.423 | B.19 | C.2 |
| 1.424 | B.20 | C.2 |
| 1.425 | B.21 | C.2 |
| 1.426 | B.22 | C.2 |
| 1.427 | B.23 | C.2 |
| 1.428 | B.24 | C.2 |
| 1.429 | B.25 | C.2 |
| 1.430 | B.26 | C.2 |
| 1.431 | B.27 | C.2 |
| 1.432 | B.28 | C.2 |
| 1.433 | B.29 | C.2 |
| 1.434 | B.30 | C.2 |
| 1.435 | B.31 | C.2 |
| 1.436 | B.32 | C.2 |
| 1.437 | B.33 | C.2 |

TABLE 1-continued (compositions 1.1 to 1.3653):

| comp. no. | herbicide B | safener C |
|---|---|---|
| 1.438 | B.34 | C.2 |
| 1.439 | B.35 | C.2 |
| 1.440 | B.36 | C.2 |
| 1.441 | B.37 | C.2 |
| 1.442 | B.38 | C.2 |
| 1.443 | B.39 | C.2 |
| 1.444 | B.40 | C.2 |
| 1.445 | B.41 | C.2 |
| 1.446 | B.42 | C.2 |
| 1.447 | B.43 | C.2 |
| 1.448 | B.44 | C.2 |
| 1.449 | B.45 | C.2 |
| 1.450 | B.46 | C.2 |
| 1.451 | B.47 | C.2 |
| 1.452 | B.48 | C.2 |
| 1.453 | B.49 | C.2 |
| 1.454 | B.50 | C.2 |
| 1.455 | B.51 | C.2 |
| 1.456 | B.52 | C.2 |
| 1.457 | B.53 | C.2 |
| 1.458 | B.54 | C.2 |
| 1.459 | B.55 | C.2 |
| 1.460 | B.56 | C.2 |
| 1.461 | B.57 | C.2 |
| 1.462 | B.58 | C.2 |
| 1.463 | B.59 | C.2 |
| 1.464 | B.60 | C.2 |
| 1.465 | B.61 | C.2 |
| 1.466 | B.62 | C.2 |
| 1.467 | B.63 | C.2 |
| 1.468 | B.64 | C.2 |
| 1.469 | B.65 | C.2 |
| 1.470 | B.66 | C.2 |
| 1.471 | B.67 | C.2 |
| 1.472 | B.68 | C.2 |
| 1.473 | B.69 | C.2 |
| 1.474 | B.70 | C.2 |
| 1.475 | B.71 | C.2 |
| 1.476 | B.72 | C.2 |
| 1.477 | B.73 | C.2 |
| 1.478 | B.74 | C.2 |
| 1.479 | B.75 | C.2 |
| 1.480 | B.76 | C.2 |
| 1.481 | B.77 | C.2 |
| 1.482 | B.78 | C.2 |
| 1.483 | B.79 | C.2 |
| 1.484 | B.80 | C.2 |
| 1.485 | B.81 | C.2 |
| 1.486 | B.82 | C.2 |
| 1.487 | B.83 | C.2 |
| 1.488 | B.84 | C.2 |
| 1.489 | B.85 | C.2 |
| 1.490 | B.86 | C.2 |
| 1.491 | B.87 | C.2 |
| 1.492 | B.88 | C.2 |
| 1.493 | B.89 | C.2 |
| 1.494 | B.90 | C.2 |
| 1.495 | B.91 | C.2 |
| 1.496 | B.92 | C.2 |
| 1.497 | B.93 | C.2 |
| 1.498 | B.94 | C.2 |
| 1.499 | B.95 | C.2 |
| 1.500 | B.96 | C.2 |
| 1.501 | B.97 | C.2 |
| 1.502 | B.98 | C.2 |
| 1.503 | B.99 | C.2 |
| 1.504 | B.100 | C.2 |
| 1.505 | B.101 | C.2 |
| 1.506 | B.102 | C.2 |
| 1.507 | B.103 | C.2 |
| 1.508 | B.104 | C.2 |
| 1.509 | B.105 | C.2 |
| 1.510 | B.106 | C.2 |
| 1.511 | B.107 | C.2 |
| 1.512 | B.108 | C.2 |
| 1.513 | B.109 | C.2 |
| 1.514 | B.110 | C.2 |
| 1.515 | B.111 | C.2 |
| 1.516 | B.112 | C.2 |
| 1.517 | B.113 | C.2 |
| 1.518 | B.114 | C.2 |
| 1.519 | B.115 | C.2 |
| 1.520 | B.116 | C.2 |
| 1.521 | B.117 | C.2 |
| 1.522 | B.118 | C.2 |
| 1.523 | B.119 | C.2 |
| 1.524 | B.120 | C.2 |
| 1.525 | B.121 | C.2 |
| 1.526 | B.122 | C.2 |
| 1.527 | B.123 | C.2 |
| 1.528 | B.124 | C.2 |
| 1.529 | B.125 | C.2 |
| 1.530 | B.126 | C.2 |
| 1.531 | B.127 | C.2 |
| 1.532 | B.128 | C.2 |
| 1.533 | B.129 | C.2 |
| 1.534 | B.130 | C.2 |
| 1.535 | B.131 | C.2 |
| 1.536 | B.132 | C.2 |
| 1.537 | B.133 | C.2 |
| 1.538 | B.134 | C.2 |
| 1.539 | B.135 | C.2 |
| 1.540 | B.136 | C.2 |
| 1.541 | B.137 | C.2 |
| 1.542 | B.138 | C.2 |
| 1.543 | B.139 | C.2 |
| 1.544 | B.140 | C.2 |
| 1.545 | B.141 | C.2 |
| 1.546 | B.142 | C.2 |
| 1.547 | B.143 | C.2 |
| 1.548 | B.144 | C.2 |
| 1.549 | B.145 | C.2 |
| 1.550 | B.146 | C.2 |
| 1.551 | B.147 | C.2 |
| 1.552 | B.148 | C.2 |
| 1.553 | B.149 | C.2 |
| 1.554 | B.150 | C.2 |
| 1.555 | B.151 | C.2 |
| 1.556 | B.152 | C.2 |
| 1.557 | B.153 | C.2 |
| 1.558 | B.154 | C.2 |
| 1.559 | B.155 | C.2 |
| 1.560 | B.156 | C.2 |
| 1.561 | B.157 | C.2 |
| 1.562 | B.158 | C.2 |
| 1.563 | B.159 | C.2 |
| 1.564 | B.160 | C.2 |
| 1.565 | B.161 | C.2 |
| 1.566 | B.162 | C.2 |
| 1.567 | B.163 | C.2 |
| 1.568 | B.164 | C.2 |
| 1.569 | B.165 | C.2 |
| 1.570 | B.166 | C.2 |
| 1.571 | B.167 | C.2 |
| 1.572 | B.168 | C.2 |
| 1.573 | B.169 | C.2 |
| 1.574 | B.170 | C.2 |
| 1.575 | B.171 | C.2 |
| 1.576 | B.172 | C.2 |
| 1.577 | B.173 | C.2 |
| 1.578 | B.174 | C.2 |
| 1.579 | B.175 | C.2 |
| 1.580 | B.176 | C.2 |
| 1.581 | B.177 | C.2 |
| 1.582 | B.178 | C.2 |
| 1.583 | B.179 | C.2 |
| 1.584 | B.180 | C.2 |
| 1.585 | B.181 | C.2 |
| 1.586 | B.182 | C.2 |
| 1.587 | B.183 | C.2 |
| 1.588 | B.184 | C.2 |
| 1.589 | B.185 | C.2 |

TABLE 1-continued (compositions 1.1 to 1.3653):

| comp. no. | herbicide B | safener C |
|---|---|---|
| 1.590 | B.186 | C.2 |
| 1.591 | B.187 | C.2 |
| 1.592 | B.188 | C.2 |
| 1.593 | B.189 | C.2 |
| 1.594 | B.190 | C.2 |
| 1.595 | B.191 | C.2 |
| 1.596 | B.192 | C.2 |
| 1.597 | B.193 | C.2 |
| 1.598 | B.194 | C.2 |
| 1.599 | B.195 | C.2 |
| 1.600 | B.196 | C.2 |
| 1.601 | B.197 | C.2 |
| 1.602 | B.198 | C.2 |
| 1.603 | B.199 | C.2 |
| 1.604 | B.200 | C.2 |
| 1.605 | B.201 | C.2 |
| 1.606 | B.202 | C.2 |
| 1.607 | B.1 | C.3 |
| 1.608 | B.2 | C.3 |
| 1.609 | B.3 | C.3 |
| 1.610 | B.4 | C.3 |
| 1.611 | B.5 | C.3 |
| 1.612 | B.6 | C.3 |
| 1.613 | B.7 | C.3 |
| 1.614 | B.8 | C.3 |
| 1.615 | B.9 | C.3 |
| 1.616 | B.10 | C.3 |
| 1.617 | B.11 | C.3 |
| 1.618 | B.12 | C.3 |
| 1.619 | B.13 | C.3 |
| 1.620 | B.14 | C.3 |
| 1.621 | B.15 | C.3 |
| 1.622 | B.16 | C.3 |
| 1.623 | B.17 | C.3 |
| 1.624 | B.18 | C.3 |
| 1.625 | B.19 | C.3 |
| 1.626 | B.20 | C.3 |
| 1.627 | B.21 | C.3 |
| 1.628 | B.22 | C.3 |
| 1.629 | B.23 | C.3 |
| 1.630 | B.24 | C.3 |
| 1.631 | B.25 | C.3 |
| 1.632 | B.26 | C.3 |
| 1.633 | B.27 | C.3 |
| 1.634 | B.28 | C.3 |
| 1.635 | B.29 | C.3 |
| 1.636 | B.30 | C.3 |
| 1.637 | B.31 | C.3 |
| 1.638 | B.32 | C.3 |
| 1.639 | B.33 | C.3 |
| 1.640 | B.34 | C.3 |
| 1.641 | B.35 | C.3 |
| 1.642 | B.36 | C.3 |
| 1.643 | B.37 | C.3 |
| 1.644 | B.38 | C.3 |
| 1.645 | B.39 | C.3 |
| 1.646 | B.40 | C.3 |
| 1.647 | B.41 | C.3 |
| 1.648 | B.42 | C.3 |
| 1.649 | B.43 | C.3 |
| 1.650 | B.44 | C.3 |
| 1.651 | B.45 | C.3 |
| 1.652 | B.46 | C.3 |
| 1.653 | B.47 | C.3 |
| 1.654 | B.48 | C.3 |
| 1.655 | B.49 | C.3 |
| 1.656 | B.50 | C.3 |
| 1.657 | B.51 | C.3 |
| 1.658 | B.52 | C.3 |
| 1.659 | B.53 | C.3 |
| 1.660 | B.54 | C.3 |
| 1.661 | B.55 | C.3 |
| 1.662 | B.56 | C.3 |
| 1.663 | B.57 | C.3 |
| 1.664 | B.58 | C.3 |
| 1.665 | B.59 | C.3 |
| 1.666 | B.60 | C.3 |
| 1.667 | B.61 | C.3 |
| 1.668 | B.62 | C.3 |
| 1.669 | B.63 | C.3 |
| 1.670 | B.64 | C.3 |
| 1.671 | B.65 | C.3 |
| 1.672 | B.66 | C.3 |
| 1.673 | B.67 | C.3 |
| 1.674 | B.68 | C.3 |
| 1.675 | B.69 | C.3 |
| 1.676 | B.70 | C.3 |
| 1.677 | B.71 | C.3 |
| 1.678 | B.72 | C.3 |
| 1.679 | B.73 | C.3 |
| 1.680 | B.74 | C.3 |
| 1.681 | B.75 | C.3 |
| 1.682 | B.76 | C.3 |
| 1.683 | B.77 | C.3 |
| 1.684 | B.78 | C.3 |
| 1.685 | B.79 | C.3 |
| 1.686 | B.80 | C.3 |
| 1.687 | B.81 | C.3 |
| 1.688 | B.82 | C.3 |
| 1.689 | B.83 | C.3 |
| 1.690 | B.84 | C.3 |
| 1.691 | B.85 | C.3 |
| 1.692 | B.86 | C.3 |
| 1.693 | B.87 | C.3 |
| 1.694 | B.88 | C.3 |
| 1.695 | B.89 | C.3 |
| 1.696 | B.90 | C.3 |
| 1.697 | B.91 | C.3 |
| 1.698 | B.92 | C.3 |
| 1.699 | B.93 | C.3 |
| 1.700 | B.94 | C.3 |
| 1.701 | B.95 | C.3 |
| 1.702 | B.96 | C.3 |
| 1.703 | B.97 | C.3 |
| 1.704 | B.98 | C.3 |
| 1.705 | B.99 | C.3 |
| 1.706 | B.100 | C.3 |
| 1.707 | B.101 | C.3 |
| 1.708 | B.102 | C.3 |
| 1.709 | B.103 | C.3 |
| 1.710 | B.104 | C.3 |
| 1.711 | B.105 | C.3 |
| 1.712 | B.106 | C.3 |
| 1.713 | B.107 | C.3 |
| 1.714 | B.108 | C.3 |
| 1.715 | B.109 | C.3 |
| 1.716 | B.110 | C.3 |
| 1.717 | B.111 | C.3 |
| 1.718 | B.112 | C.3 |
| 1.719 | B.113 | C.3 |
| 1.720 | B.114 | C.3 |
| 1.721 | B.115 | C.3 |
| 1.722 | B.116 | C.3 |
| 1.723 | B.117 | C.3 |
| 1.724 | B.118 | C.3 |
| 1.725 | B.119 | C.3 |
| 1.726 | B.120 | C.3 |
| 1.727 | B.121 | C.3 |
| 1.728 | B.122 | C.3 |
| 1.729 | B.123 | C.3 |
| 1.730 | B.124 | C.3 |
| 1.731 | B.125 | C.3 |
| 1.732 | B.126 | C.3 |
| 1.733 | B.127 | C.3 |
| 1.734 | B.128 | C.3 |
| 1.735 | B.129 | C.3 |
| 1.736 | B.130 | C.3 |
| 1.737 | B.131 | C.3 |
| 1.738 | B.132 | C.3 |
| 1.739 | B.133 | C.3 |
| 1.740 | B.134 | C.3 |
| 1.741 | B.135 | C.3 |

TABLE 1-continued (compositions 1.1 to 1.3653):

| comp. no. | herbicide B | safener C |
|---|---|---|
| 1.742 | B.136 | C.3 |
| 1.743 | B.137 | C.3 |
| 1.744 | B.138 | C.3 |
| 1.745 | B.139 | C.3 |
| 1.746 | B.140 | C.3 |
| 1.747 | B.141 | C.3 |
| 1.748 | B.142 | C.3 |
| 1.749 | B.143 | C.3 |
| 1.750 | B.144 | C.3 |
| 1.751 | B.145 | C.3 |
| 1.752 | B.146 | C.3 |
| 1.753 | B.147 | C.3 |
| 1.754 | B.148 | C.3 |
| 1.755 | B.149 | C.3 |
| 1.756 | B.150 | C.3 |
| 1.757 | B.151 | C.3 |
| 1.758 | B.152 | C.3 |
| 1.759 | B.153 | C.3 |
| 1.760 | B.154 | C.3 |
| 1.761 | B.155 | C.3 |
| 1.762 | B.156 | C.3 |
| 1.763 | B.157 | C.3 |
| 1.764 | B.158 | C.3 |
| 1.765 | B.159 | C.3 |
| 1.766 | B.160 | C.3 |
| 1.767 | B.161 | C.3 |
| 1.768 | B.162 | C.3 |
| 1.769 | B.163 | C.3 |
| 1.770 | B.164 | C.3 |
| 1.771 | B.165 | C.3 |
| 1.772 | B.166 | C.3 |
| 1.773 | B.167 | C.3 |
| 1.774 | B.168 | C.3 |
| 1.775 | B.169 | C.3 |
| 1.776 | B.170 | C.3 |
| 1.777 | B.171 | C.3 |
| 1.778 | B.172 | C.3 |
| 1.779 | B.173 | C.3 |
| 1.780 | B.174 | C.3 |
| 1.781 | B.175 | C.3 |
| 1.782 | B.176 | C.3 |
| 1.783 | B.177 | C.3 |
| 1.784 | B.178 | C.3 |
| 1.785 | B.179 | C.3 |
| 1.786 | B.180 | C.3 |
| 1.787 | B.181 | C.3 |
| 1.788 | B.182 | C.3 |
| 1.789 | B.183 | C.3 |
| 1.790 | B.184 | C.3 |
| 1.791 | B.185 | C.3 |
| 1.792 | B.186 | C.3 |
| 1.793 | B.187 | C.3 |
| 1.794 | B.188 | C.3 |
| 1.795 | B.189 | C.3 |
| 1.796 | B.190 | C.3 |
| 1.797 | B.191 | C.3 |
| 1.798 | B.192 | C.3 |
| 1.799 | B.193 | C.3 |
| 1.800 | B.194 | C.3 |
| 1.801 | B.195 | C.3 |
| 1.802 | B.196 | C.3 |
| 1.803 | B.197 | C.3 |
| 1.804 | B.198 | C.3 |
| 1.805 | B.199 | C.3 |
| 1.806 | B.200 | C.3 |
| 1.807 | B.201 | C.3 |
| 1.808 | B.202 | C.3 |
| 1.809 | B.1 | C.4 |
| 1.810 | B.2 | C.4 |
| 1.811 | B.3 | C.4 |
| 1.812 | B.4 | C.4 |
| 1.813 | B.5 | C.4 |
| 1.814 | B.6 | C.4 |
| 1.815 | B.7 | C.4 |
| 1.816 | B.8 | C.4 |
| 1.817 | B.9 | C.4 |
| 1.818 | B.10 | C.4 |
| 1.819 | B.11 | C.4 |
| 1.820 | B.12 | C.4 |
| 1.821 | B.13 | C.4 |
| 1.822 | B.14 | C.4 |
| 1.823 | B.15 | C.4 |
| 1.824 | B.16 | C.4 |
| 1.825 | B.17 | C.4 |
| 1.826 | B.18 | C.4 |
| 1.827 | B.19 | C.4 |
| 1.828 | B.20 | C.4 |
| 1.829 | B.21 | C.4 |
| 1.830 | B.22 | C.4 |
| 1.831 | B.23 | C.4 |
| 1.832 | B.24 | C.4 |
| 1.833 | B.25 | C.4 |
| 1.834 | B.26 | C.4 |
| 1.835 | B.27 | C.4 |
| 1.836 | B.28 | C.4 |
| 1.837 | B.29 | C.4 |
| 1.838 | B.30 | C.4 |
| 1.839 | B.31 | C.4 |
| 1.840 | B.32 | C.4 |
| 1.841 | B.33 | C.4 |
| 1.842 | B.34 | C.4 |
| 1.843 | B.35 | C.4 |
| 1.844 | B.36 | C.4 |
| 1.845 | B.37 | C.4 |
| 1.846 | B.38 | C.4 |
| 1.847 | B.39 | C.4 |
| 1.848 | B.40 | C.4 |
| 1.849 | B.41 | C.4 |
| 1.850 | B.42 | C.4 |
| 1.851 | B.43 | C.4 |
| 1.852 | B.44 | C.4 |
| 1.853 | B.45 | C.4 |
| 1.854 | B.46 | C.4 |
| 1.855 | B.47 | C.4 |
| 1.856 | B.48 | C.4 |
| 1.857 | B.49 | C.4 |
| 1.858 | B.50 | C.4 |
| 1.859 | B.51 | C.4 |
| 1.860 | B.52 | C.4 |
| 1.861 | B.53 | C.4 |
| 1.862 | B.54 | C.4 |
| 1.863 | B.55 | C.4 |
| 1.864 | B.56 | C.4 |
| 1.865 | B.57 | C.4 |
| 1.866 | B.58 | C.4 |
| 1.867 | B.59 | C.4 |
| 1.868 | B.60 | C.4 |
| 1.869 | B.61 | C.4 |
| 1.870 | B.62 | C.4 |
| 1.871 | B.63 | C.4 |
| 1.872 | B.64 | C.4 |
| 1.873 | B.65 | C.4 |
| 1.874 | B.66 | C.4 |
| 1.875 | B.67 | C.4 |
| 1.876 | B.68 | C.4 |
| 1.877 | B.69 | C.4 |
| 1.878 | B.70 | C.4 |
| 1.879 | B.71 | C.4 |
| 1.880 | B.72 | C.4 |
| 1.881 | B.73 | C.4 |
| 1.882 | B.74 | C.4 |
| 1.883 | B.75 | C.4 |
| 1.884 | B.76 | C.4 |
| 1.885 | B.77 | C.4 |
| 1.886 | B.78 | C.4 |
| 1.887 | B.79 | C.4 |
| 1.888 | B.80 | C.4 |
| 1.889 | B.81 | C.4 |
| 1.890 | B.82 | C.4 |
| 1.891 | B.83 | C.4 |
| 1.892 | B.84 | C.4 |
| 1.893 | B.85 | C.4 |

TABLE 1-continued (compositions 1.1 to 1.3653):

| comp. no. | herbicide B | safener C |
|---|---|---|
| 1.894 | B.86 | C.4 |
| 1.895 | B.87 | C.4 |
| 1.896 | B.88 | C.4 |
| 1.897 | B.89 | C.4 |
| 1.898 | B.90 | C.4 |
| 1.899 | B.91 | C.4 |
| 1.900 | B.92 | C.4 |
| 1.901 | B.93 | C.4 |
| 1.902 | B.94 | C.4 |
| 1.903 | B.95 | C.4 |
| 1.904 | B.96 | C.4 |
| 1.905 | B.97 | C.4 |
| 1.906 | B.98 | C.4 |
| 1.907 | B.99 | C.4 |
| 1.908 | B.100 | C.4 |
| 1.909 | B.101 | C.4 |
| 1.910 | B.102 | C.4 |
| 1.911 | B.103 | C.4 |
| 1.912 | B.104 | C.4 |
| 1.913 | B.105 | C.4 |
| 1.914 | B.106 | C.4 |
| 1.915 | B.107 | C.4 |
| 1.916 | B.108 | C.4 |
| 1.917 | B.109 | C.4 |
| 1.918 | B.110 | C.4 |
| 1.919 | B.111 | C.4 |
| 1.920 | B.112 | C.4 |
| 1.921 | B.113 | C.4 |
| 1.922 | B.114 | C.4 |
| 1.923 | B.115 | C.4 |
| 1.924 | B.116 | C.4 |
| 1.925 | B.117 | C.4 |
| 1.926 | B.118 | C.4 |
| 1.927 | B.119 | C.4 |
| 1.928 | B.120 | C.4 |
| 1.929 | B.121 | C.4 |
| 1.930 | B.122 | C.4 |
| 1.931 | B.123 | C.4 |
| 1.932 | B.124 | C.4 |
| 1.933 | B.125 | C.4 |
| 1.934 | B.126 | C.4 |
| 1.935 | B.127 | C.4 |
| 1.936 | B.128 | C.4 |
| 1.937 | B.129 | C.4 |
| 1.938 | B.130 | C.4 |
| 1.939 | B.131 | C.4 |
| 1.940 | B.132 | C.4 |
| 1.941 | B.133 | C.4 |
| 1.942 | B.134 | C.4 |
| 1.943 | B.135 | C.4 |
| 1.944 | B.136 | C.4 |
| 1.945 | B.137 | C.4 |
| 1.946 | B.138 | C.4 |
| 1.947 | B.139 | C.4 |
| 1.948 | B.140 | C.4 |
| 1.949 | B.141 | C.4 |
| 1.950 | B.142 | C.4 |
| 1.951 | B.143 | C.4 |
| 1.952 | B.144 | C.4 |
| 1.953 | B.145 | C.4 |
| 1.954 | B.146 | C.4 |
| 1.955 | B.147 | C.4 |
| 1.956 | B.148 | C.4 |
| 1.957 | B.149 | C.4 |
| 1.958 | B.150 | C.4 |
| 1.959 | B.151 | C.4 |
| 1.960 | B.152 | C.4 |
| 1.961 | B.153 | C.4 |
| 1.962 | B.154 | C.4 |
| 1.963 | B.155 | C.4 |
| 1.964 | B.156 | C.4 |
| 1.965 | B.157 | C.4 |
| 1.966 | B.158 | C.4 |
| 1.967 | B.159 | C.4 |
| 1.968 | B.160 | C.4 |
| 1.969 | B.161 | C.4 |
| 1.970 | B.162 | C.4 |
| 1.971 | B.163 | C.4 |
| 1.972 | B.164 | C.4 |
| 1.973 | B.165 | C.4 |
| 1.974 | B.166 | C.4 |
| 1.975 | B.167 | C.4 |
| 1.976 | B.168 | C.4 |
| 1.977 | B.169 | C.4 |
| 1.978 | B.170 | C.4 |
| 1.979 | B.171 | C.4 |
| 1.980 | B.172 | C.4 |
| 1.981 | B.173 | C.4 |
| 1.982 | B.174 | C.4 |
| 1.983 | B.175 | C.4 |
| 1.984 | B.176 | C.4 |
| 1.985 | B.177 | C.4 |
| 1.986 | B.178 | C.4 |
| 1.987 | B.179 | C.4 |
| 1.988 | B.180 | C.4 |
| 1.989 | B.181 | C.4 |
| 1.990 | B.182 | C.4 |
| 1.991 | B.183 | C.4 |
| 1.992 | B.184 | C.4 |
| 1.993 | B.185 | C.4 |
| 1.994 | B.186 | C.4 |
| 1.995 | B.187 | C.4 |
| 1.996 | B.188 | C.4 |
| 1.997 | B.189 | C.4 |
| 1.998 | B.190 | C.4 |
| 1.999 | B.191 | C.4 |
| 1.1000 | B.192 | C.4 |
| 1.1001 | B.193 | C.4 |
| 1.1002 | B.194 | C.4 |
| 1.1003 | B.195 | C.4 |
| 1.1004 | B.196 | C.4 |
| 1.1005 | B.197 | C.4 |
| 1.1006 | B.198 | C.4 |
| 1.1007 | B.199 | C.4 |
| 1.1008 | B.200 | C.4 |
| 1.1009 | B.201 | C.4 |
| 1.1010 | B.202 | C.4 |
| 1.1011 | B.1 | C.5 |
| 1.1012 | B.2 | C.5 |
| 1.1013 | B.3 | C.5 |
| 1.1014 | B.4 | C.5 |
| 1.1015 | B.5 | C.5 |
| 1.1016 | B.6 | C.5 |
| 1.1017 | B.7 | C.5 |
| 1.1018 | B.8 | C.5 |
| 1.1019 | B.9 | C.5 |
| 1.1020 | B.10 | C.5 |
| 1.1021 | B.11 | C.5 |
| 1.1022 | B.12 | C.5 |
| 1.1023 | B.13 | C.5 |
| 1.1024 | B.14 | C.5 |
| 1.1025 | B.15 | C.5 |
| 1.1026 | B.16 | C.5 |
| 1.1027 | B.17 | C.5 |
| 1.1028 | B.18 | C.5 |
| 1.1029 | B.19 | C.5 |
| 1.1030 | B.20 | C.5 |
| 1.1031 | B.21 | C.5 |
| 1.1032 | B.22 | C.5 |
| 1.1033 | B.23 | C.5 |
| 1.1034 | B.24 | C.5 |
| 1.1035 | B.25 | C.5 |
| 1.1036 | B.26 | C.5 |
| 1.1037 | B.27 | C.5 |
| 1.1038 | B.28 | C.5 |
| 1.1039 | B.29 | C.5 |
| 1.1040 | B.30 | C.5 |
| 1.1041 | B.31 | C.5 |
| 1.1042 | B.32 | C.5 |
| 1.1043 | B.33 | C.5 |
| 1.1044 | B.34 | C.5 |
| 1.1045 | B.35 | C.5 |

TABLE 1-continued (compositions 1.1 to 1.3653):

| comp. no. | herbicide B | safener C |
|---|---|---|
| 1.1046 | B.36 | C.5 |
| 1.1047 | B.37 | C.5 |
| 1.1048 | B.38 | C.5 |
| 1.1049 | B.39 | C.5 |
| 1.1050 | B.40 | C.5 |
| 1.1051 | B.41 | C.5 |
| 1.1052 | B.42 | C.5 |
| 1.1053 | B.43 | C.5 |
| 1.1054 | B.44 | C.5 |
| 1.1055 | B.45 | C.5 |
| 1.1056 | B.46 | C.5 |
| 1.1057 | B.47 | C.5 |
| 1.1058 | B.48 | C.5 |
| 1.1059 | B.49 | C.5 |
| 1.1060 | B.50 | C.5 |
| 1.1061 | B.51 | C.5 |
| 1.1062 | B.52 | C.5 |
| 1.1063 | B.53 | C.5 |
| 1.1064 | B.54 | C.5 |
| 1.1065 | B.55 | C.5 |
| 1.1066 | B.56 | C.5 |
| 1.1067 | B.57 | C.5 |
| 1.1068 | B.58 | C.5 |
| 1.1069 | B.59 | C.5 |
| 1.1070 | B.60 | C.5 |
| 1.1071 | B.61 | C.5 |
| 1.1072 | B.62 | C.5 |
| 1.1073 | B.63 | C.5 |
| 1.1074 | B.64 | C.5 |
| 1.1075 | B.65 | C.5 |
| 1.1076 | B.66 | C.5 |
| 1.1077 | B.67 | C.5 |
| 1.1078 | B.68 | C.5 |
| 1.1079 | B.69 | C.5 |
| 1.1080 | B.70 | C.5 |
| 1.1081 | B.71 | C.5 |
| 1.1082 | B.72 | C.5 |
| 1.1083 | B.73 | C.5 |
| 1.1084 | B.74 | C.5 |
| 1.1085 | B.75 | C.5 |
| 1.1086 | B.76 | C.5 |
| 1.1087 | B.77 | C.5 |
| 1.1088 | B.78 | C.5 |
| 1.1089 | B.79 | C.5 |
| 1.1090 | B.80 | C.5 |
| 1.1091 | B.81 | C.5 |
| 1.1092 | B.82 | C.5 |
| 1.1093 | B.83 | C.5 |
| 1.1094 | B.84 | C.5 |
| 1.1095 | B.85 | C.5 |
| 1.1096 | B.86 | C.5 |
| 1.1097 | B.87 | C.5 |
| 1.1098 | B.88 | C.5 |
| 1.1099 | B.89 | C.5 |
| 1.1100 | B.90 | C.5 |
| 1.1101 | B.91 | C.5 |
| 1.1102 | B.92 | C.5 |
| 1.1103 | B.93 | C.5 |
| 1.1104 | B.94 | C.5 |
| 1.1105 | B.95 | C.5 |
| 1.1106 | B.96 | C.5 |
| 1.1107 | B.97 | C.5 |
| 1.1108 | B.98 | C.5 |
| 1.1109 | B.99 | C.5 |
| 1.1110 | B.100 | C.5 |
| 1.1111 | B.101 | C.5 |
| 1.1112 | B.102 | C.5 |
| 1.1113 | B.103 | C.5 |
| 1.1114 | B.104 | C.5 |
| 1.1115 | B.105 | C.5 |
| 1.1116 | B.106 | C.5 |
| 1.1117 | B.107 | C.5 |
| 1.1118 | B.108 | C.5 |
| 1.1119 | B.109 | C.5 |
| 1.1120 | B.110 | C.5 |
| 1.1121 | B.111 | C.5 |
| 1.1122 | B.112 | C.5 |
| 1.1123 | B.113 | C.5 |
| 1.1124 | B.114 | C.5 |
| 1.1125 | B.115 | C.5 |
| 1.1126 | B.116 | C.5 |
| 1.1127 | B.117 | C.5 |
| 1.1128 | B.118 | C.5 |
| 1.1129 | B.119 | C.5 |
| 1.1130 | B.120 | C.5 |
| 1.1131 | B.121 | C.5 |
| 1.1132 | B.122 | C.5 |
| 1.1133 | B.123 | C.5 |
| 1.1134 | B.124 | C.5 |
| 1.1135 | B.125 | C.5 |
| 1.1136 | B.126 | C.5 |
| 1.1137 | B.127 | C.5 |
| 1.1138 | B.128 | C.5 |
| 1.1139 | B.129 | C.5 |
| 1.1140 | B.130 | C.5 |
| 1.1141 | B.131 | C.5 |
| 1.1142 | B.132 | C.5 |
| 1.1143 | B.133 | C.5 |
| 1.1144 | B.134 | C.5 |
| 1.1145 | B.135 | C.5 |
| 1.1146 | B.136 | C.5 |
| 1.1147 | B.137 | C.5 |
| 1.1148 | B.138 | C.5 |
| 1.1149 | B.139 | C.5 |
| 1.1150 | B.140 | C.5 |
| 1.1151 | B.141 | C.5 |
| 1.1152 | B.142 | C.5 |
| 1.1153 | B.143 | C.5 |
| 1.1154 | B.144 | C.5 |
| 1.1155 | B.145 | C.5 |
| 1.1156 | B.146 | C.5 |
| 1.1157 | B.147 | C.5 |
| 1.1158 | B.148 | C.5 |
| 1.1159 | B.149 | C.5 |
| 1.1160 | B.150 | C.5 |
| 1.1161 | B.151 | C.5 |
| 1.1162 | B.152 | C.5 |
| 1.1163 | B.153 | C.5 |
| 1.1164 | B.154 | C.5 |
| 1.1165 | B.155 | C.5 |
| 1.1166 | B.156 | C.5 |
| 1.1167 | B.157 | C.5 |
| 1.1168 | B.158 | C.5 |
| 1.1169 | B.159 | C.5 |
| 1.1170 | B.160 | C.5 |
| 1.1171 | B.161 | C.5 |
| 1.1172 | B.162 | C.5 |
| 1.1173 | B.163 | C.5 |
| 1.1174 | B.164 | C.5 |
| 1.1175 | B.165 | C.5 |
| 1.1176 | B.166 | C.5 |
| 1.1177 | B.167 | C.5 |
| 1.1178 | B.168 | C.5 |
| 1.1179 | B.169 | C.5 |
| 1.1180 | B.170 | C.5 |
| 1.1181 | B.171 | C.5 |
| 1.1182 | B.172 | C.5 |
| 1.1183 | B.173 | C.5 |
| 1.1184 | B.174 | C.5 |
| 1.1185 | B.175 | C.5 |
| 1.1186 | B.176 | C.5 |
| 1.1187 | B.177 | C.5 |
| 1.1188 | B.178 | C.5 |
| 1.1189 | B.179 | C.5 |
| 1.1190 | B.180 | C.5 |
| 1.1191 | B.181 | C.5 |
| 1.1192 | B.182 | C.5 |
| 1.1193 | B.183 | C.5 |
| 1.1194 | B.184 | C.5 |
| 1.1195 | B.185 | C.5 |
| 1.1196 | B.186 | C.5 |
| 1.1197 | B.187 | C.5 |

TABLE 1-continued (compositions 1.1 to 1.3653):

| comp. no. | herbicide B | safener C |
|---|---|---|
| 1.1198 | B.188 | C.5 |
| 1.1199 | B.189 | C.5 |
| 1.1200 | B.190 | C.5 |
| 1.1201 | B.191 | C.5 |
| 1.1202 | B.192 | C.5 |
| 1.1203 | B.193 | C.5 |
| 1.1204 | B.194 | C.5 |
| 1.1205 | B.195 | C.5 |
| 1.1206 | B.196 | C.5 |
| 1.1207 | B.197 | C.5 |
| 1.1208 | B.198 | C.5 |
| 1.1209 | B.199 | C.5 |
| 1.1210 | B.200 | C.5 |
| 1.1211 | B.201 | C.5 |
| 1.1212 | B.202 | C.5 |
| 1.1213 | B.1 | C.6 |
| 1.1214 | B.2 | C.6 |
| 1.1215 | B.3 | C.6 |
| 1.1216 | B.4 | C.6 |
| 1.1217 | B.5 | C.6 |
| 1.1218 | B.6 | C.6 |
| 1.1219 | B.7 | C.6 |
| 1.1220 | B.8 | C.6 |
| 1.1221 | B.9 | C.6 |
| 1.1222 | B.10 | C.6 |
| 1.1223 | B.11 | C.6 |
| 1.1224 | B.12 | C.6 |
| 1.1225 | B.13 | C.6 |
| 1.1226 | B.14 | C.6 |
| 1.1227 | B.15 | C.6 |
| 1.1228 | B.16 | C.6 |
| 1.1229 | B.17 | C.6 |
| 1.1230 | B.18 | C.6 |
| 1.1231 | B.19 | C.6 |
| 1.1232 | B.20 | C.6 |
| 1.1233 | B.21 | C.6 |
| 1.1234 | B.22 | C.6 |
| 1.1235 | B.23 | C.6 |
| 1.1236 | B.24 | C.6 |
| 1.1237 | B.25 | C.6 |
| 1.1238 | B.26 | C.6 |
| 1.1239 | B.27 | C.6 |
| 1.1240 | B.28 | C.6 |
| 1.1241 | B.29 | C.6 |
| 1.1242 | B.30 | C.6 |
| 1.1243 | B.31 | C.6 |
| 1.1244 | B.32 | C.6 |
| 1.1245 | B.33 | C.6 |
| 1.1246 | B.34 | C.6 |
| 1.1247 | B.35 | C.6 |
| 1.1248 | B.36 | C.6 |
| 1.1249 | B.37 | C.6 |
| 1.1250 | B.38 | C.6 |
| 1.1251 | B.39 | C.6 |
| 1.1252 | B.40 | C.6 |
| 1.1253 | B.41 | C.6 |
| 1.1254 | B.42 | C.6 |
| 1.1255 | B.43 | C.6 |
| 1.1256 | B.44 | C.6 |
| 1.1257 | B.45 | C.6 |
| 1.1258 | B.46 | C.6 |
| 1.1259 | B.47 | C.6 |
| 1.1260 | B.48 | C.6 |
| 1.1261 | B.49 | C.6 |
| 1.1262 | B.50 | C.6 |
| 1.1263 | B.51 | C.6 |
| 1.1264 | B.52 | C.6 |
| 1.1265 | B.53 | C.6 |
| 1.1266 | B.54 | C.6 |
| 1.1267 | B.55 | C.6 |
| 1.1268 | B.56 | C.6 |
| 1.1269 | B.57 | C.6 |
| 1.1270 | B.58 | C.6 |
| 1.1271 | B.59 | C.6 |
| 1.1272 | B.60 | C.6 |
| 1.1273 | B.61 | C.6 |
| 1.1274 | B.62 | C.6 |
| 1.1275 | B.63 | C.6 |
| 1.1276 | B.64 | C.6 |
| 1.1277 | B.65 | C.6 |
| 1.1278 | B.66 | C.6 |
| 1.1279 | B.67 | C.6 |
| 1.1280 | B.68 | C.6 |
| 1.1281 | B.69 | C.6 |
| 1.1282 | B.70 | C.6 |
| 1.1283 | B.71 | C.6 |
| 1.1284 | B.72 | C.6 |
| 1.1285 | B.73 | C.6 |
| 1.1286 | B.74 | C.6 |
| 1.1287 | B.75 | C.6 |
| 1.1288 | B.76 | C.6 |
| 1.1289 | B.77 | C.6 |
| 1.1290 | B.78 | C.6 |
| 1.1291 | B.79 | C.6 |
| 1.1292 | B.80 | C.6 |
| 1.1293 | B.81 | C.6 |
| 1.1294 | B.82 | C.6 |
| 1.1295 | B.83 | C.6 |
| 1.1296 | B.84 | C.6 |
| 1.1297 | B.85 | C.6 |
| 1.1298 | B.86 | C.6 |
| 1.1299 | B.87 | C.6 |
| 1.1300 | B.88 | C.6 |
| 1.1301 | B.89 | C.6 |
| 1.1302 | B.90 | C.6 |
| 1.1303 | B.91 | C.6 |
| 1.1304 | B.92 | C.6 |
| 1.1305 | B.93 | C.6 |
| 1.1306 | B.94 | C.6 |
| 1.1307 | B.95 | C.6 |
| 1.1308 | B.96 | C.6 |
| 1.1309 | B.97 | C.6 |
| 1.1310 | B.98 | C.6 |
| 1.1311 | B.99 | C.6 |
| 1.1312 | B.100 | C.6 |
| 1.1313 | B.101 | C.6 |
| 1.1314 | B.102 | C.6 |
| 1.1315 | B.103 | C.6 |
| 1.1316 | B.104 | C.6 |
| 1.1317 | B.105 | C.6 |
| 1.1318 | B.106 | C.6 |
| 1.1319 | B.107 | C.6 |
| 1.1320 | B.108 | C.6 |
| 1.1321 | B.109 | C.6 |
| 1.1322 | B.110 | C.6 |
| 1.1323 | B.111 | C.6 |
| 1.1324 | B.112 | C.6 |
| 1.1325 | B.113 | C.6 |
| 1.1326 | B.114 | C.6 |
| 1.1327 | B.115 | C.6 |
| 1.1328 | B.116 | C.6 |
| 1.1329 | B.117 | C.6 |
| 1.1330 | B.118 | C.6 |
| 1.1331 | B.119 | C.6 |
| 1.1332 | B.120 | C.6 |
| 1.1333 | B.121 | C.6 |
| 1.1334 | B.122 | C.6 |
| 1.1335 | B.123 | C.6 |
| 1.1336 | B.124 | C.6 |
| 1.1337 | B.125 | C.6 |
| 1.1338 | B.126 | C.6 |
| 1.1339 | B.127 | C.6 |
| 1.1340 | B.128 | C.6 |
| 1.1341 | B.129 | C.6 |
| 1.1342 | B.130 | C.6 |
| 1.1343 | B.131 | C.6 |
| 1.1344 | B.132 | C.6 |
| 1.1345 | B.133 | C.6 |
| 1.1346 | B.134 | C.6 |
| 1.1347 | B.135 | C.6 |
| 1.1348 | B.136 | C.6 |
| 1.1349 | B.137 | C.6 |

TABLE 1-continued (compositions 1.1 to 1.3653):

| comp. no. | herbicide B | safener C |
|---|---|---|
| 1.1350 | B.138 | C.6 |
| 1.1351 | B.139 | C.6 |
| 1.1352 | B.140 | C.6 |
| 1.1353 | B.141 | C.6 |
| 1.1354 | B.142 | C.6 |
| 1.1355 | B.143 | C.6 |
| 1.1356 | B.144 | C.6 |
| 1.1357 | B.145 | C.6 |
| 1.1358 | B.146 | C.6 |
| 1.1359 | B.147 | C.6 |
| 1.1360 | B.148 | C.6 |
| 1.1361 | B.149 | C.6 |
| 1.1362 | B.150 | C.6 |
| 1.1363 | B.151 | C.6 |
| 1.1364 | B.152 | C.6 |
| 1.1365 | B.153 | C.6 |
| 1.1366 | B.154 | C.6 |
| 1.1367 | B.155 | C.6 |
| 1.1368 | B.156 | C.6 |
| 1.1369 | B.157 | C.6 |
| 1.1370 | B.158 | C.6 |
| 1.1371 | B.159 | C.6 |
| 1.1372 | B.160 | C.6 |
| 1.1373 | B.161 | C.6 |
| 1.1374 | B.162 | C.6 |
| 1.1375 | B.163 | C.6 |
| 1.1376 | B.164 | C.6 |
| 1.1377 | B.165 | C.6 |
| 1.1378 | B.166 | C.6 |
| 1.1379 | B.167 | C.6 |
| 1.1380 | B.168 | C.6 |
| 1.1381 | B.169 | C.6 |
| 1.1382 | B.170 | C.6 |
| 1.1383 | B.171 | C.6 |
| 1.1384 | B.172 | C.6 |
| 1.1385 | B.173 | C.6 |
| 1.1386 | B.174 | C.6 |
| 1.1387 | B.175 | C.6 |
| 1.1388 | B.176 | C.6 |
| 1.1389 | B.177 | C.6 |
| 1.1390 | B.178 | C.6 |
| 1.1391 | B.179 | C.6 |
| 1.1392 | B.180 | C.6 |
| 1.1393 | B.181 | C.6 |
| 1.1394 | B.182 | C.6 |
| 1.1395 | B.183 | C.6 |
| 1.1396 | B.184 | C.6 |
| 1.1397 | B.185 | C.6 |
| 1.1398 | B.186 | C.6 |
| 1.1399 | B.187 | C.6 |
| 1.1400 | B.188 | C.6 |
| 1.1401 | B.189 | C.6 |
| 1.1402 | B.190 | C.6 |
| 1.1403 | B.191 | C.6 |
| 1.1404 | B.192 | C.6 |
| 1.1405 | B.193 | C.6 |
| 1.1406 | B.194 | C.6 |
| 1.1407 | B.195 | C.6 |
| 1.1408 | B.196 | C.6 |
| 1.1409 | B.197 | C.6 |
| 1.1410 | B.198 | C.6 |
| 1.1411 | B.199 | C.6 |
| 1.1412 | B.200 | C.6 |
| 1.1413 | B.201 | C.6 |
| 1.1414 | B.202 | C.6 |
| 1.1415 | B.1 | C.7 |
| 1.1416 | B.2 | C.7 |
| 1.1417 | B.3 | C.7 |
| 1.1418 | B.4 | C.7 |
| 1.1419 | B.5 | C.7 |
| 1.1420 | B.6 | C.7 |
| 1.1421 | B.7 | C.7 |
| 1.1422 | B.8 | C.7 |
| 1.1423 | B.9 | C.7 |
| 1.1424 | B.10 | C.7 |
| 1.1425 | B.11 | C.7 |
| 1.1426 | B.12 | C.7 |
| 1.1427 | B.13 | C.7 |
| 1.1428 | B.14 | C.7 |
| 1.1429 | B.15 | C.7 |
| 1.1430 | B.16 | C.7 |
| 1.1431 | B.17 | C.7 |
| 1.1432 | B.18 | C.7 |
| 1.1433 | B.19 | C.7 |
| 1.1434 | B.20 | C.7 |
| 1.1435 | B.21 | C.7 |
| 1.1436 | B.22 | C.7 |
| 1.1437 | B.23 | C.7 |
| 1.1438 | B.24 | C.7 |
| 1.1439 | B.25 | C.7 |
| 1.1440 | B.26 | C.7 |
| 1.1441 | B.27 | C.7 |
| 1.1442 | B.28 | C.7 |
| 1.1443 | B.29 | C.7 |
| 1.1444 | B.30 | C.7 |
| 1.1445 | B.31 | C.7 |
| 1.1446 | B.32 | C.7 |
| 1.1447 | B.33 | C.7 |
| 1.1448 | B.34 | C.7 |
| 1.1449 | B.35 | C.7 |
| 1.1450 | B.36 | C.7 |
| 1.1451 | B.37 | C.7 |
| 1.1452 | B.38 | C.7 |
| 1.1453 | B.39 | C.7 |
| 1.1454 | B.40 | C.7 |
| 1.1455 | B.41 | C.7 |
| 1.1456 | B.42 | C.7 |
| 1.1457 | B.43 | C.7 |
| 1.1458 | B.44 | C.7 |
| 1.1459 | B.45 | C.7 |
| 1.1460 | B.46 | C.7 |
| 1.1461 | B.47 | C.7 |
| 1.1462 | B.48 | C.7 |
| 1.1463 | B.49 | C.7 |
| 1.1464 | B.50 | C.7 |
| 1.1465 | B.51 | C.7 |
| 1.1466 | B.52 | C.7 |
| 1.1467 | B.53 | C.7 |
| 1.1468 | B.54 | C.7 |
| 1.1469 | B.55 | C.7 |
| 1.1470 | B.56 | C.7 |
| 1.1471 | B.57 | C.7 |
| 1.1472 | B.58 | C.7 |
| 1.1473 | B.59 | C.7 |
| 1.1474 | B.60 | C.7 |
| 1.1475 | B.61 | C.7 |
| 1.1476 | B.62 | C.7 |
| 1.1477 | B.63 | C.7 |
| 1.1478 | B.64 | C.7 |
| 1.1479 | B.65 | C.7 |
| 1.1480 | B.66 | C.7 |
| 1.1481 | B.67 | C.7 |
| 1.1482 | B.68 | C.7 |
| 1.1483 | B.69 | C.7 |
| 1.1484 | B.70 | C.7 |
| 1.1485 | B.71 | C.7 |
| 1.1486 | B.72 | C.7 |
| 1.1487 | B.73 | C.7 |
| 1.1488 | B.74 | C.7 |
| 1.1489 | B.75 | C.7 |
| 1.1490 | B.76 | C.7 |
| 1.1491 | B.77 | C.7 |
| 1.1492 | B.78 | C.7 |
| 1.1493 | B.79 | C.7 |
| 1.1494 | B.80 | C.7 |
| 1.1495 | B.81 | C.7 |
| 1.1496 | B.82 | C.7 |
| 1.1497 | B.83 | C.7 |
| 1.1498 | B.84 | C.7 |
| 1.1499 | B.85 | C.7 |
| 1.1500 | B.86 | C.7 |
| 1.1501 | B.87 | C.7 |

TABLE 1-continued (compositions 1.1 to 1.3653):

| comp. no. | herbicide B | safener C |
|---|---|---|
| 1.1502 | B.88 | C.7 |
| 1.1503 | B.89 | C.7 |
| 1.1504 | B.90 | C.7 |
| 1.1505 | B.91 | C.7 |
| 1.1506 | B.92 | C.7 |
| 1.1507 | B.93 | C.7 |
| 1.1508 | B.94 | C.7 |
| 1.1509 | B.95 | C.7 |
| 1.1510 | B.96 | C.7 |
| 1.1511 | B.97 | C.7 |
| 1.1512 | B.98 | C.7 |
| 1.1513 | B.99 | C.7 |
| 1.1514 | B.100 | C.7 |
| 1.1515 | B.101 | C.7 |
| 1.1516 | B.102 | C.7 |
| 1.1517 | B.103 | C.7 |
| 1.1518 | B.104 | C.7 |
| 1.1519 | B.105 | C.7 |
| 1.1520 | B.106 | C.7 |
| 1.1521 | B.107 | C.7 |
| 1.1522 | B.108 | C.7 |
| 1.1523 | B.109 | C.7 |
| 1.1524 | B.110 | C.7 |
| 1.1525 | B.111 | C.7 |
| 1.1526 | B.112 | C.7 |
| 1.1527 | B.113 | C.7 |
| 1.1528 | B.114 | C.7 |
| 1.1529 | B.115 | C.7 |
| 1.1530 | B.116 | C.7 |
| 1.1531 | B.117 | C.7 |
| 1.1532 | B.118 | C.7 |
| 1.1533 | B.119 | C.7 |
| 1.1534 | B.120 | C.7 |
| 1.1535 | B.121 | C.7 |
| 1.1536 | B.122 | C.7 |
| 1.1537 | B.123 | C.7 |
| 1.1538 | B.124 | C.7 |
| 1.1539 | B.125 | C.7 |
| 1.1540 | B.126 | C.7 |
| 1.1541 | B.127 | C.7 |
| 1.1542 | B.128 | C.7 |
| 1.1543 | B.129 | C.7 |
| 1.1544 | B.130 | C.7 |
| 1.1545 | B.131 | C.7 |
| 1.1546 | B.132 | C.7 |
| 1.1547 | B.133 | C.7 |
| 1.1548 | B.134 | C.7 |
| 1.1549 | B.135 | C.7 |
| 1.1550 | B.136 | C.7 |
| 1.1551 | B.137 | C.7 |
| 1.1552 | B.138 | C.7 |
| 1.1553 | B.139 | C.7 |
| 1.1554 | B.140 | C.7 |
| 1.1555 | B.141 | C.7 |
| 1.1556 | B.142 | C.7 |
| 1.1557 | B.143 | C.7 |
| 1.1558 | B.144 | C.7 |
| 1.1559 | B.145 | C.7 |
| 1.1560 | B.146 | C.7 |
| 1.1561 | B.147 | C.7 |
| 1.1562 | B.148 | C.7 |
| 1.1563 | B.149 | C.7 |
| 1.1564 | B.150 | C.7 |
| 1.1565 | B.151 | C.7 |
| 1.1566 | B.152 | C.7 |
| 1.1567 | B.153 | C.7 |
| 1.1568 | B.154 | C.7 |
| 1.1569 | B.155 | C.7 |
| 1.1570 | B.156 | C.7 |
| 1.1571 | B.157 | C.7 |
| 1.1572 | B.158 | C.7 |
| 1.1573 | B.159 | C.7 |
| 1.1574 | B.160 | C.7 |
| 1.1575 | B.161 | C.7 |
| 1.1576 | B.162 | C.7 |
| 1.1577 | B.163 | C.7 |
| 1.1578 | B.164 | C.7 |
| 1.1579 | B.165 | C.7 |
| 1.1580 | B.166 | C.7 |
| 1.1581 | B.167 | C.7 |
| 1.1582 | B.168 | C.7 |
| 1.1583 | B.169 | C.7 |
| 1.1584 | B.170 | C.7 |
| 1.1585 | B.171 | C.7 |
| 1.1586 | B.172 | C.7 |
| 1.1587 | B.173 | C.7 |
| 1.1588 | B.174 | C.7 |
| 1.1589 | B.175 | C.7 |
| 1.1590 | B.176 | C.7 |
| 1.1591 | B.177 | C.7 |
| 1.1592 | B.178 | C.7 |
| 1.1593 | B.179 | C.7 |
| 1.1594 | B.180 | C.7 |
| 1.1595 | B.181 | C.7 |
| 1.1596 | B.182 | C.7 |
| 1.1597 | B.183 | C.7 |
| 1.1598 | B.184 | C.7 |
| 1.1599 | B.185 | C.7 |
| 1.1600 | B.186 | C.7 |
| 1.1601 | B.187 | C.7 |
| 1.1602 | B.188 | C.7 |
| 1.1603 | B.189 | C.7 |
| 1.1604 | B.190 | C.7 |
| 1.1605 | B.191 | C.7 |
| 1.1606 | B.192 | C.7 |
| 1.1607 | B.193 | C.7 |
| 1.1608 | B.194 | C.7 |
| 1.1609 | B.195 | C.7 |
| 1.1610 | B.196 | C.7 |
| 1.1611 | B.197 | C.7 |
| 1.1612 | B.198 | C.7 |
| 1.1613 | B.199 | C.7 |
| 1.1614 | B.200 | C.7 |
| 1.1615 | B.201 | C.7 |
| 1.1616 | B.202 | C.7 |
| 1.1617 | B.1 | C.8 |
| 1.1618 | B.2 | C.8 |
| 1.1619 | B.3 | C.8 |
| 1.1620 | B.4 | C.8 |
| 1.1621 | B.5 | C.8 |
| 1.1622 | B.6 | C.8 |
| 1.1623 | B.7 | C.8 |
| 1.1624 | B.8 | C.8 |
| 1.1625 | B.9 | C.8 |
| 1.1626 | B.10 | C.8 |
| 1.1627 | B.11 | C.8 |
| 1.1628 | B.12 | C.8 |
| 1.1629 | B.13 | C.8 |
| 1.1630 | B.14 | C.8 |
| 1.1631 | B.15 | C.8 |
| 1.1632 | B.16 | C.8 |
| 1.1633 | B.17 | C.8 |
| 1.1634 | B.18 | C.8 |
| 1.1635 | B.19 | C.8 |
| 1.1636 | B.20 | C.8 |
| 1.1637 | B.21 | C.8 |
| 1.1638 | B.22 | C.8 |
| 1.1639 | B.23 | C.8 |
| 1.1640 | B.24 | C.8 |
| 1.1641 | B.25 | C.8 |
| 1.1642 | B.26 | C.8 |
| 1.1643 | B.27 | C.8 |
| 1.1644 | B.28 | C.8 |
| 1.1645 | B.29 | C.8 |
| 1.1646 | B.30 | C.8 |
| 1.1647 | B.31 | C.8 |
| 1.1648 | B.32 | C.8 |
| 1.1649 | B.33 | C.8 |
| 1.1650 | B.34 | C.8 |
| 1.1651 | B.35 | C.8 |
| 1.1652 | B.36 | C.8 |
| 1.1653 | B.37 | C.8 |

TABLE 1-continued (compositions 1.1 to 1.3653):

| comp. no. | herbicide B | safener C |
|---|---|---|
| 1.1654 | B.38 | C.8 |
| 1.1655 | B.39 | C.8 |
| 1.1656 | B.40 | C.8 |
| 1.1657 | B.41 | C.8 |
| 1.1658 | B.42 | C.8 |
| 1.1659 | B.43 | C.8 |
| 1.1660 | B.44 | C.8 |
| 1.1661 | B.45 | C.8 |
| 1.1662 | B.46 | C.8 |
| 1.1663 | B.47 | C.8 |
| 1.1664 | B.48 | C.8 |
| 1.1665 | B.49 | C.8 |
| 1.1666 | B.50 | C.8 |
| 1.1667 | B.51 | C.8 |
| 1.1668 | B.52 | C.8 |
| 1.1669 | B.53 | C.8 |
| 1.1670 | B.54 | C.8 |
| 1.1671 | B.55 | C.8 |
| 1.1672 | B.56 | C.8 |
| 1.1673 | B.57 | C.8 |
| 1.1674 | B.58 | C.8 |
| 1.1675 | B.59 | C.8 |
| 1.1676 | B.60 | C.8 |
| 1.1677 | B.61 | C.8 |
| 1.1678 | B.62 | C.8 |
| 1.1679 | B.63 | C.8 |
| 1.1680 | B.64 | C.8 |
| 1.1681 | B.65 | C.8 |
| 1.1682 | B.66 | C.8 |
| 1.1683 | B.67 | C.8 |
| 1.1684 | B.68 | C.8 |
| 1.1685 | B.69 | C.8 |
| 1.1686 | B.70 | C.8 |
| 1.1687 | B.71 | C.8 |
| 1.1688 | B.72 | C.8 |
| 1.1689 | B.73 | C.8 |
| 1.1690 | B.74 | C.8 |
| 1.1691 | B.75 | C.8 |
| 1.1692 | B.76 | C.8 |
| 1.1693 | B.77 | C.8 |
| 1.1694 | B.78 | C.8 |
| 1.1695 | B.79 | C.8 |
| 1.1696 | B.80 | C.8 |
| 1.1697 | B.81 | C.8 |
| 1.1698 | B.82 | C.8 |
| 1.1699 | B.83 | C.8 |
| 1.1700 | B.84 | C.8 |
| 1.1701 | B.85 | C.8 |
| 1.1702 | B.86 | C.8 |
| 1.1703 | B.87 | C.8 |
| 1.1704 | B.88 | C.8 |
| 1.1705 | B.89 | C.8 |
| 1.1706 | B.90 | C.8 |
| 1.1707 | B.91 | C.8 |
| 1.1708 | B.92 | C.8 |
| 1.1709 | B.93 | C.8 |
| 1.1710 | B.94 | C.8 |
| 1.1711 | B.95 | C.8 |
| 1.1712 | B.96 | C.8 |
| 1.1713 | B.97 | C.8 |
| 1.1714 | B.98 | C.8 |
| 1.1715 | B.99 | C.8 |
| 1.1716 | B.100 | C.8 |
| 1.1717 | B.101 | C.8 |
| 1.1718 | B.102 | C.8 |
| 1.1719 | B.103 | C.8 |
| 1.1720 | B.104 | C.8 |
| 1.1721 | B.105 | C.8 |
| 1.1722 | B.106 | C.8 |
| 1.1723 | B.107 | C.8 |
| 1.1724 | B.108 | C.8 |
| 1.1725 | B.109 | C.8 |
| 1.1726 | B.110 | C.8 |
| 1.1727 | B.111 | C.8 |
| 1.1728 | B.112 | C.8 |
| 1.1729 | B.113 | C.8 |
| 1.1730 | B.114 | C.8 |
| 1.1731 | B.115 | C.8 |
| 1.1732 | B.116 | C.8 |
| 1.1733 | B.117 | C.8 |
| 1.1734 | B.118 | C.8 |
| 1.1735 | B.119 | C.8 |
| 1.1736 | B.120 | C.8 |
| 1.1737 | B.121 | C.8 |
| 1.1738 | B.122 | C.8 |
| 1.1739 | B.123 | C.8 |
| 1.1740 | B.124 | C.8 |
| 1.1741 | B.125 | C.8 |
| 1.1742 | B.126 | C.8 |
| 1.1743 | B.127 | C.8 |
| 1.1744 | B.128 | C.8 |
| 1.1745 | B.129 | C.8 |
| 1.1746 | B.130 | C.8 |
| 1.1747 | B.131 | C.8 |
| 1.1748 | B.132 | C.8 |
| 1.1749 | B.133 | C.8 |
| 1.1750 | B.134 | C.8 |
| 1.1751 | B.135 | C.8 |
| 1.1752 | B.136 | C.8 |
| 1.1753 | B.137 | C.8 |
| 1.1754 | B.138 | C.8 |
| 1.1755 | B.139 | C.8 |
| 1.1756 | B.140 | C.8 |
| 1.1757 | B.141 | C.8 |
| 1.1758 | B.142 | C.8 |
| 1.1759 | B.143 | C.8 |
| 1.1760 | B.144 | C.8 |
| 1.1761 | B.145 | C.8 |
| 1.1762 | B.146 | C.8 |
| 1.1763 | B.147 | C.8 |
| 1.1764 | B.148 | C.8 |
| 1.1765 | B.149 | C.8 |
| 1.1766 | B.150 | C.8 |
| 1.1767 | B.151 | C.8 |
| 1.1768 | B.152 | C.8 |
| 1.1769 | B.153 | C.8 |
| 1.1770 | B.154 | C.8 |
| 1.1771 | B.155 | C.8 |
| 1.1772 | B.156 | C.8 |
| 1.1773 | B.157 | C.8 |
| 1.1774 | B.158 | C.8 |
| 1.1775 | B.159 | C.8 |
| 1.1776 | B.160 | C.8 |
| 1.1777 | B.161 | C.8 |
| 1.1778 | B.162 | C.8 |
| 1.1779 | B.163 | C.8 |
| 1.1780 | B.164 | C.8 |
| 1.1781 | B.165 | C.8 |
| 1.1782 | B.166 | C.8 |
| 1.1783 | B.167 | C.8 |
| 1.1784 | B.168 | C.8 |
| 1.1785 | B.169 | C.8 |
| 1.1786 | B.170 | C.8 |
| 1.1787 | B.171 | C.8 |
| 1.1788 | B.172 | C.8 |
| 1.1789 | B.173 | C.8 |
| 1.1790 | B.174 | C.8 |
| 1.1791 | B.175 | C.8 |
| 1.1792 | B.176 | C.8 |
| 1.1793 | B.177 | C.8 |
| 1.1794 | B.178 | C.8 |
| 1.1795 | B.179 | C.8 |
| 1.1796 | B.180 | C.8 |
| 1.1797 | B.181 | C.8 |
| 1.1798 | B.182 | C.8 |
| 1.1799 | B.183 | C.8 |
| 1.1800 | B.184 | C.8 |
| 1.1801 | B.185 | C.8 |
| 1.1802 | B.186 | C.8 |
| 1.1803 | B.187 | C.8 |
| 1.1804 | B.188 | C.8 |
| 1.1805 | B.189 | C.8 |

TABLE 1-continued (compositions 1.1 to 1.3653):

| comp. no. | herbicide B | safener C |
|---|---|---|
| 1.1806 | B.190 | C.8 |
| 1.1807 | B.191 | C.8 |
| 1.1808 | B.192 | C.8 |
| 1.1809 | B.193 | C.8 |
| 1.1810 | B.194 | C.8 |
| 1.1811 | B.195 | C.8 |
| 1.1812 | B.196 | C.8 |
| 1.1813 | B.197 | C.8 |
| 1.1814 | B.198 | C.8 |
| 1.1815 | B.199 | C.8 |
| 1.1816 | B.200 | C.8 |
| 1.1817 | B.201 | C.8 |
| 1.1818 | B.202 | C.8 |
| 1.1819 | B.1 | C.9 |
| 1.1820 | B.2 | C.9 |
| 1.1821 | B.3 | C.9 |
| 1.1822 | B.4 | C.9 |
| 1.1823 | B.5 | C.9 |
| 1.1824 | B.6 | C.9 |
| 1.1825 | B.7 | C.9 |
| 1.1826 | B.8 | C.9 |
| 1.1827 | B.9 | C.9 |
| 1.1828 | B.10 | C.9 |
| 1.1829 | B.11 | C.9 |
| 1.1830 | B.12 | C.9 |
| 1.1831 | B.13 | C.9 |
| 1.1832 | B.14 | C.9 |
| 1.1833 | B.15 | C.9 |
| 1.1834 | B.16 | C.9 |
| 1.1835 | B.17 | C.9 |
| 1.1836 | B.18 | C.9 |
| 1.1837 | B.19 | C.9 |
| 1.1838 | B.20 | C.9 |
| 1.1839 | B.21 | C.9 |
| 1.1840 | B.22 | C.9 |
| 1.1841 | B.23 | C.9 |
| 1.1842 | B.24 | C.9 |
| 1.1843 | B.25 | C.9 |
| 1.1844 | B.26 | C.9 |
| 1.1845 | B.27 | C.9 |
| 1.1846 | B.28 | C.9 |
| 1.1847 | B.29 | C.9 |
| 1.1848 | B.30 | C.9 |
| 1.1849 | B.31 | C.9 |
| 1.1850 | B.32 | C.9 |
| 1.1851 | B.33 | C.9 |
| 1.1852 | B.34 | C.9 |
| 1.1853 | B.35 | C.9 |
| 1.1854 | B.36 | C.9 |
| 1.1855 | B.37 | C.9 |
| 1.1856 | B.38 | C.9 |
| 1.1857 | B.39 | C.9 |
| 1.1858 | B.40 | C.9 |
| 1.1859 | B.41 | C.9 |
| 1.1860 | B.42 | C.9 |
| 1.1861 | B.43 | C.9 |
| 1.1862 | B.44 | C.9 |
| 1.1863 | B.45 | C.9 |
| 1.1864 | B.46 | C.9 |
| 1.1865 | B.47 | C.9 |
| 1.1866 | B.48 | C.9 |
| 1.1867 | B.49 | C.9 |
| 1.1868 | B.50 | C.9 |
| 1.1869 | B.51 | C.9 |
| 1.1870 | B.52 | C.9 |
| 1.1871 | B.53 | C.9 |
| 1.1872 | B.54 | C.9 |
| 1.1873 | B.55 | C.9 |
| 1.1874 | B.56 | C.9 |
| 1.1875 | B.57 | C.9 |
| 1.1876 | B.58 | C.9 |
| 1.1877 | B.59 | C.9 |
| 1.1878 | B.60 | C.9 |
| 1.1879 | B.61 | C.9 |
| 1.1880 | B.62 | C.9 |
| 1.1881 | B.63 | C.9 |
| 1.1882 | B.64 | C.9 |
| 1.1883 | B.65 | C.9 |
| 1.1884 | B.66 | C.9 |
| 1.1885 | B.67 | C.9 |
| 1.1886 | B.68 | C.9 |
| 1.1887 | B.69 | C.9 |
| 1.1888 | B.70 | C.9 |
| 1.1889 | B.71 | C.9 |
| 1.1890 | B.72 | C.9 |
| 1.1891 | B.73 | C.9 |
| 1.1892 | B.74 | C.9 |
| 1.1893 | B.75 | C.9 |
| 1.1894 | B.76 | C.9 |
| 1.1895 | B.77 | C.9 |
| 1.1896 | B.78 | C.9 |
| 1.1897 | B.79 | C.9 |
| 1.1898 | B.80 | C.9 |
| 1.1899 | B.81 | C.9 |
| 1.1900 | B.82 | C.9 |
| 1.1901 | B.83 | C.9 |
| 1.1902 | B.84 | C.9 |
| 1.1903 | B.85 | C.9 |
| 1.1904 | B.86 | C.9 |
| 1.1905 | B.87 | C.9 |
| 1.1906 | B.88 | C.9 |
| 1.1907 | B.89 | C.9 |
| 1.1908 | B.90 | C.9 |
| 1.1909 | B.91 | C.9 |
| 1.1910 | B.92 | C.9 |
| 1.1911 | B.93 | C.9 |
| 1.1912 | B.94 | C.9 |
| 1.1913 | B.95 | C.9 |
| 1.1914 | B.96 | C.9 |
| 1.1915 | B.97 | C.9 |
| 1.1916 | B.98 | C.9 |
| 1.1917 | B.99 | C.9 |
| 1.1918 | B.100 | C.9 |
| 1.1919 | B.101 | C.9 |
| 1.1920 | B.102 | C.9 |
| 1.1921 | B.103 | C.9 |
| 1.1922 | B.104 | C.9 |
| 1.1923 | B.105 | C.9 |
| 1.1924 | B.106 | C.9 |
| 1.1925 | B.107 | C.9 |
| 1.1926 | B.108 | C.9 |
| 1.1927 | B.109 | C.9 |
| 1.1928 | B.110 | C.9 |
| 1.1929 | B.111 | C.9 |
| 1.1930 | B.112 | C.9 |
| 1.1931 | B.113 | C.9 |
| 1.1932 | B.114 | C.9 |
| 1.1933 | B.115 | C.9 |
| 1.1934 | B.116 | C.9 |
| 1.1935 | B.117 | C.9 |
| 1.1936 | B.118 | C.9 |
| 1.1937 | B.119 | C.9 |
| 1.1938 | B.120 | C.9 |
| 1.1939 | B.121 | C.9 |
| 1.1940 | B.122 | C.9 |
| 1.1941 | B.123 | C.9 |
| 1.1942 | B.124 | C.9 |
| 1.1943 | B.125 | C.9 |
| 1.1944 | B.126 | C.9 |
| 1.1945 | B.127 | C.9 |
| 1.1946 | B.128 | C.9 |
| 1.1947 | B.129 | C.9 |
| 1.1948 | B.130 | C.9 |
| 1.1949 | B.131 | C.9 |
| 1.1950 | B.132 | C.9 |
| 1.1951 | B.133 | C.9 |
| 1.1952 | B.134 | C.9 |
| 1.1953 | B.135 | C.9 |
| 1.1954 | B.136 | C.9 |
| 1.1955 | B.137 | C.9 |
| 1.1956 | B.138 | C.9 |
| 1.1957 | B.139 | C.9 |

TABLE 1-continued (compositions 1.1 to 1.3653):

| comp. no. | herbicide B | safener C |
|---|---|---|
| 1.1958 | B.140 | C.9 |
| 1.1959 | B.141 | C.9 |
| 1.1960 | B.142 | C.9 |
| 1.1961 | B.143 | C.9 |
| 1.1962 | B.144 | C.9 |
| 1.1963 | B.145 | C.9 |
| 1.1964 | B.146 | C.9 |
| 1.1965 | B.147 | C.9 |
| 1.1966 | B.148 | C.9 |
| 1.1967 | B.149 | C.9 |
| 1.1968 | B.150 | C.9 |
| 1.1969 | B.151 | C.9 |
| 1.1970 | B.152 | C.9 |
| 1.1971 | B.153 | C.9 |
| 1.1972 | B.154 | C.9 |
| 1.1973 | B.155 | C.9 |
| 1.1974 | B.156 | C.9 |
| 1.1975 | B.157 | C.9 |
| 1.1976 | B.158 | C.9 |
| 1.1977 | B.159 | C.9 |
| 1.1978 | B.160 | C.9 |
| 1.1979 | B.161 | C.9 |
| 1.1980 | B.162 | C.9 |
| 1.1981 | B.163 | C.9 |
| 1.1982 | B.164 | C.9 |
| 1.1983 | B.165 | C.9 |
| 1.1984 | B.166 | C.9 |
| 1.1985 | B.167 | C.9 |
| 1.1986 | B.168 | C.9 |
| 1.1987 | B.169 | C.9 |
| 1.1988 | B.170 | C.9 |
| 1.1989 | B.171 | C.9 |
| 1.1990 | B.172 | C.9 |
| 1.1991 | B.173 | C.9 |
| 1.1992 | B.174 | C.9 |
| 1.1993 | B.175 | C.9 |
| 1.1994 | B.176 | C.9 |
| 1.1995 | B.177 | C.9 |
| 1.1996 | B.178 | C.9 |
| 1.1997 | B.179 | C.9 |
| 1.1998 | B.180 | C.9 |
| 1.1999 | B.181 | C.9 |
| 1.2000 | B.182 | C.9 |
| 1.2001 | B.183 | C.9 |
| 1.2002 | B.184 | C.9 |
| 1.2003 | B.185 | C.9 |
| 1.2004 | B.186 | C.9 |
| 1.2005 | B.187 | C.9 |
| 1.2006 | B.188 | C.9 |
| 1.2007 | B.189 | C.9 |
| 1.2008 | B.190 | C.9 |
| 1.2009 | B.191 | C.9 |
| 1.2010 | B.192 | C.9 |
| 1.2011 | B.193 | C.9 |
| 1.2012 | B.194 | C.9 |
| 1.2013 | B.195 | C.9 |
| 1.2014 | B.196 | C.9 |
| 1.2015 | B.197 | C.9 |
| 1.2016 | B.198 | C.9 |
| 1.2017 | B.199 | C.9 |
| 1.2018 | B.200 | C.9 |
| 1.2019 | B.201 | C.9 |
| 1.2020 | B.202 | C.9 |
| 1.2021 | B.1 | C.10 |
| 1.2022 | B.2 | C.10 |
| 1.2023 | B.3 | C.10 |
| 1.2024 | B.4 | C.10 |
| 1.2025 | B.5 | C.10 |
| 1.2026 | B.6 | C.10 |
| 1.2027 | B.7 | C.10 |
| 1.2028 | B.8 | C.10 |
| 1.2029 | B.9 | C.10 |
| 1.2030 | B.10 | C.10 |
| 1.2031 | B.11 | C.10 |
| 1.2032 | B.12 | C.10 |
| 1.2033 | B.13 | C.10 |
| 1.2034 | B.14 | C.10 |
| 1.2035 | B.15 | C.10 |
| 1.2036 | B.16 | C.10 |
| 1.2037 | B.17 | C.10 |
| 1.2038 | B.18 | C.10 |
| 1.2039 | B.19 | C.10 |
| 1.2040 | B.20 | C.10 |
| 1.2041 | B.21 | C.10 |
| 1.2042 | B.22 | C.10 |
| 1.2043 | B.23 | C.10 |
| 1.2044 | B.24 | C.10 |
| 1.2045 | B.25 | C.10 |
| 1.2046 | B.26 | C.10 |
| 1.2047 | B.27 | C.10 |
| 1.2048 | B.28 | C.10 |
| 1.2049 | B.29 | C.10 |
| 1.2050 | B.30 | C.10 |
| 1.2051 | B.31 | C.10 |
| 1.2052 | B.32 | C.10 |
| 1.2053 | B.33 | C.10 |
| 1.2054 | B.34 | C.10 |
| 1.2055 | B.35 | C.10 |
| 1.2056 | B.36 | C.10 |
| 1.2057 | B.37 | C.10 |
| 1.2058 | B.38 | C.10 |
| 1.2059 | B.39 | C.10 |
| 1.2060 | B.40 | C.10 |
| 1.2061 | B.41 | C.10 |
| 1.2062 | B.42 | C.10 |
| 1.2063 | B.43 | C.10 |
| 1.2064 | B.44 | C.10 |
| 1.2065 | B.45 | C.10 |
| 1.2066 | B.46 | C.10 |
| 1.2067 | B.47 | C.10 |
| 1.2068 | B.48 | C.10 |
| 1.2069 | B.49 | C.10 |
| 1.2070 | B.50 | C.10 |
| 1.2071 | B.51 | C.10 |
| 1.2072 | B.52 | C.10 |
| 1.2073 | B.53 | C.10 |
| 1.2074 | B.54 | C.10 |
| 1.2075 | B.55 | C.10 |
| 1.2076 | B.56 | C.10 |
| 1.2077 | B.57 | C.10 |
| 1.2078 | B.58 | C.10 |
| 1.2079 | B.59 | C.10 |
| 1.2080 | B.60 | C.10 |
| 1.2081 | B.61 | C.10 |
| 1.2082 | B.62 | C.10 |
| 1.2083 | B.63 | C.10 |
| 1.2084 | B.64 | C.10 |
| 1.2085 | B.65 | C.10 |
| 1.2086 | B.66 | C.10 |
| 1.2087 | B.67 | C.10 |
| 1.2088 | B.68 | C.10 |
| 1.2089 | B.69 | C.10 |
| 1.2090 | B.70 | C.10 |
| 1.2091 | B.71 | C.10 |
| 1.2092 | B.72 | C.10 |
| 1.2093 | B.73 | C.10 |
| 1.2094 | B.74 | C.10 |
| 1.2095 | B.75 | C.10 |
| 1.2096 | B.76 | C.10 |
| 1.2097 | B.77 | C.10 |
| 1.2098 | B.78 | C.10 |
| 1.2099 | B.79 | C.10 |
| 1.2100 | B.80 | C.10 |
| 1.2101 | B.81 | C.10 |
| 1.2102 | B.82 | C.10 |
| 1.2103 | B.83 | C.10 |
| 1.2104 | B.84 | C.10 |
| 1.2105 | B.85 | C.10 |
| 1.2106 | B.86 | C.10 |
| 1.2107 | B.87 | C.10 |
| 1.2108 | B.88 | C.10 |
| 1.2109 | B.89 | C.10 |

TABLE 1-continued (compositions 1.1 to 1.3653):

| comp. no. | herbicide B | safener C |
|---|---|---|
| 1.2110 | B.90 | C.10 |
| 1.2111 | B.91 | C.10 |
| 1.2112 | B.92 | C.10 |
| 1.2113 | B.93 | C.10 |
| 1.2114 | B.94 | C.10 |
| 1.2115 | B.95 | C.10 |
| 1.2116 | B.96 | C.10 |
| 1.2117 | B.97 | C.10 |
| 1.2118 | B.98 | C.10 |
| 1.2119 | B.99 | C.10 |
| 1.2120 | B.100 | C.10 |
| 1.2121 | B.101 | C.10 |
| 1.2122 | B.102 | C.10 |
| 1.2123 | B.103 | C.10 |
| 1.2124 | B.104 | C.10 |
| 1.2125 | B.105 | C.10 |
| 1.2126 | B.106 | C.10 |
| 1.2127 | B.107 | C.10 |
| 1.2128 | B.108 | C.10 |
| 1.2129 | B.109 | C.10 |
| 1.2130 | B.110 | C.10 |
| 1.2131 | B.111 | C.10 |
| 1.2132 | B.112 | C.10 |
| 1.2133 | B.113 | C.10 |
| 1.2134 | B.114 | C.10 |
| 1.2135 | B.115 | C.10 |
| 1.2136 | B.116 | C.10 |
| 1.2137 | B.117 | C.10 |
| 1.2138 | B.118 | C.10 |
| 1.2139 | B.119 | C.10 |
| 1.2140 | B.120 | C.10 |
| 1.2141 | B.121 | C.10 |
| 1.2142 | B.122 | C.10 |
| 1.2143 | B.123 | C.10 |
| 1.2144 | B.124 | C.10 |
| 1.2145 | B.125 | C.10 |
| 1.2146 | B.126 | C.10 |
| 1.2147 | B.127 | C.10 |
| 1.2148 | B.128 | C.10 |
| 1.2149 | B.129 | C.10 |
| 1.2150 | B.130 | C.10 |
| 1.2151 | B.131 | C.10 |
| 1.2152 | B.132 | C.10 |
| 1.2153 | B.133 | C.10 |
| 1.2154 | B.134 | C.10 |
| 1.2155 | B.135 | C.10 |
| 1.2156 | B.136 | C.10 |
| 1.2157 | B.137 | C.10 |
| 1.2158 | B.138 | C.10 |
| 1.2159 | B.139 | C.10 |
| 1.2160 | B.140 | C.10 |
| 1.2161 | B.141 | C.10 |
| 1.2162 | B.142 | C.10 |
| 1.2163 | B.143 | C.10 |
| 1.2164 | B.144 | C.10 |
| 1.2165 | B.145 | C.10 |
| 1.2166 | B.146 | C.10 |
| 1.2167 | B.147 | C.10 |
| 1.2168 | B.148 | C.10 |
| 1.2169 | B.149 | C.10 |
| 1.2170 | B.150 | C.10 |
| 1.2171 | B.151 | C.10 |
| 1.2172 | B.152 | C.10 |
| 1.2173 | B.153 | C.10 |
| 1.2174 | B.154 | C.10 |
| 1.2175 | B.155 | C.10 |
| 1.2176 | B.156 | C.10 |
| 1.2177 | B.157 | C.10 |
| 1.2178 | B.158 | C.10 |
| 1.2179 | B.159 | C.10 |
| 1.2180 | B.160 | C.10 |
| 1.2181 | B.161 | C.10 |
| 1.2182 | B.162 | C.10 |
| 1.2183 | B.163 | C.10 |
| 1.2184 | B.164 | C.10 |
| 1.2185 | B.165 | C.10 |
| 1.2186 | B.166 | C.10 |
| 1.2187 | B.167 | C.10 |
| 1.2188 | B.168 | C.10 |
| 1.2189 | B.169 | C.10 |
| 1.2190 | B.170 | C.10 |
| 1.2191 | B.171 | C.10 |
| 1.2192 | B.172 | C.10 |
| 1.2193 | B.173 | C.10 |
| 1.2194 | B.174 | C.10 |
| 1.2195 | B.175 | C.10 |
| 1.2196 | B.176 | C.10 |
| 1.2197 | B.177 | C.10 |
| 1.2198 | B.178 | C.10 |
| 1.2199 | B.179 | C.10 |
| 1.2200 | B.180 | C.10 |
| 1.2201 | B.181 | C.10 |
| 1.2202 | B.182 | C.10 |
| 1.2203 | B.183 | C.10 |
| 1.2204 | B.184 | C.10 |
| 1.2205 | B.185 | C.10 |
| 1.2206 | B.186 | C.10 |
| 1.2207 | B.187 | C.10 |
| 1.2208 | B.188 | C.10 |
| 1.2209 | B.189 | C.10 |
| 1.2210 | B.190 | C.10 |
| 1.2211 | B.191 | C.10 |
| 1.2212 | B.192 | C.10 |
| 1.2213 | B.193 | C.10 |
| 1.2214 | B.194 | C.10 |
| 1.2215 | B.195 | C.10 |
| 1.2216 | B.196 | C.10 |
| 1.2217 | B.197 | C.10 |
| 1.2218 | B.198 | C.10 |
| 1.2219 | B.199 | C.10 |
| 1.2220 | B.200 | C.10 |
| 1.2221 | B.201 | C.10 |
| 1.2222 | B.202 | C.10 |
| 1.2223 | B.1 | C.11 |
| 1.2224 | B.2 | C.11 |
| 1.2225 | B.3 | C.11 |
| 1.2226 | B.4 | C.11 |
| 1.2227 | B.5 | C.11 |
| 1.2228 | B.6 | C.11 |
| 1.2229 | B.7 | C.11 |
| 1.2230 | B.8 | C.11 |
| 1.2231 | B.9 | C.11 |
| 1.2232 | B.10 | C.11 |
| 1.2233 | B.11 | C.11 |
| 1.2234 | B.12 | C.11 |
| 1.2235 | B.13 | C.11 |
| 1.2236 | B.14 | C.11 |
| 1.2237 | B.15 | C.11 |
| 1.2238 | B.16 | C.11 |
| 1.2239 | B.17 | C.11 |
| 1.2240 | B.18 | C.11 |
| 1.2241 | B.19 | C.11 |
| 1.2242 | B.20 | C.11 |
| 1.2243 | B.21 | C.11 |
| 1.2244 | B.22 | C.11 |
| 1.2245 | B.23 | C.11 |
| 1.2246 | B.24 | C.11 |
| 1.2247 | B.25 | C.11 |
| 1.2248 | B.26 | C.11 |
| 1.2249 | B.27 | C.11 |
| 1.2250 | B.28 | C.11 |
| 1.2251 | B.29 | C.11 |
| 1.2252 | B.30 | C.11 |
| 1.2253 | B.31 | C.11 |
| 1.2254 | B.32 | C.11 |
| 1.2255 | B.33 | C.11 |
| 1.2256 | B.34 | C.11 |
| 1.2257 | B.35 | C.11 |
| 1.2258 | B.36 | C.11 |
| 1.2259 | B.37 | C.11 |
| 1.2260 | B.38 | C.11 |
| 1.2261 | B.39 | C.11 |

TABLE 1-continued

(compositions 1.1 to 1.3653):

| comp. no. | herbicide B | safener C |
|---|---|---|
| 1.2262 | B.40 | C.11 |
| 1.2263 | B.41 | C.11 |
| 1.2264 | B.42 | C.11 |
| 1.2265 | B.43 | C.11 |
| 1.2266 | B.44 | C.11 |
| 1.2267 | B.45 | C.11 |
| 1.2268 | B.46 | C.11 |
| 1.2269 | B.47 | C.11 |
| 1.2270 | B.48 | C.11 |
| 1.2271 | B.49 | C.11 |
| 1.2272 | B.50 | C.11 |
| 1.2273 | B.51 | C.11 |
| 1.2274 | B.52 | C.11 |
| 1.2275 | B.53 | C.11 |
| 1.2276 | B.54 | C.11 |
| 1.2277 | B.55 | C.11 |
| 1.2278 | B.56 | C.11 |
| 1.2279 | B.57 | C.11 |
| 1.2280 | B.58 | C.11 |
| 1.2281 | B.59 | C.11 |
| 1.2282 | B.60 | C.11 |
| 1.2283 | B.61 | C.11 |
| 1.2284 | B.62 | C.11 |
| 1.2285 | B.63 | C.11 |
| 1.2286 | B.64 | C.11 |
| 1.2287 | B.65 | C.11 |
| 1.2288 | B.66 | C.11 |
| 1.2289 | B.67 | C.11 |
| 1.2290 | B.68 | C.11 |
| 1.2291 | B.69 | C.11 |
| 1.2292 | B.70 | C.11 |
| 1.2293 | B.71 | C.11 |
| 1.2294 | B.72 | C.11 |
| 1.2295 | B.73 | C.11 |
| 1.2296 | B.74 | C.11 |
| 1.2297 | B.75 | C.11 |
| 1.2298 | B.76 | C.11 |
| 1.2299 | B.77 | C.11 |
| 1.2300 | B.78 | C.11 |
| 1.2301 | B.79 | C.11 |
| 1.2302 | B.80 | C.11 |
| 1.2303 | B.81 | C.11 |
| 1.2304 | B.82 | C.11 |
| 1.2305 | B.83 | C.11 |
| 1.2306 | B.84 | C.11 |
| 1.2307 | B.85 | C.11 |
| 1.2308 | B.86 | C.11 |
| 1.2309 | B.87 | C.11 |
| 1.2310 | B.88 | C.11 |
| 1.2311 | B.89 | C.11 |
| 1.2312 | B.90 | C.11 |
| 1.2313 | B.91 | C.11 |
| 1.2314 | B.92 | C.11 |
| 1.2315 | B.93 | C.11 |
| 1.2316 | B.94 | C.11 |
| 1.2317 | B.95 | C.11 |
| 1.2318 | B.96 | C.11 |
| 1.2319 | B.97 | C.11 |
| 1.2320 | B.98 | C.11 |
| 1.2321 | B.99 | C.11 |
| 1.2322 | B.100 | C.11 |
| 1.2323 | B.101 | C.11 |
| 1.2324 | B.102 | C.11 |
| 1.2325 | B.103 | C.11 |
| 1.2326 | B.104 | C.11 |
| 1.2327 | B.105 | C.11 |
| 1.2328 | B.106 | C.11 |
| 1.2329 | B.107 | C.11 |
| 1.2330 | B.108 | C.11 |
| 1.2331 | B.109 | C.11 |
| 1.2332 | B.110 | C.11 |
| 1.2333 | B.111 | C.11 |
| 1.2334 | B.112 | C.11 |
| 1.2335 | B.113 | C.11 |
| 1.2336 | B.114 | C.11 |
| 1.2337 | B.115 | C.11 |
| 1.2338 | B.116 | C.11 |
| 1.2339 | B.117 | C.11 |
| 1.2340 | B.118 | C.11 |
| 1.2341 | B.119 | C.11 |
| 1.2342 | B.120 | C.11 |
| 1.2343 | B.121 | C.11 |
| 1.2344 | B.122 | C.11 |
| 1.2345 | B.123 | C.11 |
| 1.2346 | B.124 | C.11 |
| 1.2347 | B.125 | C.11 |
| 1.2348 | B.126 | C.11 |
| 1.2349 | B.127 | C.11 |
| 1.2350 | B.128 | C.11 |
| 1.2351 | B.129 | C.11 |
| 1.2352 | B.130 | C.11 |
| 1.2353 | B.131 | C.11 |
| 1.2354 | B.132 | C.11 |
| 1.2355 | B.133 | C.11 |
| 1.2356 | B.134 | C.11 |
| 1.2357 | B.135 | C.11 |
| 1.2358 | B.136 | C.11 |
| 1.2359 | B.137 | C.11 |
| 1.2360 | B.138 | C.11 |
| 1.2361 | B.139 | C.11 |
| 1.2362 | B.140 | C.11 |
| 1.2363 | B.141 | C.11 |
| 1.2364 | B.142 | C.11 |
| 1.2365 | B.143 | C.11 |
| 1.2366 | B.144 | C.11 |
| 1.2367 | B.145 | C.11 |
| 1.2368 | B.146 | C.11 |
| 1.2369 | B.147 | C.11 |
| 1.2370 | B.148 | C.11 |
| 1.2371 | B.149 | C.11 |
| 1.2372 | B.150 | C.11 |
| 1.2373 | B.151 | C.11 |
| 1.2374 | B.152 | C.11 |
| 1.2375 | B.153 | C.11 |
| 1.2376 | B.154 | C.11 |
| 1.2377 | B.155 | C.11 |
| 1.2378 | B.156 | C.11 |
| 1.2379 | B.157 | C.11 |
| 1.2380 | B.158 | C.11 |
| 1.2381 | B.159 | C.11 |
| 1.2382 | B.160 | C.11 |
| 1.2383 | B.161 | C.11 |
| 1.2384 | B.162 | C.11 |
| 1.2385 | B.163 | C.11 |
| 1.2386 | B.164 | C.11 |
| 1.2387 | B.165 | C.11 |
| 1.2388 | B.166 | C.11 |
| 1.2389 | B.167 | C.11 |
| 1.2390 | B.168 | C.11 |
| 1.2391 | B.169 | C.11 |
| 1.2392 | B.170 | C.11 |
| 1.2393 | B.171 | C.11 |
| 1.2394 | B.172 | C.11 |
| 1.2395 | B.173 | C.11 |
| 1.2396 | B.174 | C.11 |
| 1.2397 | B.175 | C.11 |
| 1.2398 | B.176 | C.11 |
| 1.2399 | B.177 | C.11 |
| 1.2400 | B.178 | C.11 |
| 1.2401 | B.179 | C.11 |
| 1.2402 | B.180 | C.11 |
| 1.2403 | B.181 | C.11 |
| 1.2404 | B.182 | C.11 |
| 1.2405 | B.183 | C.11 |
| 1.2406 | B.184 | C.11 |
| 1.2407 | B.185 | C.11 |
| 1.2408 | B.186 | C.11 |
| 1.2409 | B.187 | C.11 |
| 1.2410 | B.188 | C.11 |
| 1.2411 | B.189 | C.11 |
| 1.2412 | B.190 | C.11 |
| 1.2413 | B.191 | C.11 |

TABLE 1-continued (compositions 1.1 to 1.3653):

| comp. no. | herbicide B | safener C |
|---|---|---|
| 1.2414 | B.192 | C.11 |
| 1.2415 | B.193 | C.11 |
| 1.2416 | B.194 | C.11 |
| 1.2417 | B.195 | C.11 |
| 1.2418 | B.196 | C.11 |
| 1.2419 | B.197 | C.11 |
| 1.2420 | B.198 | C.11 |
| 1.2421 | B.199 | C.11 |
| 1.2422 | B.200 | C.11 |
| 1.2423 | B.201 | C.11 |
| 1.2424 | B.202 | C.11 |
| 1.2425 | B.1 | C.12 |
| 1.2426 | B.2 | C.12 |
| 1.2427 | B.3 | C.12 |
| 1.2428 | B.4 | C.12 |
| 1.2429 | B.5 | C.12 |
| 1.2430 | B.6 | C.12 |
| 1.2431 | B.7 | C.12 |
| 1.2432 | B.8 | C.12 |
| 1.2433 | B.9 | C.12 |
| 1.2434 | B.10 | C.12 |
| 1.2435 | B.11 | C.12 |
| 1.2436 | B.12 | C.12 |
| 1.2437 | B.13 | C.12 |
| 1.2438 | B.14 | C.12 |
| 1.2439 | B.15 | C.12 |
| 1.2440 | B.16 | C.12 |
| 1.2441 | B.17 | C.12 |
| 1.2442 | B.18 | C.12 |
| 1.2443 | B.19 | C.12 |
| 1.2444 | B.20 | C.12 |
| 1.2445 | B.21 | C.12 |
| 1.2446 | B.22 | C.12 |
| 1.2447 | B.23 | C.12 |
| 1.2448 | B.24 | C.12 |
| 1.2449 | B.25 | C.12 |
| 1.2450 | B.26 | C.12 |
| 1.2451 | B.27 | C.12 |
| 1.2452 | B.28 | C.12 |
| 1.2453 | B.29 | C.12 |
| 1.2454 | B.30 | C.12 |
| 1.2455 | B.31 | C.12 |
| 1.2456 | B.32 | C.12 |
| 1.2457 | B.33 | C.12 |
| 1.2458 | B.34 | C.12 |
| 1.2459 | B.35 | C.12 |
| 1.2460 | B.36 | C.12 |
| 1.2461 | B.37 | C.12 |
| 1.2462 | B.38 | C.12 |
| 1.2463 | B.39 | C.12 |
| 1.2464 | B.40 | C.12 |
| 1.2465 | B.41 | C.12 |
| 1.2466 | B.42 | C.12 |
| 1.2467 | B.43 | C.12 |
| 1.2468 | B.44 | C.12 |
| 1.2469 | B.45 | C.12 |
| 1.2470 | B.46 | C.12 |
| 1.2471 | B.47 | C.12 |
| 1.2472 | B.48 | C.12 |
| 1.2473 | B.49 | C.12 |
| 1.2474 | B.50 | C.12 |
| 1.2475 | B.51 | C.12 |
| 1.2476 | B.52 | C.12 |
| 1.2477 | B.53 | C.12 |
| 1.2478 | B.54 | C.12 |
| 1.2479 | B.55 | C.12 |
| 1.2480 | B.56 | C.12 |
| 1.2481 | B.57 | C.12 |
| 1.2482 | B.58 | C.12 |
| 1.2483 | B.59 | C.12 |
| 1.2484 | B.60 | C.12 |
| 1.2485 | B.61 | C.12 |
| 1.2486 | B.62 | C.12 |
| 1.2487 | B.63 | C.12 |
| 1.2488 | B.64 | C.12 |
| 1.2489 | B.65 | C.12 |
| 1.2490 | B.66 | C.12 |
| 1.2491 | B.67 | C.12 |
| 1.2492 | B.68 | C.12 |
| 1.2493 | B.69 | C.12 |
| 1.2494 | B.70 | C.12 |
| 1.2495 | B.71 | C.12 |
| 1.2496 | B.72 | C.12 |
| 1.2497 | B.73 | C.12 |
| 1.2498 | B.74 | C.12 |
| 1.2499 | B.75 | C.12 |
| 1.2500 | B.76 | C.12 |
| 1.2501 | B.77 | C.12 |
| 1.2502 | B.78 | C.12 |
| 1.2503 | B.79 | C.12 |
| 1.2504 | B.80 | C.12 |
| 1.2505 | B.81 | C.12 |
| 1.2506 | B.82 | C.12 |
| 1.2507 | B.83 | C.12 |
| 1.2508 | B.84 | C.12 |
| 1.2509 | B.85 | C.12 |
| 1.2510 | B.86 | C.12 |
| 1.2511 | B.87 | C.12 |
| 1.2512 | B.88 | C.12 |
| 1.2513 | B.89 | C.12 |
| 1.2514 | B.90 | C.12 |
| 1.2515 | B.91 | C.12 |
| 1.2516 | B.92 | C.12 |
| 1.2517 | B.93 | C.12 |
| 1.2518 | B.94 | C.12 |
| 1.2519 | B.95 | C.12 |
| 1.2520 | B.96 | C.12 |
| 1.2521 | B.97 | C.12 |
| 1.2522 | B.98 | C.12 |
| 1.2523 | B.99 | C.12 |
| 1.2524 | B.100 | C.12 |
| 1.2525 | B.101 | C.12 |
| 1.2526 | B.102 | C.12 |
| 1.2527 | B.103 | C.12 |
| 1.2528 | B.104 | C.12 |
| 1.2529 | B.105 | C.12 |
| 1.2530 | B.106 | C.12 |
| 1.2531 | B.107 | C.12 |
| 1.2532 | B.108 | C.12 |
| 1.2533 | B.109 | C.12 |
| 1.2534 | B.110 | C.12 |
| 1.2535 | B.111 | C.12 |
| 1.2536 | B.112 | C.12 |
| 1.2537 | B.113 | C.12 |
| 1.2538 | B.114 | C.12 |
| 1.2539 | B.115 | C.12 |
| 1.2540 | B.116 | C.12 |
| 1.2541 | B.117 | C.12 |
| 1.2542 | B.118 | C.12 |
| 1.2543 | B.119 | C.12 |
| 1.2544 | B.120 | C.12 |
| 1.2545 | B.121 | C.12 |
| 1.2546 | B.122 | C.12 |
| 1.2547 | B.123 | C.12 |
| 1.2548 | B.124 | C.12 |
| 1.2549 | B.125 | C.12 |
| 1.2550 | B.126 | C.12 |
| 1.2551 | B.127 | C.12 |
| 1.2552 | B.128 | C.12 |
| 1.2553 | B.129 | C.12 |
| 1.2554 | B.130 | C.12 |
| 1.2555 | B.131 | C.12 |
| 1.2556 | B.132 | C.12 |
| 1.2557 | B.133 | C.12 |
| 1.2558 | B.134 | C.12 |
| 1.2559 | B.135 | C.12 |
| 1.2560 | B.136 | C.12 |
| 1.2561 | B.137 | C.12 |
| 1.2562 | B.138 | C.12 |
| 1.2563 | B.139 | C.12 |
| 1.2564 | B.140 | C.12 |
| 1.2565 | B.141 | C.12 |

TABLE 1-continued (compositions 1.1 to 1.3653):

| comp. no. | herbicide B | safener C |
|---|---|---|
| 1.2566 | B.142 | C.12 |
| 1.2567 | B.143 | C.12 |
| 1.2568 | B.144 | C.12 |
| 1.2569 | B.145 | C.12 |
| 1.2570 | B.146 | C.12 |
| 1.2571 | B.147 | C.12 |
| 1.2572 | B.148 | C.12 |
| 1.2573 | B.149 | C.12 |
| 1.2574 | B.150 | C.12 |
| 1.2575 | B.151 | C.12 |
| 1.2576 | B.152 | C.12 |
| 1.2577 | B.153 | C.12 |
| 1.2578 | B.154 | C.12 |
| 1.2579 | B.155 | C.12 |
| 1.2580 | B.156 | C.12 |
| 1.2581 | B.157 | C.12 |
| 1.2582 | B.158 | C.12 |
| 1.2583 | B.159 | C.12 |
| 1.2584 | B.160 | C.12 |
| 1.2585 | B.161 | C.12 |
| 1.2586 | B.162 | C.12 |
| 1.2587 | B.163 | C.12 |
| 1.2588 | B.164 | C.12 |
| 1.2589 | B.165 | C.12 |
| 1.2590 | B.166 | C.12 |
| 1.2591 | B.167 | C.12 |
| 1.2592 | B.168 | C.12 |
| 1.2593 | B.169 | C.12 |
| 1.2594 | B.170 | C.12 |
| 1.2595 | B.171 | C.12 |
| 1.2596 | B.172 | C.12 |
| 1.2597 | B.173 | C.12 |
| 1.2598 | B.174 | C.12 |
| 1.2599 | B.175 | C.12 |
| 1.2600 | B.176 | C.12 |
| 1.2601 | B.177 | C.12 |
| 1.2602 | B.178 | C.12 |
| 1.2603 | B.179 | C.12 |
| 1.2604 | B.180 | C.12 |
| 1.2605 | B.181 | C.12 |
| 1.2606 | B.182 | C.12 |
| 1.2607 | B.183 | C.12 |
| 1.2608 | B.184 | C.12 |
| 1.2609 | B.185 | C.12 |
| 1.2610 | B.186 | C.12 |
| 1.2611 | B.187 | C.12 |
| 1.2612 | B.188 | C.12 |
| 1.2613 | B.189 | C.12 |
| 1.2614 | B.190 | C.12 |
| 1.2615 | B.191 | C.12 |
| 1.2616 | B.192 | C.12 |
| 1.2617 | B.193 | C.12 |
| 1.2618 | B.194 | C.12 |
| 1.2619 | B.195 | C.12 |
| 1.2620 | B.196 | C.12 |
| 1.2621 | B.197 | C.12 |
| 1.2622 | B.198 | C.12 |
| 1.2623 | B.199 | C.12 |
| 1.2624 | B.200 | C.12 |
| 1.2625 | B.201 | C.12 |
| 1.2626 | B.202 | C.12 |
| 1.2627 | B.1 | C.13 |
| 1.2628 | B.2 | C.13 |
| 1.2629 | B.3 | C.13 |
| 1.2630 | B.4 | C.13 |
| 1.2631 | B.5 | C.13 |
| 1.2632 | B.6 | C.13 |
| 1.2633 | B.7 | C.13 |
| 1.2634 | B.8 | C.13 |
| 1.2635 | B.9 | C.13 |
| 1.2636 | B.10 | C.13 |
| 1.2637 | B.11 | C.13 |
| 1.2638 | B.12 | C.13 |
| 1.2639 | B.13 | C.13 |
| 1.2640 | B.14 | C.13 |
| 1.2641 | B.15 | C.13 |
| 1.2642 | B.16 | C.13 |
| 1.2643 | B.17 | C.13 |
| 1.2644 | B.18 | C.13 |
| 1.2645 | B.19 | C.13 |
| 1.2646 | B.20 | C.13 |
| 1.2647 | B.21 | C.13 |
| 1.2648 | B.22 | C.13 |
| 1.2649 | B.23 | C.13 |
| 1.2650 | B.24 | C.13 |
| 1.2651 | B.25 | C.13 |
| 1.2652 | B.26 | C.13 |
| 1.2653 | B.27 | C.13 |
| 1.2654 | B.28 | C.13 |
| 1.2655 | B.29 | C.13 |
| 1.2656 | B.30 | C.13 |
| 1.2657 | B.31 | C.13 |
| 1.2658 | B.32 | C.13 |
| 1.2659 | B.33 | C.13 |
| 1.2660 | B.34 | C.13 |
| 1.2661 | B.35 | C.13 |
| 1.2662 | B.36 | C.13 |
| 1.2663 | B.37 | C.13 |
| 1.2664 | B.38 | C.13 |
| 1.2665 | B.39 | C.13 |
| 1.2666 | B.40 | C.13 |
| 1.2667 | B.41 | C.13 |
| 1.2668 | B.42 | C.13 |
| 1.2669 | B.43 | C.13 |
| 1.2670 | B.44 | C.13 |
| 1.2671 | B.45 | C.13 |
| 1.2672 | B.46 | C.13 |
| 1.2673 | B.47 | C.13 |
| 1.2674 | B.48 | C.13 |
| 1.2675 | B.49 | C.13 |
| 1.2676 | B.50 | C.13 |
| 1.2677 | B.51 | C.13 |
| 1.2678 | B.52 | C.13 |
| 1.2679 | B.53 | C.13 |
| 1.2680 | B.54 | C.13 |
| 1.2681 | B.55 | C.13 |
| 1.2682 | B.56 | C.13 |
| 1.2683 | B.57 | C.13 |
| 1.2684 | B.58 | C.13 |
| 1.2685 | B.59 | C.13 |
| 1.2686 | B.60 | C.13 |
| 1.2687 | B.61 | C.13 |
| 1.2688 | B.62 | C.13 |
| 1.2689 | B.63 | C.13 |
| 1.2690 | B.64 | C.13 |
| 1.2691 | B.65 | C.13 |
| 1.2692 | B.66 | C.13 |
| 1.2693 | B.67 | C.13 |
| 1.2694 | B.68 | C.13 |
| 1.2695 | B.69 | C.13 |
| 1.2696 | B.70 | C.13 |
| 1.2697 | B.71 | C.13 |
| 1.2698 | B.72 | C.13 |
| 1.2699 | B.73 | C.13 |
| 1.2700 | B.74 | C.13 |
| 1.2701 | B.75 | C.13 |
| 1.2702 | B.76 | C.13 |
| 1.2703 | B.77 | C.13 |
| 1.2704 | B.78 | C.13 |
| 1.2705 | B.79 | C.13 |
| 1.2706 | B.80 | C.13 |
| 1.2707 | B.81 | C.13 |
| 1.2708 | B.82 | C.13 |
| 1.2709 | B.83 | C.13 |
| 1.2710 | B.84 | C.13 |
| 1.2711 | B.85 | C.13 |
| 1.2712 | B.86 | C.13 |
| 1.2713 | B.87 | C.13 |
| 1.2714 | B.88 | C.13 |
| 1.2715 | B.89 | C.13 |
| 1.2716 | B.90 | C.13 |
| 1.2717 | B.91 | C.13 |

TABLE 1-continued (compositions 1.1 to 1.3653):

| comp. no. | herbicide B | safener C |
|---|---|---|
| 1.2718 | B.92 | C.13 |
| 1.2719 | B.93 | C.13 |
| 1.2720 | B.94 | C.13 |
| 1.2721 | B.95 | C.13 |
| 1.2722 | B.96 | C.13 |
| 1.2723 | B.97 | C.13 |
| 1.2724 | B.98 | C.13 |
| 1.2725 | B.99 | C.13 |
| 1.2726 | B.100 | C.13 |
| 1.2727 | B.101 | C.13 |
| 1.2728 | B.102 | C.13 |
| 1.2729 | B.103 | C.13 |
| 1.2730 | B.104 | C.13 |
| 1.2731 | B.105 | C.13 |
| 1.2732 | B.106 | C.13 |
| 1.2733 | B.107 | C.13 |
| 1.2734 | B.108 | C.13 |
| 1.2735 | B.109 | C.13 |
| 1.2736 | B.110 | C.13 |
| 1.2737 | B.111 | C.13 |
| 1.2738 | B.112 | C.13 |
| 1.2739 | B.113 | C.13 |
| 1.2740 | B.114 | C.13 |
| 1.2741 | B.115 | C.13 |
| 1.2742 | B.116 | C.13 |
| 1.2743 | B.117 | C.13 |
| 1.2744 | B.118 | C.13 |
| 1.2745 | B.119 | C.13 |
| 1.2746 | B.120 | C.13 |
| 1.2747 | B.121 | C.13 |
| 1.2748 | B.122 | C.13 |
| 1.2749 | B.123 | C.13 |
| 1.2750 | B.124 | C.13 |
| 1.2751 | B.125 | C.13 |
| 1.2752 | B.126 | C.13 |
| 1.2753 | B.127 | C.13 |
| 1.2754 | B.128 | C.13 |
| 1.2755 | B.129 | C.13 |
| 1.2756 | B.130 | C.13 |
| 1.2757 | B.131 | C.13 |
| 1.2758 | B.132 | C.13 |
| 1.2759 | B.133 | C.13 |
| 1.2760 | B.134 | C.13 |
| 1.2761 | B.135 | C.13 |
| 1.2762 | B.136 | C.13 |
| 1.2763 | B.137 | C.13 |
| 1.2764 | B.138 | C.13 |
| 1.2765 | B.139 | C.13 |
| 1.2766 | B.140 | C.13 |
| 1.2767 | B.141 | C.13 |
| 1.2768 | B.142 | C.13 |
| 1.2769 | B.143 | C.13 |
| 1.2770 | B.144 | C.13 |
| 1.2771 | B.145 | C.13 |
| 1.2772 | B.146 | C.13 |
| 1.2773 | B.147 | C.13 |
| 1.2774 | B.148 | C.13 |
| 1.2775 | B.149 | C.13 |
| 1.2776 | B.150 | C.13 |
| 1.2777 | B.151 | C.13 |
| 1.2778 | B.152 | C.13 |
| 1.2779 | B.153 | C.13 |
| 1.2780 | B.154 | C.13 |
| 1.2781 | B.155 | C.13 |
| 1.2782 | B.156 | C.13 |
| 1.2783 | B.157 | C.13 |
| 1.2784 | B.158 | C.13 |
| 1.2785 | B.159 | C.13 |
| 1.2786 | B.160 | C.13 |
| 1.2787 | B.161 | C.13 |
| 1.2788 | B.162 | C.13 |
| 1.2789 | B.163 | C.13 |
| 1.2790 | B.164 | C.13 |
| 1.2791 | B.165 | C.13 |
| 1.2792 | B.166 | C.13 |
| 1.2793 | B.167 | C.13 |
| 1.2794 | B.168 | C.13 |
| 1.2795 | B.169 | C.13 |
| 1.2796 | B.170 | C.13 |
| 1.2797 | B.171 | C.13 |
| 1.2798 | B.172 | C.13 |
| 1.2799 | B.173 | C.13 |
| 1.2800 | B.174 | C.13 |
| 1.2801 | B.175 | C.13 |
| 1.2802 | B.176 | C.13 |
| 1.2803 | B.177 | C.13 |
| 1.2804 | B.178 | C.13 |
| 1.2805 | B.179 | C.13 |
| 1.2806 | B.180 | C.13 |
| 1.2807 | B.181 | C.13 |
| 1.2808 | B.182 | C.13 |
| 1.2809 | B.183 | C.13 |
| 1.2810 | B.184 | C.13 |
| 1.2811 | B.185 | C.13 |
| 1.2812 | B.186 | C.13 |
| 1.2813 | B.187 | C.13 |
| 1.2814 | B.188 | C.13 |
| 1.2815 | B.189 | C.13 |
| 1.2816 | B.190 | C.13 |
| 1.2817 | B.191 | C.13 |
| 1.2818 | B.192 | C.13 |
| 1.2819 | B.193 | C.13 |
| 1.2820 | B.194 | C.13 |
| 1.2821 | B.195 | C.13 |
| 1.2822 | B.196 | C.13 |
| 1.2823 | B.197 | C.13 |
| 1.2824 | B.198 | C.13 |
| 1.2825 | B.199 | C.13 |
| 1.2826 | B.200 | C.13 |
| 1.2827 | B.201 | C.13 |
| 1.2828 | B.202 | C.13 |
| 1.2829 | B.1 | C.14 |
| 1.2830 | B.2 | C.14 |
| 1.2831 | B.3 | C.14 |
| 1.2832 | B.4 | C.14 |
| 1.2833 | B.5 | C.14 |
| 1.2834 | B.6 | C.14 |
| 1.2835 | B.7 | C.14 |
| 1.2836 | B.8 | C.14 |
| 1.2837 | B.9 | C.14 |
| 1.2838 | B.10 | C.14 |
| 1.2839 | B.11 | C.14 |
| 1.2840 | B.12 | C.14 |
| 1.2841 | B.13 | C.14 |
| 1.2842 | B.14 | C.14 |
| 1.2843 | B.15 | C.14 |
| 1.2844 | B.16 | C.14 |
| 1.2845 | B.17 | C.14 |
| 1.2846 | B.18 | C.14 |
| 1.2847 | B.19 | C.14 |
| 1.2848 | B.20 | C.14 |
| 1.2849 | B.21 | C.14 |
| 1.2850 | B.22 | C.14 |
| 1.2851 | B.23 | C.14 |
| 1.2852 | B.24 | C.14 |
| 1.2853 | B.25 | C.14 |
| 1.2854 | B.26 | C.14 |
| 1.2855 | B.27 | C.14 |
| 1.2856 | B.28 | C.14 |
| 1.2857 | B.29 | C.14 |
| 1.2858 | B.30 | C.14 |
| 1.2859 | B.31 | C.14 |
| 1.2860 | B.32 | C.14 |
| 1.2861 | B.33 | C.14 |
| 1.2862 | B.34 | C.14 |
| 1.2863 | B.35 | C.14 |
| 1.2864 | B.36 | C.14 |
| 1.2865 | B.37 | C.14 |
| 1.2866 | B.38 | C.14 |
| 1.2867 | B.39 | C.14 |
| 1.2868 | B.40 | C.14 |
| 1.2869 | B.41 | C.14 |

TABLE 1-continued (compositions 1.1 to 1.3653):

| comp. no. | herbicide B | safener C |
|---|---|---|
| 1.2870 | B.42 | C.14 |
| 1.2871 | B.43 | C.14 |
| 1.2872 | B.44 | C.14 |
| 1.2873 | B.45 | C.14 |
| 1.2874 | B.46 | C.14 |
| 1.2875 | B.47 | C.14 |
| 1.2876 | B.48 | C.14 |
| 1.2877 | B.49 | C.14 |
| 1.2878 | B.50 | C.14 |
| 1.2879 | B.51 | C.14 |
| 1.2880 | B.52 | C.14 |
| 1.2881 | B.53 | C.14 |
| 1.2882 | B.54 | C.14 |
| 1.2883 | B.55 | C.14 |
| 1.2884 | B.56 | C.14 |
| 1.2885 | B.57 | C.14 |
| 1.2886 | B.58 | C.14 |
| 1.2887 | B.59 | C.14 |
| 1.2888 | B.60 | C.14 |
| 1.2889 | B.61 | C.14 |
| 1.2890 | B.62 | C.14 |
| 1.2891 | B.63 | C.14 |
| 1.2892 | B.64 | C.14 |
| 1.2893 | B.65 | C.14 |
| 1.2894 | B.66 | C.14 |
| 1.2895 | B.67 | C.14 |
| 1.2896 | B.68 | C.14 |
| 1.2897 | B.69 | C.14 |
| 1.2898 | B.70 | C.14 |
| 1.2899 | B.71 | C.14 |
| 1.2900 | B.72 | C.14 |
| 1.2901 | B.73 | C.14 |
| 1.2902 | B.74 | C.14 |
| 1.2903 | B.75 | C.14 |
| 1.2904 | B.76 | C.14 |
| 1.2905 | B.77 | C.14 |
| 1.2906 | B.78 | C.14 |
| 1.2907 | B.79 | C.14 |
| 1.2908 | B.80 | C.14 |
| 1.2909 | B.81 | C.14 |
| 1.2910 | B.82 | C.14 |
| 1.2911 | B.83 | C.14 |
| 1.2912 | B.84 | C.14 |
| 1.2913 | B.85 | C.14 |
| 1.2914 | B.86 | C.14 |
| 1.2915 | B.87 | C.14 |
| 1.2916 | B.88 | C.14 |
| 1.2917 | B.89 | C.14 |
| 1.2918 | B.90 | C.14 |
| 1.2919 | B.91 | C.14 |
| 1.2920 | B.92 | C.14 |
| 1.2921 | B.93 | C.14 |
| 1.2922 | B.94 | C.14 |
| 1.2923 | B.95 | C.14 |
| 1.2924 | B.96 | C.14 |
| 1.2925 | B.97 | C.14 |
| 1.2926 | B.98 | C.14 |
| 1.2927 | B.99 | C.14 |
| 1.2928 | B.100 | C.14 |
| 1.2929 | B.101 | C.14 |
| 1.2930 | B.102 | C.14 |
| 1.2931 | B.103 | C.14 |
| 1.2932 | B.104 | C.14 |
| 1.2933 | B.105 | C.14 |
| 1.2934 | B.106 | C.14 |
| 1.2935 | B.107 | C.14 |
| 1.2936 | B.108 | C.14 |
| 1.2937 | B.109 | C.14 |
| 1.2938 | B.110 | C.14 |
| 1.2939 | B.111 | C.14 |
| 1.2940 | B.112 | C.14 |
| 1.2941 | B.113 | C.14 |
| 1.2942 | B.114 | C.14 |
| 1.2943 | B.115 | C.14 |
| 1.2944 | B.116 | C.14 |
| 1.2945 | B.117 | C.14 |
| 1.2946 | B.118 | C.14 |
| 1.2947 | B.119 | C.14 |
| 1.2948 | B.120 | C.14 |
| 1.2949 | B.121 | C.14 |
| 1.2950 | B.122 | C.14 |
| 1.2951 | B.123 | C.14 |
| 1.2952 | B.124 | C.14 |
| 1.2953 | B.125 | C.14 |
| 1.2954 | B.126 | C.14 |
| 1.2955 | B.127 | C.14 |
| 1.2956 | B.128 | C.14 |
| 1.2957 | B.129 | C.14 |
| 1.2958 | B.130 | C.14 |
| 1.2959 | B.131 | C.14 |
| 1.2960 | B.132 | C.14 |
| 1.2961 | B.133 | C.14 |
| 1.2962 | B.134 | C.14 |
| 1.2963 | B.135 | C.14 |
| 1.2964 | B.136 | C.14 |
| 1.2965 | B.137 | C.14 |
| 1.2966 | B.138 | C.14 |
| 1.2967 | B.139 | C.14 |
| 1.2968 | B.140 | C.14 |
| 1.2969 | B.141 | C.14 |
| 1.2970 | B.142 | C.14 |
| 1.2971 | B.143 | C.14 |
| 1.2972 | B.144 | C.14 |
| 1.2973 | B.145 | C.14 |
| 1.2974 | B.146 | C.14 |
| 1.2975 | B.147 | C.14 |
| 1.2976 | B.148 | C.14 |
| 1.2977 | B.149 | C.14 |
| 1.2978 | B.150 | C.14 |
| 1.2979 | B.151 | C.14 |
| 1.2980 | B.152 | C.14 |
| 1.2981 | B.153 | C.14 |
| 1.2982 | B.154 | C.14 |
| 1.2983 | B.155 | C.14 |
| 1.2984 | B.156 | C.14 |
| 1.2985 | B.157 | C.14 |
| 1.2986 | B.158 | C.14 |
| 1.2987 | B.159 | C.14 |
| 1.2988 | B.160 | C.14 |
| 1.2989 | B.161 | C.14 |
| 1.2990 | B.162 | C.14 |
| 1.2991 | B.163 | C.14 |
| 1.2992 | B.164 | C.14 |
| 1.2993 | B.165 | C.14 |
| 1.2994 | B.166 | C.14 |
| 1.2995 | B.167 | C.14 |
| 1.2996 | B.168 | C.14 |
| 1.2997 | B.169 | C.14 |
| 1.2998 | B.170 | C.14 |
| 1.2999 | B.171 | C.14 |
| 1.3000 | B.172 | C.14 |
| 1.3001 | B.173 | C.14 |
| 1.3002 | B.174 | C.14 |
| 1.3003 | B.175 | C.14 |
| 1.3004 | B.176 | C.14 |
| 1.3005 | B.177 | C.14 |
| 1.3006 | B.178 | C.14 |
| 1.3007 | B.179 | C.14 |
| 1.3008 | B.180 | C.14 |
| 1.3009 | B.181 | C.14 |
| 1.3010 | B.182 | C.14 |
| 1.3011 | B.183 | C.14 |
| 1.3012 | B.184 | C.14 |
| 1.3013 | B.185 | C.14 |
| 1.3014 | B.186 | C.14 |
| 1.3015 | B.187 | C.14 |
| 1.3016 | B.188 | C.14 |
| 1.3017 | B.189 | C.14 |
| 1.3018 | B.190 | C.14 |
| 1.3019 | B.191 | C.14 |
| 1.3020 | B.192 | C.14 |
| 1.3021 | B.193 | C.14 |

TABLE 1-continued (compositions 1.1 to 1.3653):

| comp. no. | herbicide B | safener C |
|---|---|---|
| 1.3022 | B.194 | C.14 |
| 1.3023 | B.195 | C.14 |
| 1.3024 | B.196 | C.14 |
| 1.3025 | B.197 | C.14 |
| 1.3026 | B.198 | C.14 |
| 1.3027 | B.199 | C.14 |
| 1.3028 | B.200 | C.14 |
| 1.3029 | B.201 | C.14 |
| 1.3030 | B.202 | C.14 |
| 1.3031 | B.1 | C.15 |
| 1.3032 | B.2 | C.15 |
| 1.3033 | B.3 | C.15 |
| 1.3034 | B.4 | C.15 |
| 1.3035 | B.5 | C.15 |
| 1.3036 | B.6 | C.15 |
| 1.3037 | B.7 | C.15 |
| 1.3038 | B.8 | C.15 |
| 1.3039 | B.9 | C.15 |
| 1.3040 | B.10 | C.15 |
| 1.3041 | B.11 | C.15 |
| 1.3042 | B.12 | C.15 |
| 1.3043 | B.13 | C.15 |
| 1.3044 | B.14 | C.15 |
| 1.3045 | B.15 | C.15 |
| 1.3046 | B.16 | C.15 |
| 1.3047 | B.17 | C.15 |
| 1.3048 | B.18 | C.15 |
| 1.3049 | B.19 | C.15 |
| 1.3050 | B.20 | C.15 |
| 1.3051 | B.21 | C.15 |
| 1.3052 | B.22 | C.15 |
| 1.3053 | B.23 | C.15 |
| 1.3054 | B.24 | C.15 |
| 1.3055 | B.25 | C.15 |
| 1.3056 | B.26 | C.15 |
| 1.3057 | B.27 | C.15 |
| 1.3058 | B.28 | C.15 |
| 1.3059 | B.29 | C.15 |
| 1.3060 | B.30 | C.15 |
| 1.3061 | B.31 | C.15 |
| 1.3062 | B.32 | C.15 |
| 1.3063 | B.33 | C.15 |
| 1.3064 | B.34 | C.15 |
| 1.3065 | B.35 | C.15 |
| 1.3066 | B.36 | C.15 |
| 1.3067 | B.37 | C.15 |
| 1.3068 | B.38 | C.15 |
| 1.3069 | B.39 | C.15 |
| 1.3070 | B.40 | C.15 |
| 1.3071 | B.41 | C.15 |
| 1.3072 | B.42 | C.15 |
| 1.3073 | B.43 | C.15 |
| 1.3074 | B.44 | C.15 |
| 1.3075 | B.45 | C.15 |
| 1.3076 | B.46 | C.15 |
| 1.3077 | B.47 | C.15 |
| 1.3078 | B.48 | C.15 |
| 1.3079 | B.49 | C.15 |
| 1.3080 | B.50 | C.15 |
| 1.3081 | B.51 | C.15 |
| 1.3082 | B.52 | C.15 |
| 1.3083 | B.53 | C.15 |
| 1.3084 | B.54 | C.15 |
| 1.3085 | B.55 | C.15 |
| 1.3086 | B.56 | C.15 |
| 1.3087 | B.57 | C.15 |
| 1.3088 | B.58 | C.15 |
| 1.3089 | B.59 | C.15 |
| 1.3090 | B.60 | C.15 |
| 1.3091 | B.61 | C.15 |
| 1.3092 | B.62 | C.15 |
| 1.3093 | B.63 | C.15 |
| 1.3094 | B.64 | C.15 |
| 1.3095 | B.65 | C.15 |
| 1.3096 | B.66 | C.15 |
| 1.3097 | B.67 | C.15 |
| 1.3098 | B.68 | C.15 |
| 1.3099 | B.69 | C.15 |
| 1.3100 | B.70 | C.15 |
| 1.3101 | B.71 | C.15 |
| 1.3102 | B.72 | C.15 |
| 1.3103 | B.73 | C.15 |
| 1.3104 | B.74 | C.15 |
| 1.3105 | B.75 | C.15 |
| 1.3106 | B.76 | C.15 |
| 1.3107 | B.77 | C.15 |
| 1.3108 | B.78 | C.15 |
| 1.3109 | B.79 | C.15 |
| 1.3110 | B.80 | C.15 |
| 1.3111 | B.81 | C.15 |
| 1.3112 | B.82 | C.15 |
| 1.3113 | B.83 | C.15 |
| 1.3114 | B.84 | C.15 |
| 1.3115 | B.85 | C.15 |
| 1.3116 | B.86 | C.15 |
| 1.3117 | B.87 | C.15 |
| 1.3118 | B.88 | C.15 |
| 1.3119 | B.89 | C.15 |
| 1.3120 | B.90 | C.15 |
| 1.3121 | B.91 | C.15 |
| 1.3122 | B.92 | C.15 |
| 1.3123 | B.93 | C.15 |
| 1.3124 | B.94 | C.15 |
| 1.3125 | B.95 | C.15 |
| 1.3126 | B.96 | C.15 |
| 1.3127 | B.97 | C.15 |
| 1.3128 | B.98 | C.15 |
| 1.3129 | B.99 | C.15 |
| 1.3130 | B.100 | C.15 |
| 1.3131 | B.101 | C.15 |
| 1.3132 | B.102 | C.15 |
| 1.3133 | B.103 | C.15 |
| 1.3134 | B.104 | C.15 |
| 1.3135 | B.105 | C.15 |
| 1.3136 | B.106 | C.15 |
| 1.3137 | B.107 | C.15 |
| 1.3138 | B.108 | C.15 |
| 1.3139 | B.109 | C.15 |
| 1.3140 | B.110 | C.15 |
| 1.3141 | B.111 | C.15 |
| 1.3142 | B.112 | C.15 |
| 1.3143 | B.113 | C.15 |
| 1.3144 | B.114 | C.15 |
| 1.3145 | B.115 | C.15 |
| 1.3146 | B.116 | C.15 |
| 1.3147 | B.117 | C.15 |
| 1.3148 | B.118 | C.15 |
| 1.3149 | B.119 | C.15 |
| 1.3150 | B.120 | C.15 |
| 1.3151 | B.121 | C.15 |
| 1.3152 | B.122 | C.15 |
| 1.3153 | B.123 | C.15 |
| 1.3154 | B.124 | C.15 |
| 1.3155 | B.125 | C.15 |
| 1.3156 | B.126 | C.15 |
| 1.3157 | B.127 | C.15 |
| 1.3158 | B.128 | C.15 |
| 1.3159 | B.129 | C.15 |
| 1.3160 | B.130 | C.15 |
| 1.3161 | B.131 | C.15 |
| 1.3162 | B.132 | C.15 |
| 1.3163 | B.133 | C.15 |
| 1.3164 | B.134 | C.15 |
| 1.3165 | B.135 | C.15 |
| 1.3166 | B.136 | C.15 |
| 1.3167 | B.137 | C.15 |
| 1.3168 | B.138 | C.15 |
| 1.3169 | B.139 | C.15 |
| 1.3170 | B.140 | C.15 |
| 1.3171 | B.141 | C.15 |
| 1.3172 | B.142 | C.15 |
| 1.3173 | B.143 | C.15 |

TABLE 1-continued (compositions 1.1 to 1.3653):

| comp. no. | herbicide B | safener C |
|---|---|---|
| 1.3174 | B.144 | C.15 |
| 1.3175 | B.145 | C.15 |
| 1.3176 | B.146 | C.15 |
| 1.3177 | B.147 | C.15 |
| 1.3178 | B.148 | C.15 |
| 1.3179 | B.149 | C.15 |
| 1.3180 | B.150 | C.15 |
| 1.3181 | B.151 | C.15 |
| 1.3182 | B.152 | C.15 |
| 1.3183 | B.153 | C.15 |
| 1.3184 | B.154 | C.15 |
| 1.3185 | B.155 | C.15 |
| 1.3186 | B.156 | C.15 |
| 1.3187 | B.157 | C.15 |
| 1.3188 | B.158 | C.15 |
| 1.3189 | B.159 | C.15 |
| 1.3190 | B.160 | C.15 |
| 1.3191 | B.161 | C.15 |
| 1.3192 | B.162 | C.15 |
| 1.3193 | B.163 | C.15 |
| 1.3194 | B.164 | C.15 |
| 1.3195 | B.165 | C.15 |
| 1.3196 | B.166 | C.15 |
| 1.3197 | B.167 | C.15 |
| 1.3198 | B.168 | C.15 |
| 1.3199 | B.169 | C.15 |
| 1.3200 | B.170 | C.15 |
| 1.3201 | B.171 | C.15 |
| 1.3202 | B.172 | C.15 |
| 1.3203 | B.173 | C.15 |
| 1.3204 | B.174 | C.15 |
| 1.3205 | B.175 | C.15 |
| 1.3206 | B.176 | C.15 |
| 1.3207 | B.177 | C.15 |
| 1.3208 | B.178 | C.15 |
| 1.3209 | B.179 | C.15 |
| 1.3210 | B.180 | C.15 |
| 1.3211 | B.181 | C.15 |
| 1.3212 | B.182 | C.15 |
| 1.3213 | B.183 | C.15 |
| 1.3214 | B.184 | C.15 |
| 1.3215 | B.185 | C.15 |
| 1.3216 | B.186 | C.15 |
| 1.3217 | B.187 | C.15 |
| 1.3218 | B.188 | C.15 |
| 1.3219 | B.189 | C.15 |
| 1.3220 | B.190 | C.15 |
| 1.3221 | B.191 | C.15 |
| 1.3222 | B.192 | C.15 |
| 1.3223 | B.193 | C.15 |
| 1.3224 | B.194 | C.15 |
| 1.3225 | B.195 | C.15 |
| 1.3226 | B.196 | C.15 |
| 1.3227 | B.197 | C.15 |
| 1.3228 | B.198 | C.15 |
| 1.3229 | B.199 | C.15 |
| 1.3230 | B.200 | C.15 |
| 1.3231 | B.201 | C.15 |
| 1.3232 | B.202 | C.15 |
| 1.3233 | B.1 | C.16 |
| 1.3234 | B.2 | C.16 |
| 1.3235 | B.3 | C.16 |
| 1.3236 | B.4 | C.16 |
| 1.3237 | B.5 | C.16 |
| 1.3238 | B.6 | C.16 |
| 1.3239 | B.7 | C.16 |
| 1.3240 | B.8 | C.16 |
| 1.3241 | B.9 | C.16 |
| 1.3242 | B.10 | C.16 |
| 1.3243 | B.11 | C.16 |
| 1.3244 | B.12 | C.16 |
| 1.3245 | B.13 | C.16 |
| 1.3246 | B.14 | C.16 |
| 1.3247 | B.15 | C.16 |
| 1.3248 | B.16 | C.16 |
| 1.3249 | B.17 | C.16 |
| 1.3250 | B.18 | C.16 |
| 1.3251 | B.19 | C.16 |
| 1.3252 | B.20 | C.16 |
| 1.3253 | B.21 | C.16 |
| 1.3254 | B.22 | C.16 |
| 1.3255 | B.23 | C.16 |
| 1.3256 | B.24 | C.16 |
| 1.3257 | B.25 | C.16 |
| 1.3258 | B.26 | C.16 |
| 1.3259 | B.27 | C.16 |
| 1.3260 | B.28 | C.16 |
| 1.3261 | B.29 | C.16 |
| 1.3262 | B.30 | C.16 |
| 1.3263 | B.31 | C.16 |
| 1.3264 | B.32 | C.16 |
| 1.3265 | B.33 | C.16 |
| 1.3266 | B.34 | C.16 |
| 1.3267 | B.35 | C.16 |
| 1.3268 | B.36 | C.16 |
| 1.3269 | B.37 | C.16 |
| 1.3270 | B.38 | C.16 |
| 1.3271 | B.39 | C.16 |
| 1.3272 | B.40 | C.16 |
| 1.3273 | B.41 | C.16 |
| 1.3274 | B.42 | C.16 |
| 1.3275 | B.43 | C.16 |
| 1.3276 | B.44 | C.16 |
| 1.3277 | B.45 | C.16 |
| 1.3278 | B.46 | C.16 |
| 1.3279 | B.47 | C.16 |
| 1.3280 | B.48 | C.16 |
| 1.3281 | B.49 | C.16 |
| 1.3282 | B.50 | C.16 |
| 1.3283 | B.51 | C.16 |
| 1.3284 | B.52 | C.16 |
| 1.3285 | B.53 | C.16 |
| 1.3286 | B.54 | C.16 |
| 1.3287 | B.55 | C.16 |
| 1.3288 | B.56 | C.16 |
| 1.3289 | B.57 | C.16 |
| 1.3290 | B.58 | C.16 |
| 1.3291 | B.59 | C.16 |
| 1.3292 | B.60 | C.16 |
| 1.3293 | B.61 | C.16 |
| 1.3294 | B.62 | C.16 |
| 1.3295 | B.63 | C.16 |
| 1.3296 | B.64 | C.16 |
| 1.3297 | B.65 | C.16 |
| 1.3298 | B.66 | C.16 |
| 1.3299 | B.67 | C.16 |
| 1.3300 | B.68 | C.16 |
| 1.3301 | B.69 | C.16 |
| 1.3302 | B.70 | C.16 |
| 1.3303 | B.71 | C.16 |
| 1.3304 | B.72 | C.16 |
| 1.3305 | B.73 | C.16 |
| 1.3306 | B.74 | C.16 |
| 1.3307 | B.75 | C.16 |
| 1.3308 | B.76 | C.16 |
| 1.3309 | B.77 | C.16 |
| 1.3310 | B.78 | C.16 |
| 1.3311 | B.79 | C.16 |
| 1.3312 | B.80 | C.16 |
| 1.3313 | B.81 | C.16 |
| 1.3314 | B.82 | C.16 |
| 1.3315 | B.83 | C.16 |
| 1.3316 | B.84 | C.16 |
| 1.3317 | B.85 | C.16 |
| 1.3318 | B.86 | C.16 |
| 1.3319 | B.87 | C.16 |
| 1.3320 | B.88 | C.16 |
| 1.3321 | B.89 | C.16 |
| 1.3322 | B.90 | C.16 |
| 1.3323 | B.91 | C.16 |
| 1.3324 | B.92 | C.16 |
| 1.3325 | B.93 | C.16 |

TABLE 1-continued (compositions 1.1 to 1.3653):

| comp. no. | herbicide B | safener C |
|---|---|---|
| 1.3326 | B.94 | C.16 |
| 1.3327 | B.95 | C.16 |
| 1.3328 | B.96 | C.16 |
| 1.3329 | B.97 | C.16 |
| 1.3330 | B.98 | C.16 |
| 1.3331 | B.99 | C.16 |
| 1.3332 | B.100 | C.16 |
| 1.3333 | B.101 | C.16 |
| 1.3334 | B.102 | C.16 |
| 1.3335 | B.103 | C.16 |
| 1.3336 | B.104 | C.16 |
| 1.3337 | B.105 | C.16 |
| 1.3338 | B.106 | C.16 |
| 1.3339 | B.107 | C.16 |
| 1.3340 | B.108 | C.16 |
| 1.3341 | B.109 | C.16 |
| 1.3342 | B.110 | C.16 |
| 1.3343 | B.111 | C.16 |
| 1.3344 | B.112 | C.16 |
| 1.3345 | B.113 | C.16 |
| 1.3346 | B.114 | C.16 |
| 1.3347 | B.115 | C.16 |
| 1.3348 | B.116 | C.16 |
| 1.3349 | B.117 | C.16 |
| 1.3350 | B.118 | C.16 |
| 1.3351 | B.119 | C.16 |
| 1.3352 | B.120 | C.16 |
| 1.3353 | B.121 | C.16 |
| 1.3354 | B.122 | C.16 |
| 1.3355 | B.123 | C.16 |
| 1.3356 | B.124 | C.16 |
| 1.3357 | B.125 | C.16 |
| 1.3358 | B.126 | C.16 |
| 1.3359 | B.127 | C.16 |
| 1.3360 | B.128 | C.16 |
| 1.3361 | B.129 | C.16 |
| 1.3362 | B.130 | C.16 |
| 1.3363 | B.131 | C.16 |
| 1.3364 | B.132 | C.16 |
| 1.3365 | B.133 | C.16 |
| 1.3366 | B.134 | C.16 |
| 1.3367 | B.135 | C.16 |
| 1.3368 | B.136 | C.16 |
| 1.3369 | B.137 | C.16 |
| 1.3370 | B.138 | C.16 |
| 1.3371 | B.139 | C.16 |
| 1.3372 | B.140 | C.16 |
| 1.3373 | B.141 | C.16 |
| 1.3374 | B.142 | C.16 |
| 1.3375 | B.143 | C.16 |
| 1.3376 | B.144 | C.16 |
| 1.3377 | B.145 | C.16 |
| 1.3378 | B.146 | C.16 |
| 1.3379 | B.147 | C.16 |
| 1.3380 | B.148 | C.16 |
| 1.3381 | B.149 | C.16 |
| 1.3382 | B.150 | C.16 |
| 1.3383 | B.151 | C.16 |
| 1.3384 | B.152 | C.16 |
| 1.3385 | B.153 | C.16 |
| 1.3386 | B.154 | C.16 |
| 1.3387 | B.155 | C.16 |
| 1.3388 | B.156 | C.16 |
| 1.3389 | B.157 | C.16 |
| 1.3390 | B.158 | C.16 |
| 1.3391 | B.159 | C.16 |
| 1.3392 | B.160 | C.16 |
| 1.3393 | B.161 | C.16 |
| 1.3394 | B.162 | C.16 |
| 1.3395 | B.163 | C.16 |
| 1.3396 | B.164 | C.16 |
| 1.3397 | B.165 | C.16 |
| 1.3398 | B.166 | C.16 |
| 1.3399 | B.167 | C.16 |
| 1.3400 | B.168 | C.16 |
| 1.3401 | B.169 | C.16 |
| 1.3402 | B.170 | C.16 |
| 1.3403 | B.171 | C.16 |
| 1.3404 | B.172 | C.16 |
| 1.3405 | B.173 | C.16 |
| 1.3406 | B.174 | C.16 |
| 1.3407 | B.175 | C.16 |
| 1.3408 | B.176 | C.16 |
| 1.3409 | B.177 | C.16 |
| 1.3410 | B.178 | C.16 |
| 1.3411 | B.179 | C.16 |
| 1.3412 | B.180 | C.16 |
| 1.3413 | B.181 | C.16 |
| 1.3414 | B.182 | C.16 |
| 1.3415 | B.183 | C.16 |
| 1.3416 | B.184 | C.16 |
| 1.3417 | B.185 | C.16 |
| 1.3418 | B.186 | C.16 |
| 1.3419 | B.187 | C.16 |
| 1.3420 | B.188 | C.16 |
| 1.3421 | B.189 | C.16 |
| 1.3422 | B.190 | C.16 |
| 1.3423 | B.191 | C.16 |
| 1.3424 | B.192 | C.16 |
| 1.3425 | B.193 | C.16 |
| 1.3426 | B.194 | C.16 |
| 1.3427 | B.195 | C.16 |
| 1.3428 | B.196 | C.16 |
| 1.3429 | B.197 | C.16 |
| 1.3430 | B.198 | C.16 |
| 1.3431 | B.199 | C.16 |
| 1.3432 | B.200 | C.16 |
| 1.3433 | B.201 | C.16 |
| 1.3434 | B.202 | C.16 |
| 1.3435 | B.1 | C.17 |
| 1.3436 | B.2 | C.17 |
| 1.3437 | B.3 | C.17 |
| 1.3438 | B.4 | C.17 |
| 1.3439 | B.5 | C.17 |
| 1.3440 | B.6 | C.17 |
| 1.3441 | B.7 | C.17 |
| 1.3442 | B.8 | C.17 |
| 1.3443 | B.9 | C.17 |
| 1.3444 | B.10 | C.17 |
| 1.3445 | B.11 | C.17 |
| 1.3446 | B.12 | C.17 |
| 1.3447 | B.13 | C.17 |
| 1.3448 | B.14 | C.17 |
| 1.3449 | B.15 | C.17 |
| 1.3450 | B.16 | C.17 |
| 1.3451 | B.17 | C.17 |
| 1.3452 | B.18 | C.17 |
| 1.3453 | B.19 | C.17 |
| 1.3454 | B.20 | C.17 |
| 1.3455 | B.21 | C.17 |
| 1.3456 | B.22 | C.17 |
| 1.3457 | B.23 | C.17 |
| 1.3458 | B.24 | C.17 |
| 1.3459 | B.25 | C.17 |
| 1.3460 | B.26 | C.17 |
| 1.3461 | B.27 | C.17 |
| 1.3462 | B.28 | C.17 |
| 1.3463 | B.29 | C.17 |
| 1.3464 | B.30 | C.17 |
| 1.3465 | B.31 | C.17 |
| 1.3466 | B.32 | C.17 |
| 1.3467 | B.33 | C.17 |
| 1.3468 | B.34 | C.17 |
| 1.3469 | B.35 | C.17 |
| 1.3470 | B.36 | C.17 |
| 1.3471 | B.37 | C.17 |
| 1.3472 | B.38 | C.17 |
| 1.3473 | B.39 | C.17 |
| 1.3474 | B.40 | C.17 |
| 1.3475 | B.41 | C.17 |
| 1.3476 | B.42 | C.17 |
| 1.3477 | B.43 | C.17 |

TABLE 1-continued (compositions 1.1 to 1.3653):

| comp. no. | herbicide B | safener C |
|---|---|---|
| 1.3478 | B.44 | C.17 |
| 1.3479 | B.45 | C.17 |
| 1.3480 | B.46 | C.17 |
| 1.3481 | B.47 | C.17 |
| 1.3482 | B.48 | C.17 |
| 1.3483 | B.49 | C.17 |
| 1.3484 | B.50 | C.17 |
| 1.3485 | B.51 | C.17 |
| 1.3486 | B.52 | C.17 |
| 1.3487 | B.53 | C.17 |
| 1.3488 | B.54 | C.17 |
| 1.3489 | B.55 | C.17 |
| 1.3490 | B.56 | C.17 |
| 1.3491 | B.57 | C.17 |
| 1.3492 | B.58 | C.17 |
| 1.3493 | B.59 | C.17 |
| 1.3494 | B.60 | C.17 |
| 1.3495 | B.61 | C.17 |
| 1.3496 | B.62 | C.17 |
| 1.3497 | B.63 | C.17 |
| 1.3498 | B.64 | C.17 |
| 1.3499 | B.65 | C.17 |
| 1.3500 | B.66 | C.17 |
| 1.3501 | B.67 | C.17 |
| 1.3502 | B.68 | C.17 |
| 1.3503 | B.69 | C.17 |
| 1.3504 | B.70 | C.17 |
| 1.3505 | B.71 | C.17 |
| 1.3506 | B.72 | C.17 |
| 1.3507 | B.73 | C.17 |
| 1.3508 | B.74 | C.17 |
| 1.3509 | B.75 | C.17 |
| 1.3510 | B.76 | C.17 |
| 1.3511 | B.77 | C.17 |
| 1.3512 | B.78 | C.17 |
| 1.3513 | B.79 | C.17 |
| 1.3514 | B.80 | C.17 |
| 1.3515 | B.81 | C.17 |
| 1.3516 | B.82 | C.17 |
| 1.3517 | B.83 | C.17 |
| 1.3518 | B.84 | C.17 |
| 1.3519 | B.85 | C.17 |
| 1.3520 | B.86 | C.17 |
| 1.3521 | B.87 | C.17 |
| 1.3522 | B.88 | C.17 |
| 1.3523 | B.89 | C.17 |
| 1.3524 | B.90 | C.17 |
| 1.3525 | B.91 | C.17 |
| 1.3526 | B.92 | C.17 |
| 1.3527 | B.93 | C.17 |
| 1.3528 | B.94 | C.17 |
| 1.3529 | B.95 | C.17 |
| 1.3530 | B.96 | C.17 |
| 1.3531 | B.97 | C.17 |
| 1.3532 | B.98 | C.17 |
| 1.3533 | B.99 | C.17 |
| 1.3534 | B.100 | C.17 |
| 1.3535 | B.101 | C.17 |
| 1.3536 | B.102 | C.17 |
| 1.3537 | B.103 | C.17 |
| 1.3538 | B.104 | C.17 |
| 1.3539 | B.105 | C.17 |
| 1.3540 | B.106 | C.17 |
| 1.3541 | B.107 | C.17 |
| 1.3542 | B.108 | C.17 |
| 1.3543 | B.109 | C.17 |
| 1.3544 | B.110 | C.17 |
| 1.3545 | B.111 | C.17 |
| 1.3546 | B.112 | C.17 |
| 1.3547 | B.113 | C.17 |
| 1.3548 | B.114 | C.17 |
| 1.3549 | B.115 | C.17 |
| 1.3550 | B.116 | C.17 |
| 1.3551 | B.117 | C.17 |
| 1.3552 | B.118 | C.17 |
| 1.3553 | B.119 | C.17 |
| 1.3554 | B.120 | C.17 |
| 1.3555 | B.121 | C.17 |
| 1.3556 | B.122 | C.17 |
| 1.3557 | B.123 | C.17 |
| 1.3558 | B.124 | C.17 |
| 1.3559 | B.125 | C.17 |
| 1.3560 | B.126 | C.17 |
| 1.3561 | B.127 | C.17 |
| 1.3562 | B.128 | C.17 |
| 1.3563 | B.129 | C.17 |
| 1.3564 | B.130 | C.17 |
| 1.3565 | B.131 | C.17 |
| 1.3566 | B.132 | C.17 |
| 1.3567 | B.133 | C.17 |
| 1.3568 | B.134 | C.17 |
| 1.3569 | B.135 | C.17 |
| 1.3570 | B.136 | C.17 |
| 1.3571 | B.137 | C.17 |
| 1.3572 | B.138 | C.17 |
| 1.3573 | B.139 | C.17 |
| 1.3574 | B.140 | C.17 |
| 1.3575 | B.141 | C.17 |
| 1.3576 | B.142 | C.17 |
| 1.3577 | B.143 | C.17 |
| 1.3578 | B.144 | C.17 |
| 1.3579 | B.145 | C.17 |
| 1.3580 | B.146 | C.17 |
| 1.3581 | B.147 | C.17 |
| 1.3582 | B.148 | C.17 |
| 1.3583 | B.149 | C.17 |
| 1.3584 | B.150 | C.17 |
| 1.3585 | B.151 | C.17 |
| 1.3586 | B.152 | C.17 |
| 1.3587 | B.153 | C.17 |
| 1.3588 | B.154 | C.17 |
| 1.3589 | B.155 | C.17 |
| 1.3590 | B.156 | C.17 |
| 1.3591 | B.157 | C.17 |
| 1.3592 | B.158 | C.17 |
| 1.3593 | B.159 | C.17 |
| 1.3594 | B.160 | C.17 |
| 1.3595 | B.161 | C.17 |
| 1.3596 | B.162 | C.17 |
| 1.3597 | B.163 | C.17 |
| 1.3598 | B.164 | C.17 |
| 1.3599 | B.165 | C.17 |
| 1.3600 | B.166 | C.17 |
| 1.3601 | B.167 | C.17 |
| 1.3602 | B.168 | C.17 |
| 1.3603 | B.169 | C.17 |
| 1.3604 | B.170 | C.17 |
| 1.3605 | B.171 | C.17 |
| 1.3606 | B.172 | C.17 |
| 1.3607 | B.173 | C.17 |
| 1.3608 | B.174 | C.17 |
| 1.3609 | B.175 | C.17 |
| 1.3610 | B.176 | C.17 |
| 1.3611 | B.177 | C.17 |
| 1.3612 | B.178 | C.17 |
| 1.3613 | B.179 | C.17 |
| 1.3614 | B.180 | C.17 |
| 1.3615 | B.181 | C.17 |
| 1.3616 | B.182 | C.17 |
| 1.3617 | B.183 | C.17 |
| 1.3618 | B.184 | C.17 |
| 1.3619 | B.185 | C.17 |
| 1.3620 | B.186 | C.17 |
| 1.3621 | B.187 | C.17 |
| 1.3622 | B.188 | C.17 |
| 1.3623 | B.189 | C.17 |
| 1.3624 | B.190 | C.17 |
| 1.3625 | B.191 | C.17 |
| 1.3626 | B.192 | C.17 |
| 1.3627 | B.193 | C.17 |
| 1.3628 | B.194 | C.17 |
| 1.3629 | B.195 | C.17 |

TABLE 1-continued (compositions 1.1 to 1.3653):

| comp. no. | herbicide B | safener C |
|---|---|---|
| 1.3630 | B.196 | C.17 |
| 1.3631 | B.197 | C.17 |
| 1.3632 | B.198 | C.17 |
| 1.3633 | B.199 | C.17 |
| 1.3634 | B.200 | C.17 |
| 1.3635 | B.201 | C.17 |
| 1.3636 | B.202 | C.17 |
| 1.3637 | — | C.1 |
| 1.3638 | — | C.2 |
| 1.3639 | — | C.3 |
| 1.3640 | — | C.4 |
| 1.3641 | — | C.5 |
| 1.3642 | — | C.6 |
| 1.3643 | — | C.7 |
| 1.3644 | — | C.8 |
| 1.3645 | — | C.9 |
| 1.3646 | — | C.10 |
| 1.3647 | — | C.11 |
| 1.3648 | — | C.12 |
| 1.3649 | — | C.13 |
| 1.3650 | — | C.14 |
| 1.3651 | — | C.15 |
| 1.3652 | — | C.16 |
| 1.3653 | — | C.17 |

Composition 1.200 for example comprises the phenylether I.a.18 and cinmethylin (B.200) (see table 1, entry 1.200; as well as table B, entry B.200).

Composition 2.200 for example comprises the phenylether I.a.19 (see the definition for compositions 2.1 to 2.3653 below) and cinmethylin (B.200) (see table 1, entry 1.200; as well as table B, entry B.200).

Also especially preferred are compositions 2.1. to 2.3653 which differ from the corresponding compositions 1.1 to 1.3653 only in that they comprise as the active compound A the phenylether of formula (I.a.19).

Also especially preferred are compositions 3.1. to 3.3653 which differ from the corresponding compositions 1.1 to 1.3653 only in that they comprise as the active compound A the phenylether of formula (I.b.18).

Also especially preferred are compositions 4.1. to 4.3635 which differ from the corresponding compositions 1.1 to 1.3635 only in that they comprise as the active compound A the pyridylether of formula (I.b.19).

Also especially preferred are compositions 5.1. to 5.3635 which differ from the corresponding compositions 1.1 to 1.3635 only in that they comprise as the active compound A the pyridylether of formula (I.l.18).

Also especially preferred are compositions 6.1. to 6.3653 which differ from the corresponding compositions 1.1 to 1.3653 only in that they comprise as the active compound A the phenylether of formula (I.l.19).

Also especially preferred are compositions 7.1. to 7.3653 which differ from the corresponding compositions 1.1 to 1.3653 only in that they comprise as the active compound A the phenylether of formula (I.n.18).

Also especially preferred are compositions 8.1. to 8.3653 which differ from the corresponding compositions 1.1 to 1.3653 only in that they comprise as the active compound A the phenylether of formula (I.n.19).

Also especially preferred are compositions 9.1. to 9.3653 which differ from the corresponding compositions 1.1 to 1.3653 only in that they comprise as the active compound A the phenylether of formula (I.p.18).

Also especially preferred are compositions 10.1. to 10.3653 which differ from the corresponding compositions 1.1 to 1.3653 only in that they comprise as the active compound A the phenylether of formula (I.p.19).

Also especially preferred are compositions 11.1. to 11.3653 which differ from the corresponding compositions 1.1 to 1.3653 only in that they comprise as the active compound A the phenylether of formula (I.q.18).

Also especially preferred are compositions 12.1. to 12.3653 which differ from the corresponding compositions 1.1 to 1.3653 only in that they comprise as the active compound A the phenylether of formula (I.q.19).

Also especially preferred are compositions 13.1. to 13.3653 which differ from the corresponding compositions 1.1 to 1.3653 only in that they comprise as the active compound A the phenylether of formula (I.s.18).

Also especially preferred are compositions 14.1. to 14.3653 which differ from the corresponding compositions 1.1 to 1.3653 only in that they comprise as the active compound A the phenylether of formula (I.s.19).

Also especially preferred are compositions 15.1. to 15.3635 which differ from the corresponding compositions 1.1 to 1.3635 only in that they comprise as the active compound A the pyridylether of formula (I.t.18).

Also especially preferred are compositions 16.1. to 16.3635 which differ from the corresponding compositions 1.1 to 1. only in that they comprise as the active compound A the pyridylether of formula (I.t.19).

Also especially preferred are compositions 17.1. to 17.3653 which differ from the corresponding compositions 1.1 to 1.3653 only in that they comprise as the active compound A the phenylether of formula (I.ac.18).

Also especially preferred are compositions 18.1. to 18.3653 which differ from the corresponding compositions 1.1 to 1.3653 only in that they comprise as the active compound A the phenylether of formula (I.ac.19).

Also especially preferred are compositions 19.1. to 19.3653 which differ from the corresponding compositions 1.1 to 1.3653 only in that they comprise as the active compound A the phenylether of formula (I.ae.18).

Also especially preferred are compositions 20.1. to 20.3653 which differ from the corresponding compositions 1.1 to 1.3653 only in that they comprise as the active compound A the phenylether of formula (I.ae.19).

Also especially preferred are compositions 21.1. to 21.3653 which differ from the corresponding compositions 1.1 to 1.3653 only in that they comprise as the active compound A the phenylether of formula (I.ag.18).

Also especially preferred are compositions 22.1. to 22.3653 which differ from the corresponding compositions 1.1 to 1.3653 only in that they comprise as the active compound A the phenylether of formula (I.ag.19).

Also especially preferred are compositions 23.1. to 23.3653 which differ from the corresponding compositions 1.1 to 1.3653 only in that they comprise as the active compound A the phenylether of formula (I.ah.18).

Also especially preferred are compositions 24.1. to 24.3653 which differ from the corresponding compositions 1.1 to 1.3653 only in that they comprise as the active compound A the phenylether of formula (I.ah.19).

The invention also relates to agrochemical compositions comprising at least an auxiliary and at least one phenylether of formula (I) according to the invention.

An agrochemical composition comprises a pesticidally effective amount of an phenylether of formula (I). The term "effective amount" denotes an amount of the composition or of the compounds I, which is sufficient for controlling unwanted plants, especially for controlling unwanted plants in crops (i.e. cultivated plants) and which does not result in a substantial damage to the treated plants. Such an amount can vary in a broad range and is dependent on various factors, such as the plants to be controlled, the treated crop or material, the climatic conditions and the specific phenylether of formula (I) used.

The phenylethers of formula (I), their N-oxides, salts or derivatives can be converted into customary types of agrochemical compositions, e. g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, 6$^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the phenylethers of formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-Soluble Concentrates (SL, LS)

10-60 wt % of an phenylether of formula (I) or a herbicidal composition comprising at least one phenylether of formula (I) (component A) and at least one further compound selected from the herbicidal compounds B (component B) and safeners C (component C) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of an phenylether of formula (I) or a herbicidal composition comprising at least one phenylether of formula (I) (component A) and at least one further compound selected from the herbicidal compounds B (component B) and safeners C (component C) according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of an phenylether of formula (I) or a herbicidal composition comprising at least one phenylether of formula (I) (component A) and at least one further compound selected from the herbicidal compounds B (component B) and safeners C (component C) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of an phenylether of formula (I) or a herbicidal composition comprising at least one phenylether of formula (I) (component A) and at least one further compound selected from the herbicidal compounds B (component B) and safeners C (component C) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of an phenylether of formula (I) or a herbicidal composition comprising at least one phenylether of formula (I) (component A) and at least one further compound selected from the herbicidal compounds B (component B) and safeners C (component C) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of an phenylether of formula (I) or a herbicidal composition comprising at least one phenylether of formula (I) (component A) and at least one further compound selected from the herbicidal compounds B (component B) and safeners C (component C) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of an phenylether of formula (I) or a herbicidal composition comprising at least one phenylether of formula (I) (component A) and at least one further compound selected from the herbicidal compounds B (component B) and safeners C (component C) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of an phenylether of formula (I) or a herbicidal composition comprising at least one phenylether of formula (I) (component A) and at least one further compound selected from the herbicidal compounds B (component B) and safeners C (component C) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of an phenylether of formula (I) or a herbicidal composition comprising at least one phenylether of formula (I) (component A) and at least one further compound selected from the herbicidal compounds B (component B) and safeners C (component C) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of an phenylether of formula (I) or a herbicidal composition comprising at least one phenylether of formula (I) (component A) and at least one further compound selected from the herbicidal compounds B (component B) and safeners C (component C) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of an phenylether of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of an phenylether of formula (I) or a herbicidal composition comprising at least one phenylether of formula (I) (component A) and at least one further compound selected from the herbicidal compounds B (component B) and safeners C (component C) according to the invention are ground finely and mixed intimately with solid carrier (e.g. finely divided kaolin) ad 100 wt %.

x) Granules (GR, FG)

0.5-30 wt % of an phenylether of formula (I) or a herbicidal composition comprising at least one phenylether of formula (I) (component A) and at least one further compound selected from the herbicidal compounds B (component B) and safeners C (component C) according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of an phenylether of formula (I) or a herbicidal composition comprising at least one phenylether of formula (I) (component A) and at least one further compound selected from the herbicidal compounds B (component B) and safeners C (component C) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions and/or herbicidal compositions comprising generally comprise between 0.01 and 95%, preferably between 0.1 and 90%, and in particular between 0.5 and 75%, by weight of the phenylethers of formula (I). The phenylethers of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying phenylethers of formula (I), agrochemical compositions and/or herbicidal compositions thereof, on to plant propagation material, especially seeds, include dressing, coating, pelleting, dusting, soaking and in-furrow application methods of the propagation material. Preferably, phenylethers of formula (I), agrochemical compositions and/or herbicidal compositions thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the phenylethers of formula (I), the agrochemical compositions and/or the herbicidal compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the phenylethers of formula (I) according to the invention, the agrochemical compositions and/or the herbicidal compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. components comprising phenylethers of formula (I) and optionally active substances from the groups B and/or C), may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g components comprising phenylethers of formula (I) and optionally active substances from the groups B and/or C), can be applied jointly (e.g. after tank mix) or consecutively.

The phenylethers of formula (I) are suitable as herbicides. They are suitable as such, as an appropriately formulated composition (agrochemical composition) or as an herbicidal composition in combination with at least one further compound selected from the herbicidal active compounds B (component B) and safeners C (component C).

The phenylethers of formula (I), or the agrochemical compositions and/or herbicidal compositions comprising the phenylethers of formula (I), control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The phenylethers of formula (I), or the agrochemical compositions and/or the herbicidal compositions comprising them, are applied to the plants mainly by spraying the leaves. Here, the application can be carried out using, for example, water as carrier by customary spraying techniques using spray liquor amounts of from about 100 to 1000 l/ha (for example from 300 to 400 l/ha). The phenylethers of formula (I), or the agrochemical compositions and/or the herbicidal compositions comprising them, may also be applied by the low-volume or the ultra-low-volume method, or in the form of microgranules.

Application of the phenylethers of formula (I), or the agrochemical compositions and/or the herbicidal compositions comprising them, can be done before, during and/or after, preferably during and/or after, the emergence of the undesirable plants.

The phenylethers of formula (I), or the agrochemical compositions and/or the herbicidal compositions comprising them, can be applied pre-, post-emergence or pre-plant, or together with the seed of a crop plant. It is also possible to apply the phenylethers of formula (I), or the agrochemical compositions and/or the herbicidal compositions comprising them, by applying seed, pretreated with the phenylethers of formula (I), or the agrochemical compositions and/or the herbicidal compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the phenylethers of formula (I), or the agrochemical compositions and/or the herbicidal compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the phenylethers of formula (I), or the agrochemical compositions and/or the herbicidal compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the phenylethers of formula (I), component B and, if appropriate, component C without formulation auxiliaries, are, depending on the kind of effect desired, from 0.001 to 2 kg per ha, preferably from 0.005 to 2 kg per ha, more preferably from 0.05 to 1.5 kg per ha and in particular from 0.1 to 1 kg per ha.

In another embodiment of the invention, the application rate of the phenylethers of formula (I), component B and, if appropriate, component C, is from 0.001 to 3 kg/ha, preferably from 0.005 to 2.5 kg/ha and in particular from 0.01 to 2 kg/ha of active substance (a.s.).

In another preferred embodiment of the invention, the rates of application of the phenylethers of formula (I) according to the present invention (total amount of phenylethers of formula (I)) are from 0.1 g/ha to 3000 g/ha, preferably 1 g/ha to 1000 g/ha, depending on the control target, the season, the target plants and the growth stage.

In another preferred embodiment of the invention, the application rates of the phenylethers of formula (I) are in the range from 0.1 g/ha to 5000 g/ha and preferably in the range from 0.5 g/ha to 2500 g/ha or from 2.5 g/ha to 2000 g/ha.

In another preferred embodiment of the invention, the application rate of the phenylethers of formula (I) is 0.1 to 1000 g/ha, preferably 0.5 to 750 g/ha, more preferably 2.5 to 500 g/ha.

The required application rates of herbicidal compounds B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safeners C are generally in the range of from 0.0005 kg/ha to 2.5 kg/ha and preferably in the range of from 0.005 kg/ha to 2 kg/ha or 0.01 kg/ha to 1.5 kg/h of a.s.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the phenylethers of formula (I), component B and, if appropriate, component C are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

In case of herbicidal compositions according to the present invention it is immaterial whether the phenylethers of formula (I), and the further component B and/or the component C are formulated and applied jointly or separately.

In the case of separate application it is of minor importance, in which order the application takes place. It is only necessary, that the phenylethers of formula (I), and the further component B and/or the component C are applied in a time frame that allows simultaneous action of the active ingredients on the plants, preferably within a time-frame of at most 14 days, in particular at most 7 days.

Depending on the application method in question, the phenylethers of formula (I), or the agrochemical compositions and/or herbicidal compositions comprising them, can additionally be employed in a further number of crop plants for eliminating undesirable plants. Examples of suitable crops are the following:

Allium cepa, Ananas comosus, Arachis hypogaea, Asparagus officinalis, Avena sativa, Beta vulgaris spec. altissima, Beta vulgaris spec. rapa, Brassica napus var. napus, Brassica napus var. napobrassica, Brassica rapa var. silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa, Phaseolus lunatus, Phaseolus vulgaris, Picea abies, Pinus spec., Pistacia vera, Pisum sativum, Prunus avium, Prunus persica, Pyrus communis, Prunus armeniaca, Prunus cerasus, Prunus dulcis and Prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera and Zea mays.

Preferred crops are Arachis hypogaea, Beta vulgaris spec. altissima, Brassica napus var. napus, Brassica oleracea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus spec., Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera and Zea mays.

Especially preferred crops are crops of cereals, corn, soybeans, rice, oilseed rape, cotton, potatoes, peanuts or permanent crops.

The phenylethers of formula (I) according to the invention, or the agrochemical compositions and/or herbicidal compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (*Coeloptera*), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the phenylethers of formula (I) according to the invention, or the agrochemical compositions and/or herbicidal compositions comprising them, are also suitable for the defoliation and/or desiccation of plant parts, for which crop plants such as cotton, potato, oilseed rape, sunflower, soybean or field beans, in particular cotton, are suitable.

In this regard, agrochemical compositions and/or herbicidal compositions for the desiccation and/or defoliation of plants, processes for preparing these agrochemical compositions and/or herbicidal compositions and methods for desiccating and/or defoliating plants using the phenylethers of formula (I) have been found.

As desiccants, the phenylethers of formula (I) are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

Moreover, it has been found, that the phenylethers of formula (I), or the agrochemical compositions and/or herbicidal compositions comprising the phenylethers of formula (I), very efficiently also control PPO resistant weeds.

Accordingly, the present invention also provides a method for controlling the growth of PPO resistant weeds, which comprises contacting such weeds, parts of it, its propagation material or its habitat with phenylethers of formula (I), wherein the PPO resistant weeds are weeds, that are resistant to PPO-inhibiting herbicides except the phenylethers of formula (I).

The invention particularly relates to a method for controlling PPO resistant weeds in crops which comprises applying phenylethers of formula (I) to crops, where said PPO herbicide resistant weeds occur or might occur.

As used herein, the terms "PPO inhibitor", "PPO inhibitor herbicide", "PPO-inhibiting herbicide", "protoporphyrinogen IX oxidase inhibitor herbicide", "protoporphyrinogen IX oxidase-inhibiting herbicide", "protoporphyrinogen oxidase inhibitor herbicide" and "protoporphyrinogen oxidase-inhibiting herbicide" are synonyms and refer to a herbicide that inhibits the enzyme protoporphyrinogen oxidase of a plant.

As used herein, the terms "PPO inhibitor herbicide resistant weed", "PPO-inhibiting herbicide resistant weed", "PPO inhibitor resistant weed", "PPO resistant weed", "protoporphyrinogen IX oxidase inhibitor herbicide resistant weed", "protoporphyrinogen IX oxidase inhibiting herbicide resistant weed", "protoporphyrinogen oxidase inhibitor herbicide resistant weed", and "protoporphyrinogen oxidase inhibiting herbicide resistant weed" are synonyms and refer to a plant that, in relation to a treatment with an appropriate or over-appropriate rate of PPO-inhibiting herbicide application, has inherited, developed or acquired an ability
(1) to survive that treatment, if it is one that is lethal to (i.e. eradicates) the wild type weed; or
(2) to exhibit significant vegetative growth or thrive after that treatment, if it is one that suppresses growth of the wild-type weed.

Effective weed control is defined as at least 70% weed suppression or eradication from the crop, or as at least 70% weed plant phototoxicity, as determined 2 weeks after treatment.

Thus, PPO resistant weeds are weeds, which are not controlled by the application of PPO inhibitors except the phenylethers of formula (I), whereas the respective sensitive biotype is controlled at that use rate.

Here, "not controlled" means that in a visual rating the weed control (herbicidal effect) is <70% of weed suppression or eradication as determined 2 weeks after treatment; and "controlled" means that in a visual rating the weed control is >90% of weed suppression or eradication as determined 2 weeks after treatment.

Preferably, PPO resistant weeds are weeds, which are not controlled (i.e. in a visual rating the weed control is <70% of weed suppression or eradication as determined 2 weeks after treatment) by the application of PPO-inhibiting herbicides except the phenylethers of formula (I).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin, fomesafen and lactofen.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from fomesafen and lactofen.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from acifluorfen, azafenidin, carfentrazone, flumiclorac, flumioxazin, fomesafen, lactofen, oxadiazon, oxyfluorfen, pyraflufen and sulfentrazone.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from acifluorfen, carfentrazone, flumiclorac, flumioxazin, fomesafen, lactofen, oxadiazon, oxyfluorfen, pyraflufen and sulfentrazone.

Also preferably, PPO resistant weeds are weeds, which are not controlled (i.e. in a visual rating the weed control is <70% of weed suppression or eradication as determined 2 weeks after treatment) by the application rate of
200 g/ha or lower,
particularly preferred 100 g/ha or lower,
especially preferred 50 to 200 g/ha,
more preferred 50 to 100 g/ha,
of PPO-inhibiting herbicides except the phenylethers of formula (I), whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
200 g/ha or lower,
particularly preferred 100 g/ha or lower,
especially preferred 50 to 200 g/ha,
more preferred 50 to 100 g/ha,
of PPO-inhibiting herbicides selected from azafenidin, fomesafen and lactofen, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
200 g/ha or lower,
particularly preferred 100 g/ha or lower,
especially preferred 50 to 200 g/ha,
more preferred 50 to 100 g/ha,
of PPO-inhibiting herbicides selected from fomesafen and lactofen, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
200 g/ha or lower,
particularly preferred 100 g/ha or lower,
especially preferred 50 to 200 g/ha,
more preferred 50 to 100 g/ha,
of PPO-inhibiting herbicides selected from acifluorfen, azafenidin, carfentrazone, flumiclorac, flumioxazin, fomesafen, lactofen, oxadiazon, oxyfluorfen, pyraflufen and sulfentrazone, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
200 g/ha or lower,
particularly preferred 100 g/ha or lower,
especially preferred 50 to 200 g/ha,
more preferred 50 to 100 g/ha,
of PPO-inhibiting herbicides selected from acifluorfen, carfentrazone, flumiclorac, flumioxazin, fomesafen, lactofen, oxadiazon, oxyfluorfen, pyraflufen and sulfentrazone, whereas the respective sensitive biotype is controlled (i.e. in a visual rating the weed control is >90% of weed suppression or eradication as determined 2 weeks after treatment) at that use rate.

Also preferably PPO-resistant weeds are those classified as being "PPO resistant" and thus listed according to Anonymous: List of herbicide resistant weeds by herbicide mode of action—weeds resistant to PPO-inhibitors (URL: www.weedscience.org/summary/MOA.aspx).

Particularly preferred the PPO resistant weeds are selected from the group consisting of *Acalypha* ssp., *Amaranthus* ssp., *Ambrosia* ssp., *Avena* ssp., *Conyza* ssp., *Descurainia* ssp., *Euphorbia* ssp. and *Senecio* ssp.;
especially preferred *Amaranthus* ssp., *Ambrosia* ssp. and *Euphorbia* ssp.;
more preferred *Amaranthus* ssp. and *Ambrosia* ssp.

Also particularly preferred the PPO resistant weeds are selected from the group consisting of Asian copperleaf (*Acalypha australis*), smooth pigweed (*Amaranthus hybridus*), Palmer amaranth (*Amaranthus Palmeri*), redroot pigweed (*Amaranthus retroflexus*), tall/common waterhemp (*Amaranthus tuberculatus, Amaranthus rudis*, or *Amaranthus tamariscinus*), common ragweed (*Ambrosia artemisiifolia*), wild oat (*Avena fatua*), fleabane (*Conyza ambigua*), marestail (*Conyza Canadensis*), flixweed (*Descurainia Sophia*), wild poinsettia (*Euphorbia heterophylla*) and eastern groundsel (*Senecio vernalis*);
especially preferred smooth pigweed (*Amaranthus hybridus*), Palmer amaranth (*Amaranthus Palmeri*), redroot pigweed (*Amaranthus retroflexus*), tall/common waterhemp (*Amaranthus tuberculatus* or *Amaranthus rudis*), common ragweed (*Ambrosia artemisiifolia*) and wild poinsettia (*Euphorbia heterophylla*);
more preferred tall/common waterhemp (*Amaranthus tuberculatus, Amaranthus rudis* or *Amaranthus tamariscinus*) and common ragweed (*Ambrosia artemisiifolia*).

Most PPO resistant weeds, in particular the biotypes of *Amaranthus tuberculatus*, are resistant due to a codon deletion on the nuclear-encoded gene PPX2L that codes for the PPO enzyme which is dual-targeted to the mitochondria and the chloroplasts. This results in a loss of the glycine amino acid in position 210 (see e.g. B. G. Young et al, Characterization of PPO-Inhibitor-Resistant Waterhemp (*Amaranthus tuberculatus*) Response to Soil-Applied PPO-Inhibiting Herbicides, Weed Science 2015, 63, 511-521).

A second type of mutation, in particular in a resistant biotype of *Ambrosia artemisiifolia*, was identified as a mutation that expressed a R98L change of the PPX2 enzyme (S. L. Rousonelos, R. M. Lee, M. S. Moreira, M. J. Van-Gessel, P. J. Tranel, Characterization of a Common Ragweed (*Ambrosia artemisiifolia*) Population Resistant to ALS- and PPO-Inhibiting Herbicides, Weed Science 60, 2012, 335-344.).

Accordingly, preferably PPO-resistant weeds are weeds whose Protox enzyme is resistant to the application of PPO inhibitors due to a mutation that is expressed as a Δ G210 or R98L change of said Protox enzyme or equivalents to the PPX2L or PPX2 respectively, in particular that is expressed as a Δ G210 or R98L change of said Protox enzyme.

The preparation of the phenyluracils of formula (I) is illustrated by examples; however, the subject matter of the present invention is not limited to the examples given.

A PREPARATION EXAMPLES

Example 1: ethyl 2-[[3-[2-chloro-5-[4-chloro-5-(difluoromethoxy)-1-methyl-pyrazol-3-yl]-4-fluoro-phenoxy]-2-pyridyl]oxy]acetate

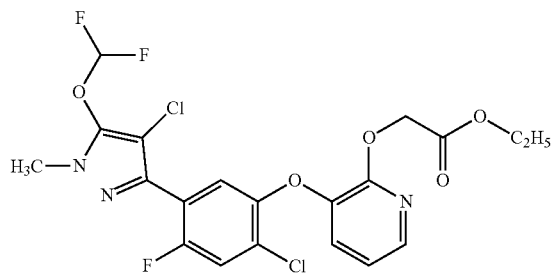 [SMILES: CCOC(=O)COc1ncccc1Oc1cc(C(=N)/C(Cl)=C(\NC)OC(F)F)c(F)cc1Cl]

Example 1 Step 1: 3-(2-chloro-4-fluoro-5-iodo-phenoxy)-2-nitro-pyridine

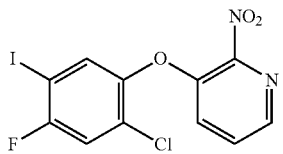 [SMILES: O=[N+]([O-])c1ncccc1Oc1cc(I)c(F)cc1Cl]

To a solution of 5.5 g (20.4 mmol) of 2-chloro-4-fluoro-5-iodophenol (CAS 148254-33-5) in 40 mL acetonitrile was added 3.4 g (24.5 mmol) potassium carbonate and 3.2 g (22.4 mmol) of 3-fluoro-2-nitropyridine (CAS 54231-35-5) at 0° C. under nitrogen atmosphere. The mixture was stirred for 1 hour at 0° C., and then for 14 hours at 80° C. The mixture was diluted with water and extracted with ethyl acetate. The combined organic layer was washed with brine, dried over anhydrous MgSO$_4$, filtered and the solvent was removed under reduced pressure. The crude product was purified by column chromatography on silica (petrol ether/ethyl acetate) to give 5.1 g (14.1 mmol, 69%) of the desired compound 1 step 1.

Example 1 Step 2: 3-(2-chloro-4-fluoro-5-iodo-phenoxy)pyridin-2-amine

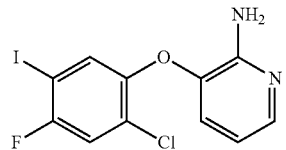 [SMILES: Nc1ncccc1Oc1cc(I)c(F)cc1Cl]

To a solution of 6.6 g (18.2 mmol) of compound 1 step 1 in 15 mL THF at 0° C. was added 5.1 g (91 mmol) iron and 50 mL aq. NH$_4$Cl dropwise. The mixture was stirred for 3 hours at 0° C., filtered and the filter cake was washed with ethyl acetate. The filtrate was diluted with water and extracted with ethyl acetate. The combined organic layer was washed with brine, dried over anhydrous MgSO$_4$, filtered and the solvent was removed under reduced pressure to give the desired compound 1 step 2 (5.6 g) which was used without further purification in the next step.

Example 1 Step 3: 3-(2-chloro-4-fluoro-5-iodo-phenoxy)pyridin-2-ol

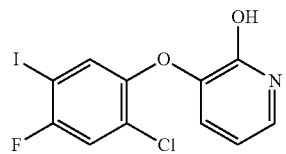 [SMILES: Oc1ncccc1Oc1cc(I)c(F)cc1Cl]

To a solution of 3.1 g (45.0 mmol) of sodium nitrite in 59 mL water at 0° C. was added 59 mL of hydrosulfuric acid dropwise. A solution of 5.5 g (15.0 mmol) of compound 1 step 2 in 59 mL acetic acid was added dropwise. The mixture was stirred for 1 hour at 0° C. The mixture was diluted with water, filtered and the filter cake was washed with ethyl acetate. the solvent was removed under reduced pressure to give the desired compound 1 step 3 (4.9 g) which was used without further purification in the next step.

Example 1 Step 4: ethyl 2-[[3-(5-bromo-2,4-di-chloro-phenoxy)-2-pyridyl]oxy]acetate

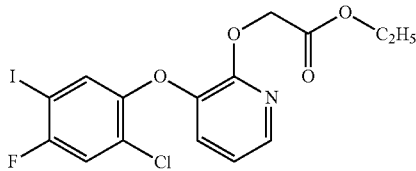 [SMILES: CCOC(=O)COc1ncccc1Oc1cc(I)c(F)cc1Cl]

To a solution of 17.5 g (47.9 mmol) of compound 1 step 3 in 200 mL 1,2-dichloroethane at 85° C. was added 1.7 mL of boron trifluoride diethyl etherate dropwise, followed by a solution of 25 g (192 mmol) of ethyl diazoacetate in 30 mL 1,2-dichloroethane dropwise. The mixture was stirred for 12 hours at 85° C. The mixture was diluted with water and extracted with ethyl acetate. The combined organic layer was washed with brine, dried over anhydrous Na$_2$SO$_4$, filtered and the solvent was removed under reduced pressure to give the desired compound 1 step 4 (16.0 g) which was used without further purification in the next step.

¹H NMR (CDCl₃, ppm): 7.94 (d, J=3.76 Hz, 1H); 7.31 (d, J=5.77 Hz, 1H); 7.13-7.24 (m, 2H); 6.93 (dd, J=7.65, 4.89 Hz, 1H); 4.95 (s, 2H); 4.17-4.30 (m, 2H); 1.27 (t, J=7.03 Hz, 3H).

Example 1 Step 5

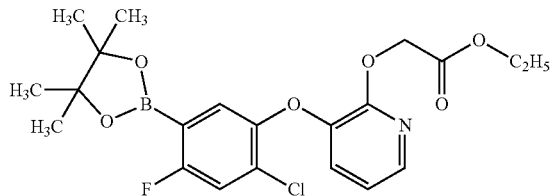 [SMILES: CCOC(=O)COc1ncccc1Oc1cc(B2OC(C)(C)C(C)(C)O2)c(F)cc1Cl]

To a solution of 2.0 g (4.4 mmol) of compound 1 step 4 in 20 mL 1,4-dioxane at 0° C. under nitrogen atmosphere was added 3.3 g (13.3 mmol) of bis(pinacolato)diboron, 26 g (26.6 mmol) of potassium acetate and 0.4 g (0.5 mmol) of 1,1'-bis(diphenylphosphino)ferrocene dichloropalladium (II). The mixture was stirred for 24 hours at 90° C. The mixture was diluted with water and extracted with ethyl acetate. The combined organic layer was washed with brine, dried over anhydrous Na₂SO₄, filtered and the solvent was removed under reduced pressure. The crude product was purified by column chromatography on silica (petrol ether/ ethyl acetate) to give 1.8 g (4.0 mmol, 90%) of the desired compound 1 step 5.

Example 1 Step 6: 4-chloro-5-(difluoromethoxy)-3-iodo-1-methyl-pyrazole

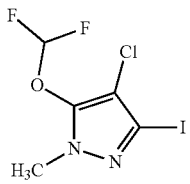

To a solution of 7.7 g (30.4 mmol) of iodine in 40 mL acetonitrile was added 3.1 g (30.4 mmol) of tert-butyl nitrite at 0° C. under argon atmosphere. The mixture was stirred for 1 hour at 0° C. and then 4.0 g of 4-chloro-5-(difluoromethoxy)-1-methyl-1H-pyrazol-3-amine (CAS 149978-51-8) was added at 0° C. The mixture was stirred for 2 hours at 25° C. The mixture was diluted with water and extracted with ethyl acetate. The combined organic layer was washed with aq. Na₂S₂O₃, dried over anhydrous MgSO₄, filtered and the solvent was removed under reduced pressure. The crude product was purified by column chromatography on silica (petrol ether/ethyl acetate) to give 4.5 g (22.8 mmol, 73%) of the desired compound 1 step 6.

Example 1 Step 7: ethyl 2-[[3-[2-chloro-5-[4-chloro-5-(difluoromethoxy)-1-methyl-pyrazol-3-yl]-4-fluoro-phenoxy]-2-pyridyl]oxy]acetate

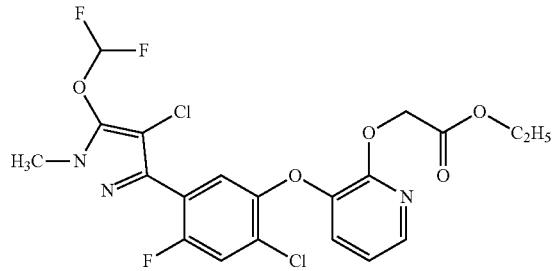 [SMILES: CCOC(=O)COc1ncccc1Oc1cc(C(=N)/C(Cl)=C(\NC)OC(F)F)c(F)cc1Cl]

To a solution of 1.3 g (4.1 mmol) of compound 1 step 6 in 20 mL 1,4-dioxane/acetonitrile/water (3:3:1) at 0° C. under nitrogen atmosphere was added 1.8 g (4.0 mmol) of compound 1.5, 1.7 g (12.2 mmol) of potassium carbonate and 0.9 g (1.2 mmol) of 1,1'-bis(diphenylphosphino)-ferrocene dichloropalladium(II). The mixture was stirred for 14 hours at 90° C. The mixture was diluted with water and extracted with ethyl acetate. The combined organic layer was washed with brine, dried over anhydrous Na₂SO₄, filtered and the solvent was removed under reduced pressure. The crude product was purified by column chromatography on silica (petrol ether/ethyl acetate) to give 1.2 g (2.4 mmol, 59%) of the desired compound 1.

¹H NMR (CDCl₃, ppm): 7.89 (d, J=4.02 Hz, 1H); 7.33 (d, J=9.03 Hz, 1H); 7.17 (dd, J=13.80, 7.03 Hz, 2H); 6.91 (br. s., 1H); 6.88 (dd, J=8.03, 2.76 Hz, 1H); 6.69 (s, 1H); 6.51 (s, 1H); 4.96 (s, 2H); 4.19 (q, J=7.03 Hz, 2H); 3.81 (s, 3H); 1.22 (t, J=7.03 Hz, 3H).

Example 2: ethyl 2-[[3-[2,4-dichloro-5-(3-oxo-5,6,7,8-tetrahydro-[1,2,4]triazolo[4,3-a]pyridin-2-yl)phenoxy]-2-pyridyl]oxy]acetate

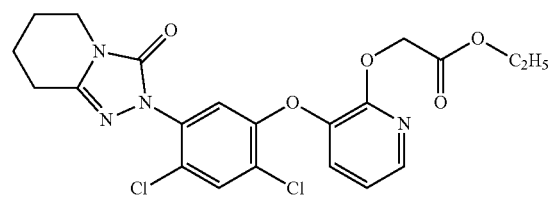 [SMILES: CCOC(=O)COc1ncccc1Oc1cc(-n2nc3n(c2=O)CCCC3)c(Cl)cc1Cl]

Example 2 Step 1: ethyl 2-[[3-[5-(2-tert-butoxycarbonylhydrazino)-2,4-dichloro-phenoxy]-2-pyridyl]oxy]acetate

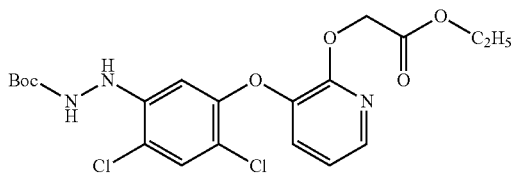 [SMILES: CCOC(=O)COc1ncccc1Oc1cc(NNC(=O)OC(C)(C)C)c(Cl)cc1Cl]

To a solution of 3.2 g (7.6 mmol) of ethyl 2-[[3-(5-bromo-2,4-dichloro-phenoxy)-2-pyridyl]oxy]acetate (synthesized from 5-bromo-2,4-dichlorophenol (CAS 183803-12-5) in analogy to compound 1 step 4 described above) and 3.0 g (CAS 870-46-2, 22.8 mmol) of tert-butyl hydrazinecarboxylate in 50 mL 1,4-dioxane was added 5.0 g (15.2 mmol) of caesium carbonate, 0.5 g (0.9 mmol) of Xantphos and 0.3 g (0.4 mmol) of tris(dibenzylideneacetone)dipalladium(0). The mixture was stirred under nitrogen atmosphere for 12 hours at 105° C. The volatiles were evaporated and the residue was purified by column chromatography on silica (petrol ether/ethyl acetate) to give 1.2 g (2.6 mmol, 34%) of the desired compound 2 step 1.

$^1$H NMR (CDCl$_3$, ppm): 7.77 (d, J=7.03 Hz, 1H); 7.15-7.27 (m, 3H); 7.07-7.13 (m, 1H); 6.24 (s, 1H); 5.40 (d, J=8.53 Hz, 1H); 3.70 (s, 3H); 1.34 (s, 9H); 1.29 (t, J=7.21 Hz, 3H).

Example 2 Step 2: ethyl 2-[[3-(2,4-dichloro-5-hydrazino-phenoxy)-2-pyridyl]oxy]acetate

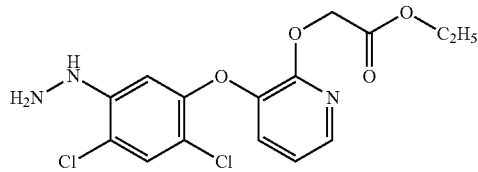 [SMILES: CCOC(=O)COc1ncccc1Oc1cc(NN)c(Cl)cc1Cl]

To a solution 1.2 g (2.5 mmol) of compound 1 step 5 in 50 mL ethyl acetate was added 30 mL of a 1 M solution of hydrochloric acid in ethyl acetate dropwise. The mixture was stirred for 12 hours at 20° C. The volatiles were evaporated to give the desired product 2 step 1 (0.9 g) which was used without further purification in the next step.

Example 2 Step 3: ethyl 2-[[3-[2,4-dichloro-5-[(2Z)-2-(2-piperidylidene)hydrazino]phenoxy]-2-pyridyl]oxy]acetate

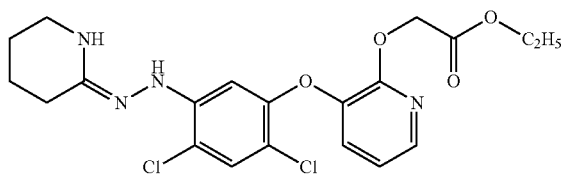 [SMILES: CCOC(=O)COc1ncccc1Oc1cc(N/N=C2/CCCCN2)c(Cl)cc1Cl]

To a solution 0.9 g (2.4 mmol) of compound 2 step 1 in 5 mL acetic acid was added a solution of 0.6 g (4.8 mmol) of 6-methoxy-2,3,4,5-tetrahydropyridine (CAS 5693-62-9) in 5 mL acetic acid. The mixture was stirred for 16 hours at 25° C. The volatiles were evaporated and the residue was purified by column chromatography on silica (dichloromethane/methanol) to give 0.7 g (1.5 mmol, 64%) of the desired compound 2 step 3.

Example 2 Step 4: ethyl 2-[[3-[2,4-dichloro-5-(3-oxo-5,6,7,8-tetrahydro-[1,2,4]triazolo[4,3-a]pyridin-2-yl)phenoxy]-2-pyridyl]oxy]acetate

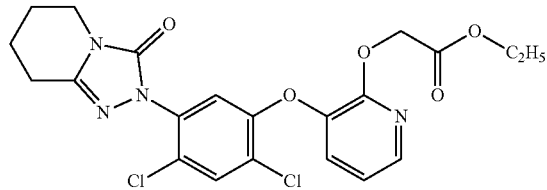 [SMILES: CCOC(=O)COc1ncccc1Oc1cc(-n2nc3n(c2=O)CCCC3)c(Cl)cc1Cl]

To a solution of 0.65 g (1.43 mmol) of compound 2 step 3 in 10 mL dichloromethane was added 1 mL (7.1 mmol) of triethylamine, 17.5 mg (0.14 mmol) of DMAP and a solution of triphosgene (0.65 g, 2.15 mmol) in 5 mL dichloromethane. The mixture was stirred for 2 hours at −10° C. The mixture was diluted with water and extracted with ethyl acetate. The combined organic layer was washed with brine, dried over anhydrous Na$_2$SO$_4$, filtered and the solvent was removed under reduced pressure. The crude product was purified by column chromatography on silica (petrol ether/ethyl acetate) to give 80 mg (0.68 mmol, 48%) of the desired compound 24.

$^1$H NMR (CDCl$_3$, ppm): 7.93 (d, J=4.03 Hz, 1H); 7.61 (s, 1H); 7.29 (d, J=4.03 Hz, 1H); 7.00 (s, 1H); 6.91 (t, J=3.80 Hz, 1H); 4.92 (s, 2H); 4.20 (t, 2H); 3.66 (t, J=5.80 Hz, 2H); 2.72 (t, J=6.20 Hz, 2H); 1.87-1.98 (m, 4H); 1.23 (t, 3H).

Example 3: ethyl 2-[[3-[2-chloro-4-fluoro-5-[(Z)-(3-oxo-5,6,7,8-tetrahydro-[1,3,4]thiadiazolo[3,4-a]pyridazin-1-ylidene)amino]phenoxy]-2-pyridyl]oxy]acetate

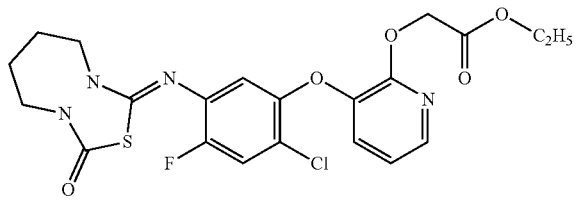 [SMILES: CCOC(=O)COc1ncccc1Oc1cc(/N=C2/NCCCCNC(=O)S2)c(F)cc1Cl]

Example 3 Step 1: ethyl 2-[[3-(2-chloro-4-fluoro-phenoxy)-2-pyridyl]oxy]acetate

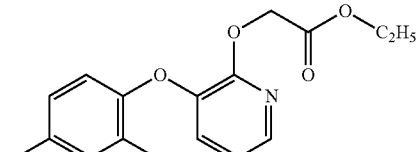

To a solution of 52.0 g (0.21 mol) of compound 3 step 3 in 400 mL 1,2-dichloroethane at 85° C. was added 5.2 mL of boron trifluoride diethyl etherate dropwise, followed by a solution of 84 g (0.74 mol) of ethyl diazoacetate in 400 mL 1,2-dichloroethane dropwise. The mixture was stirred for 12 hours at 85° C. The mixture was diluted with water and extracted with ethyl acetate. The combined organic layer was washed with brine, dried over anhydrous Na₂SO₄, filtered and the solvent was removed under reduced pressure. The crude product was purified by column chromatography on silica (petrol ether/ethyl acetate) to give 46.0 g (0.14 mol, 66%) of the desired compound 3 step 1.

¹H NMR (CDCl₃, ppm): 7.89 (dd, J=4.89, 1.38 Hz, 1H); 7.22 (dd, J=7.91, 2.64 Hz, 1H); 7.09 (dd, J=7.65, 1.38 Hz, 1H); 6.92-7.02 (m, 2H); 6.88 (dd, J=7.78, 5.02 Hz, 1H); 4.94-5.00 (m, 2H); 4.23 (q, J=7.11 Hz, 2H); 1.27 (t, J=7.15 Hz, 3H).

Example 3 Step 2: ethyl 2-[[3-(2-chloro-4-fluoro-5-nitro-phenoxy)-2-pyridyl]oxy]acetate

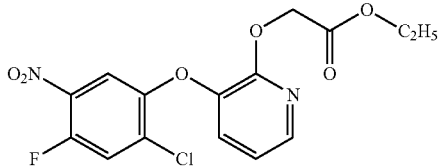 [SMILES: CCOC(=O)COc1ncccc1Oc1cc([N+](=O)[O-])c(F)cc1Cl]

To a solution of 46.0 g (0.14 mol) of ethyl 2-[[3-(2-chloro-4-fluoro-phenoxy)-2-pyridyl]oxy]acetate (synthesized from 2-chloro-4-fluorophenol (CAS 1996-41-4) in analogy to compound 1 step 4 described above) in 400 mL sulfuric acid at −10° C. was added 30 mL of a solution of fuming nitric acid and sulfuric acid (1:1). The mixture was stirred for 2 hours at −5° C. The mixture was poured into ice water, filtered and the filter cake was washed with water. The filter cake was dried to give 48.0 g of the desired compound 3 step 2 which was used without further purification in the next step.

¹H NMR (CDCl₃, ppm): 8.01-8.07 (m, 1H) 8.11 (s, 1H); 7.54 (d, J=6.62 Hz, 1H); 7.38-7.49 (m, 2H); 7.02 (dd, J=7.72, 5.07 Hz, 1H); 5.31 (s, 1H); 4.90 (s, 1H); 4.19 (q, J=7.06 Hz, 2H); 1.23 (t, J=7.06 Hz, 3H).

Example 3 Step 3: ethyl 2-[[3-(5-amino-2-chloro-4-fluoro-phenoxy)-2-pyridyl]oxy]acetate

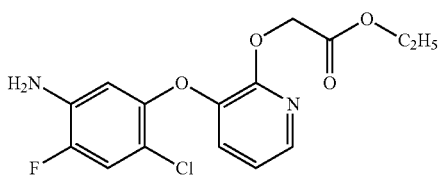

To a solution of 48.0 g (0.13 mol) of compound 3 step 1 in 500 mL acetic acid was added 36.0 g (0.65 mol) of iron at 0° C. The mixture was stirred for 12 hours at 25° C., filtered and the filter cake was washed with ethyl acetate. The filtrate was diluted with water and extracted with ethyl acetate. The combined organic layer was washed with brine, dried over anhydrous Na₂SO₄, filtered and the solvent was removed under reduced pressure to give the desired compound 3 step 3 (30.0 g) which was used without further purification in the next step.

Example 3 Step 4: ethyl 2-[[3-(2-chloro-4-fluoro-5-isothiocyanato-phenoxy)-2-pyridyl]oxy]acetate

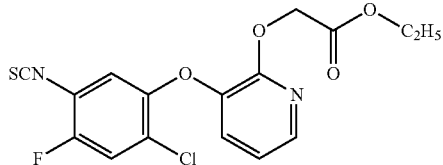 [SMILES: CCOC(=O)COc1ncccc1Oc1cc(N)c(F)cc1Cl]

To a solution of 2.0 g (6.0 mmol) of compound 3 step 2 in a 30 mL solution of chloroform and aq. NaHCO₃ (1:1) was added 1.0 g (8.8 mmol) of thiophosgene over 2 hours at 0° C. The mixture was diluted with water and extracted with ethyl acetate. The combined organic layer was washed with brine, dried over anhydrous Na₂SO₄, filtered and the solvent was removed under reduced pressure to give the desired compound 3 step 4 (1.5 g) which was used without further purification in the next step.

Example 3 Step 5: ethyl 2-[[3-[2-chloro-4-fluoro-5-(hexahydropyridazine-1-carbothioylamino)phenoxy]-2-pyridyl]oxy]acetate

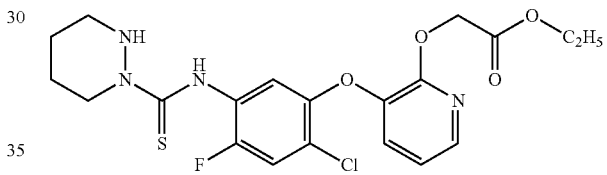

To a solution of 1.5 g (3.9 mmol) of compound 3 step 3 in 15 mL dichloromethane under nitrogen atmosphere was added 1.2 g (11.9 mmol) of triethylamine and a solution of 0.7 g (4.4 mmol) of hexahydropyridazine dihydrochloride (CAS 124072-89-5) in 5 mL dichloromethane. The mixture was stirred for 1 hour at 27° C. The volatiles were removed under vacuum. The residue was triturated with water, filtered, the filter cake was washed with water. The filtrate was extracted with ethyl acetate, washed with brine, dried over anhydrous Na₂SO₄, filtered and the solvent was removed under reduced pressure to give the desired compound 3 step 5 (1.7 g) which was used without further purification in the next step.

Example 3 Step 6: ethyl 2-[[3-[2-chloro-4-fluoro-5-[(Z)-(3-oxo-5,6,7,8-tetrahydro-[1,3,4]thiadiazolo[3,4-a]pyridazin-1-ylidene)amino]phenoxy]-2-pyridyl]oxy]acetate

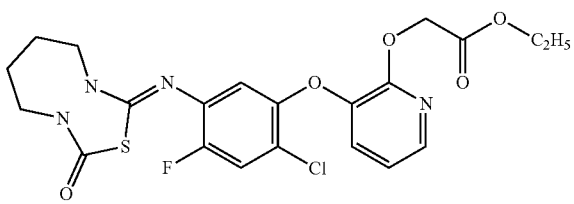 [SMILES: CCOC(=O)COc1ncccc1Oc1cc(/N=C2/NCCCCNC(=O)S2)c(F)cc1Cl]

To a solution of 20% triphosgene in toluene at −5° C. was added a solution of 2.1 g (4.6 mmol) of compound 3 step 4 in 20 mL 1,2-dichloroethane at 0° C. The mixture was stirred for 2 hours at 27° C. The mixture was diluted with water and extracted with dichloromethane. The combined organic layer was washed with brine, dried over anhydrous $Na_2SO_4$, filtered and the solvent was removed under reduced pressure to give 1.6 g of the desired compound 3 (3.3 mmol, 72%).

$^1$H NMR ($CDCl_3$, ppm): 7.88 (dd, J=4.96, 1.21 Hz, 1H); 7.24 (d, J=9.48 Hz, 1H); 7.12 (dd, J=7.83, 1.21 Hz, 1H); 6.89 (dd, J=7.83, 4.96 Hz, 1H); 6.62 (d, J=7.50 Hz, 1H); 4.96 (s, 2H); 4.22 (q, J=7.06 Hz, 2H); 3.66-3.81 (m, 4H); 1.77-1.94 (m, 4H); 1.26 (t, J=7.17 Hz, 3H).

Example 4: Ethyl 2-[[3-[5-[3,5-dimethyl-2,6-dioxo-4-(trifluoromethyl)pyrimidin-1-yl]-4-fluoro-2-nitro-phenoxy]-2-pyridyl]oxy]acetate

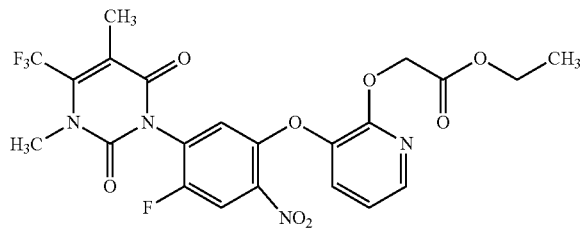

Example 4 Step 1: ethyl (Z)-3-amino-4,4,4-trifluoro-2-methyl-but-2-enoate

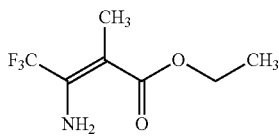

To a solution of 36.8 g (186 mmol) of (CAS 344-00-3) in 75 mL ethanol and 3.8 mL water was added 42.9 g (186 mmol) of ammonium acetate. The mixture was stirred for 16 hours at 90° C. The mixture was diluted with water and extracted with ethyl acetate. The combined organic layer was washed with brine, dried over anhydrous $MgSO_4$, filtered and the solvent was removed under reduced pressure to give the desired compound 4 step 1 (17.0 g) which was used without further purification in the next step.

$^1$H NMR ($CDCl_3$, ppm): 6.45 (br s, 2H); 4.14-4.22 (m, 2H); 1.77-1.93 (m, 3H); 1.29 (t, J=7.09 Hz, 3H).

Example 4 Step 2: 2-(dimethylamino)-5-methyl-4-(trifluoromethyl)-1,3-oxazin-6-one

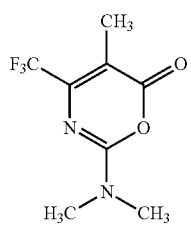

To a solution of 23.6 g (120 mmol) of compound 4 step 1 1 in 300 mL chloroform was added 19.5 g (120 mmol) of (dichloromethylene)dimethylammonium chloride (CAS 33842-02-3). The mixture was stirred for 16 hours at 25° C. The mixture was diluted with water and extracted with dichloromethane. The combined organic layer was washed with brine, dried over anhydrous $MgSO_4$, filtered and the solvent was removed under reduced pressure. The crude product was purified by column chromatography on silica (petrol ether/ethyl acetate) to give 20.0 g (90 mmol, 75%) of the desired compound 4 step 2.

$^1$H NMR ($CDCl_3$, ppm): 3.18-3.07 (m, 6H); 2.02 (q, J=2.3 Hz, 3H).

Example 4 Step 3: 3-(2,5-difluorophenyl)-5-methyl-6-(trifluoromethyl)-1H-pyrimidine-2,4-dione

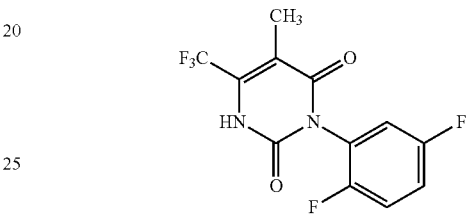

To a solution of 19.8 g (153 mmol) of 2,5-difluoroaniline (CAS 367-30-6) in 40 mL acetic acid was added 17.0 g (77.0 mmol) of compound 4 step 2. The mixture was stirred for 16 hours at 80° C. The mixture was quenched with a sat. aq. NH4Cl solution water and extracted with ethyl acetate. The combined organic layer was washed with brine, dried over anhydrous $Na_2SO_4$, filtered and the solvent was removed under reduced pressure to give the desired compound 4 step 3 (33.0 g) which was used without further purification in the next step.

Example 4 Step 4: 3-(2,5-difluorophenyl)-1,5-dimethyl-6-(trifluoromethyl)pyrimidine-2,4-dione

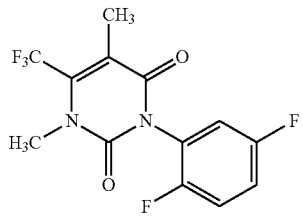 [SMILES: Cc1c(C(F)(F)F)n(C)c(=O)n(-c2cc(F)ccc2F)c1=O]

To a solution of 33.0 g (110 mmol) of compound 4 step 3 in 40 mL dimethyl formamide was added 30.4 g (220 mmol) potassium carbonate and 30.0 g (211 mmol) methyl iodide. The mixture was stirred for 16 hours at 25° C. The mixture was diluted with water and extracted with ethyl acetate. The combined organic layer was washed with brine, dried over anhydrous $Na_2SO_4$, filtered and the solvent was removed under reduced pressure. The crude product was purified by column chromatography on silica (petrol ether/ethyl acetate) to give 13.6 g (42.5 mmol, 39%) of the desired compound 4 step 4.

$^1$H NMR ($CDCl_3$, ppm): 7.24-7.12 (m, 2H); 7.00 (ddd, J=3.0, 5.5, 8.1 Hz, 1H); 3.56 (q, J=2.1 Hz, 3H); 2.25 (q, J=4.6 Hz, 3H).

137

Example 4 Step 5: 3-(2,5-difluoro-4-nitro-phenyl)-1,5-dimethyl-6-(trifluoromethyl)pyrimidine-2,4-dione

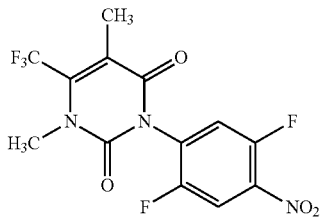 [SMILES: Cc1c(C(F)(F)F)n(C)c(=O)n(-c2cc(F)c([N+](=O)[O-])cc2F)c1=O]

To a solution of 10.7 g (33.4 mol) of compound 4 step 4 in 40 mL sulfuric acid was added a solution of 3.6 mL of fuming nitric acid in 10.7 mL sulfuric acid dropwise at −5° C. The mixture was stirred for 1.5 hours at −5° C. The mixture was diluted with ice water and extracted with ethyl acetate. The combined organic layer was washed with brine, dried over anhydrous $Na_2SO_4$, filtered and the solvent was removed under reduced pressure to give the desired compound 4 step 5 (13.7 g) which was used without further purification in the next step.

Example 4 Step 6: ethyl 2-[[3-[5-[3,5-dimethyl-2,6-dioxo-4-(trifluoromethyl)pyrimidin-1-yl]-4-fluoro-2-nitro-phenoxy]-2-pyridyl]oxy]acetate

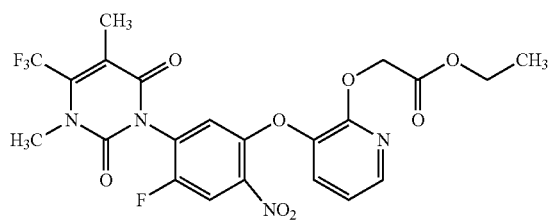 [SMILES: CCOC(=O)COc1ncccc1Oc1cc(-n2c(=O)c(C)c(C(F)(F)F)n(C)c2=O)c(F)cc1[N+](=O)[O-]]

To a solution of 13.7 g (37.5 mmol) of compound 4 step 5 in 100 mL dimethylformamide was added 1.3 g (80 mmol) of potassium carbonate and 9.7 g (49.0 mmol) of ethyl 2-((3-hydroxypyridin-2-yl)oxy)acetate (CAS 353292-81-6). The mixture was stirred for 16 hours at 25° C. The mixture was diluted with water and extracted with ethyl acetate. The combined organic layer was washed with brine, dried over anhydrous $Na_2SO_4$, filtered and the solvent was removed under reduced pressure. The crude product was purified by column chromatography on silica (petrol ether/ethyl acetate) to give 5.6 g (10.3 mmol, 28%) of the desired compound 4.

$^1$H NMR (CDCl$_3$, ppm): 7.98 (d, J=4.9 Hz, 1H); 7.87 (d, J=8.7 Hz, 1H); 7.49 (d, J=7.8 Hz, 1H); 7.10 (d, J=6.0 Hz, 1H); 6.98 (dd, J=5.0, 7.7 Hz, 1H); 4.93-4.84 (m, 2H); 4.13-4.09 (m, 2H); 3.50 (d, J=1.9 Hz, 3H); 2.19 (q, J=4.6 Hz, 3H); 2.09-2.00 (m, 3H).

138

Example 5: ethyl 2-[[3-[2-amino-5-[3,5-dimethyl-2,6-dioxo-4-(trifluoromethyl)pyrimidin-1-yl]-4-fluoro-phenoxy]-2-pyridyl]oxy]acetate

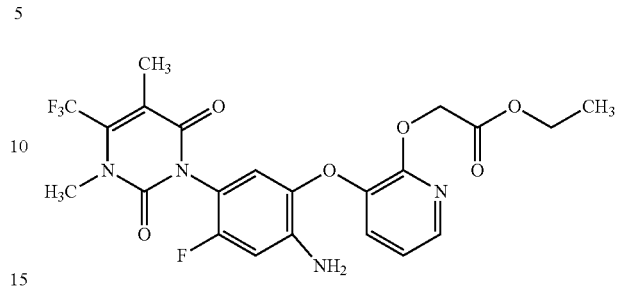

To a solution of 5.6 g (10.3 mmol) of compound 4 in 200 mL ethanol was added 10 mL water, 2.9 g (50 mmol) iron and 2.7 g (50 mmol) ammonium chloride. The mixture was stirred for 16 hours at 25° C. The mixture was diluted with water and extracted with ethyl acetate. The combined organic layer was washed with brine, dried over anhydrous $Na_2SO_4$, filtered and the solvent was removed under reduced pressure. The crude product was purified by column chromatography on silica (petrol ether/ethyl acetate) to give 4.0 g (7.8 mmol, 76%) of the desired compound 5.

$^1$H NMR (CDCl$_3$, ppm): 7.81 (d, J=4.8 Hz, 1H); 7.19 (d, J=7.9 Hz, 1H); 6.84 (dd, J=5.0, 7.8 Hz, 1H); 6.76 (d, J=6.8 Hz, 1H); 6.60 (d, J=10.9 Hz, 1H); 4.97 (s, 2H); 4.32-4.26 (m, 2H); 4.29 (q, 2H); 3.51 (d, J=1.9 Hz, 3H); 2.25-2.18 (m, 3H); 1.25 (d, J=1.4 Hz, 3H).

Example 6: ethyl 2-[[3-[2-chloro-5-[3,5-dimethyl-2,6-dioxo-4-(trifluoromethyl)pyrimidin-1-yl]-4-fluoro-phenoxy]-2-pyridyl]oxy]acetate

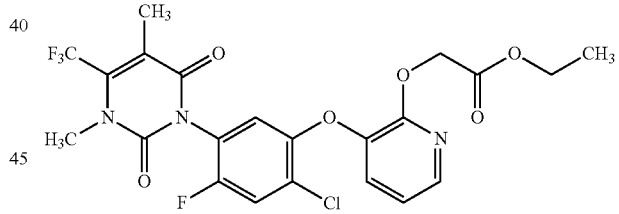

To a solution of 4.0 g (7.8 mmol) of compound 5 in 150 mL acetonitrile was added 1.6 g (15.6 mol) copper(I) chloride, 2.9 g (25 mmol) isoamyl nitrite and 2.1 g (15.6 mol) copper(II) chloride. The mixture was stirred for 1.5 hours at 25° C. The mixture was diluted with water and extracted with ethyl acetate. The combined organic layer was washed with brine, dried over anhydrous $Na_2SO_4$, filtered and the solvent was removed under reduced pressure. The crude product was purified by reverse phase preparative HPLC (acetonitrile/water containing trifluoroacetic acid) to give 2.1 g (4.0 mmol, 51%) of the desired compound 6.

$^1$H NMR (CDCl$_3$, ppm): 7.91 (dd, J=1.5, 5.0 Hz, 1H); 7.37 (d, J=8.8 Hz, 1H); 7.29 (dd, J=1.5, 7.8 Hz, 1H); 6.96-6.88 (m, 2H); 4.93 (d, J=2.5 Hz, 2H); 4.17 (q, J=7.2 Hz, 2H); 3.55-3.48 (m, 3H); 2.20 (q, J=4.6 Hz, 3H); 1.25 (t, J=7.2 Hz, 3H).

The compounds listed below in tables 1 to 9 can be prepared similarly to the example mentioned above:

TABLE 1

(I)

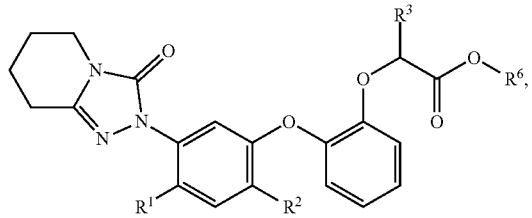

wherein $R^4$ is H, $R^5$ is $OR^6$, n is 1, Q, W and X are O, Y is $Y^{20}$, wherein $A^1$ is O and Z is Z-1 with $R^a$, $R^b$, $R^c$ and $R^d$ being H

| Example no | $R^1$ | $R^2$ | $R^3$ | $R^6$ | m/z [M + H] | $R_t$ [min] |
|---|---|---|---|---|---|---|
| 7 | Cl | Cl | $OCH_3$ | $CH_3$ | 494.0 | 1.133 |

TABLE 2

(I)

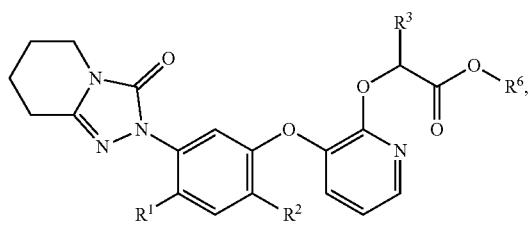

wherein $R^4$ is H, $R^5$ is $OR^6$, n is 1, Q, W and X are O, Y is $Y^{20}$, wherein $A^1$ is O and Z is Z-7 with $R^a$, $R^b$, $R^c$ being H

| Example no | $R^1$ | $R^2$ | $R^3$ | $R^6$ | m/z [M + H] | $R_t$ [min] |
|---|---|---|---|---|---|---|
| 8 | Cl | Cl | H | H | 451.0 | 0.969 |
| 9 | Cl | Cl | $CH_3$ | $C_2H_5$ | 493.0 | 1.185 |

TABLE 3

(I)

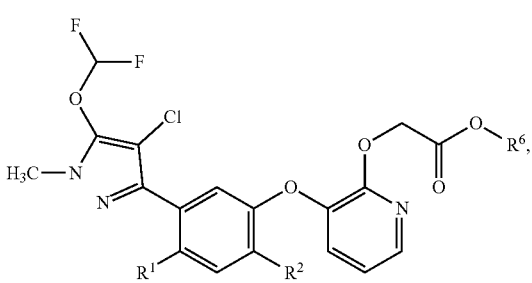

wherein $R^3$ and $R^4$ are H, $R^5$ is $OR^6$, n is 1, Q, W and X are O, Y is $Y^2$, wherein $R^{23}$ is $OCF_2H$, $R^{24}$ is $CH_3$, $R^{28}$ is Cl, and Z is Z-7 with $R^a$, $R^b$ and $R^c$ being H

| Example no | $R^1$ | $R^2$ | $R^6$ | m/z [M + H] | $R_t$ [min] |
|---|---|---|---|---|---|
| 10 | F | Cl | H | 478.0 | 1.159 |

TABLE 4

(I)

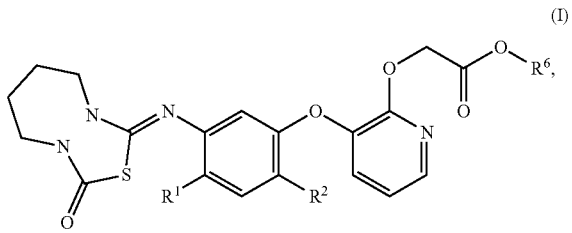

wherein $R^3$ and $R^4$ are H, $R^5$ is $OR^6$, n is 1, Q, W and X are O, Y is $Y^{37}$, wherein $A^1$ is O, $A_4$ is S, $R_{12}$ and $R^{13}$ form together —$(CH_2)_4$- and Z is Z-7 with $R^a$, $R^b$ and $R^c$ being H

| Example no | $R^1$ | $R^2$ | $R^6$ | m/z [M + H] | $R_t$ [min] |
|---|---|---|---|---|---|
| 11 | F | Cl | $C_2H_5$ | 495.0 | 1.297 |
| 12 | F | Cl | H | 467.0 | 1.120 |

TABLE 5

(I)

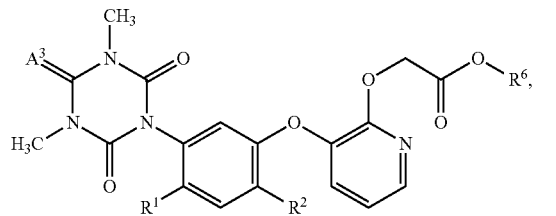

wherein $R^3$ and $R^4$ are H, $R^5$ is $OR^6$, n is 1, Q, W and X are O, Y is $Y^{67}$, wherein $A^1$ and $A^2$ are O, $R^{35}$ and $R^{36}$ are $CH_3$ and Z is Z-7 with $R^a$, $R^b$ and $R^c$ being H

| Example no | $R^1$ | $R^2$ | $R^6$ | $A^3$ | m/z [M + H] | $R_t$ [min] |
|---|---|---|---|---|---|---|
| 13 | F | Cl | $C_2H_5$ | O | 481.0 | 1.164 |
| 14 | F | Cl | $C_2H_5$ | S | 497.0 | 3.839 |

TABLE 6

(I)

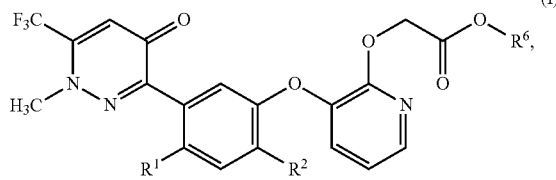

wherein $R^3$ and $R^4$ are H, $R^5$ is $OR^6$, n is 1, Q, W and X are O, Y is $Y^{65}$, wherein $A^1$ is O, $R^{12}$ is H, $R^{13}$ is $CF_3$, $R^{35}$ is $CH_3$ and Z is Z-7 with $R^a$, $R^b$ and $R^c$ being H

| Example no | $R^1$ | $R^2$ | $R^6$ | m/z [M + H] | $R_t$ [min] |
|---|---|---|---|---|---|
| 15 | F | Cl | Et | 502.0 | 1.198 |

TABLE 7

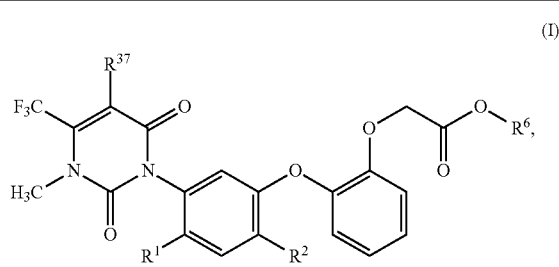

wherein $R^3$ and $R^4$ are H, $R^5$ is $OR^6$, n is 1, Q, W and X are O, Y is $Y^{55}$, wherein $A^1$ is O, $R^{12}$ is $CF_3$, $R^{35}$ is $CH_3$ and Z is Z-1 with $R^a$, $R^b$, $R^c$ and $R^d$ being H

| Example no | $R^1$ | $R^2$ | $R^6$ | $R^{37}$ | m/z [M + H] | $R_t$ [min] |
|---|---|---|---|---|---|---|
| 16 | F | Cl | $C_2H_5$ | $CH_3$ | 531.0 | 1.300 |

TABLE 8

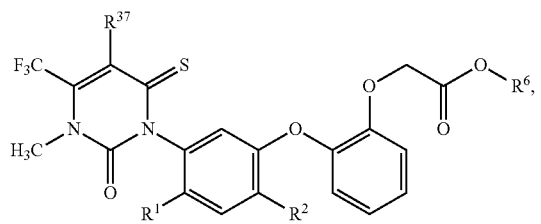

wherein $R^3$ and $R^4$ are H, $R^5$ is $OR^6$, n is 1, Q, W and X are O, Y is $Y^{66}$, wherein $A^1$ is O, $R^{12}$ is $CF_3$, $R^{35}$ is $CH_3$ and Z is Z-1 with $R^a$, $R^b$, $R^c$ and $R^d$ being H

| Example no | $R^1$ | $R^2$ | $R^6$ | $R^{13}$ | m/z [M + H] | $R_t$ [min] |
|---|---|---|---|---|---|---|
| 17 | F | Cl | $C_2H_5$ | H | 533.4 | 1.395 |

TABLE 9

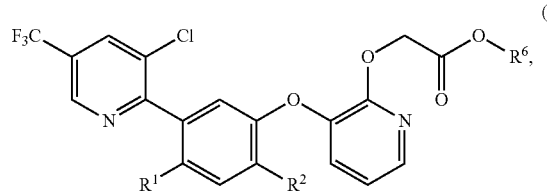

wherein $R^3$ and $R^4$ are H, $R^5$ is $OR^6$, n is 1, Q, W and X are O, Y is $Y^{42}$, wherein $R^{14}$ and $R^{15}$ are H, $R^{16}$ is $CF_3$, $R^{30}$ is Cl, and Z is Z-7 with $R^a$, $R^b$ and $R^c$ being H

| Example no | $R^1$ | $R^2$ | $R^6$ | m/z [M + H] | $R_t$ [min] |
|---|---|---|---|---|---|
| 18 | F | Cl | $C_2H_5$ | 505.0 | 1.404 |
| 19 | F | Cl | H | 476.9 | 1.231 |

B USE EXAMPLES

The herbicidal activity of the phenylethers of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles.

The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments were of the following species:

| Bayer code | Scientific name |
|---|---|
| AMARE | *Amaranthus retroflexus* |
| CHEAL | *Chenopodium album* |
| ECHCG | *Echinocloa crus-galli* |
| SETVI | *Setaria viridis* |
| ZEAMX | *Zea mays* |

At an application rate of 16 g/ha, the compounds (examples) 1, 2, 4, 7, 8, 10, 11, 12, 15, 16, 17, 18 and 19 applied by the post-emergence method, showed very good herbicidal activity against AMARE, CHEAL, ECHCG and SETVI.

At an application rate of 16 g/ha, the compound (example) 9 applied by the post-emergence method, showed very good herbicidal activity against AMARE, CHEAL and ECHCG.

At an application rate of 31 g/ha, the compound (example) 13 applied by the post-emergence method, showed very good herbicidal activity against AMARE, CHEAL and ECHCG.

TABLE 10

Comparison of the herbicidal activity of example 16 of the present invention and compound no. a-9 known from WO 02/098227 example 16

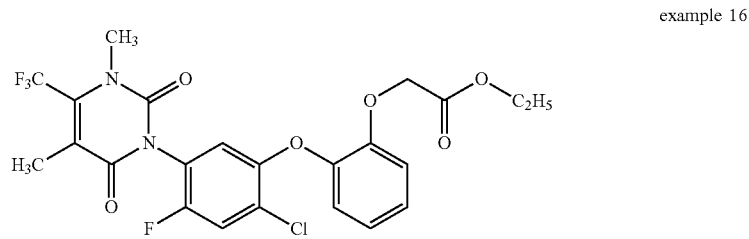

compound a-9

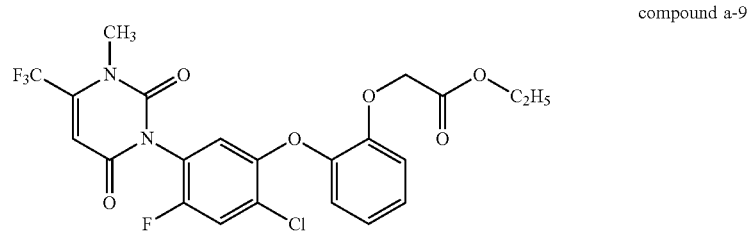

post-emergence application, control 21 days after treatment (greenhouse):

| compound | example 16 | cmpd no. a-9 (WO 02/098227) |
|---|---|---|
| application rate [g/ha] | 2 | 2 |
| | damages | |
| unwanted plants ECHCG | 100 | 98 |
| crop plants ZEAMX | 10 | 70 |

The data clearly demonstrate the better herbicidal activity and the superior crop compatibility of the inventive compounds of formula (I) of the present invention over the compounds known from the prior art.

The replacement of the hydrogen by a methyl group within the uracil moiety leads not only to a better herbicidal activity, but also to a much better crop compatibility as achieved by the compound known from WO 02/098227.

TABLE 11

Comparison of the herbicidal activity of example 17 of the present invention and compound no. a-9 known from WO 02/098227

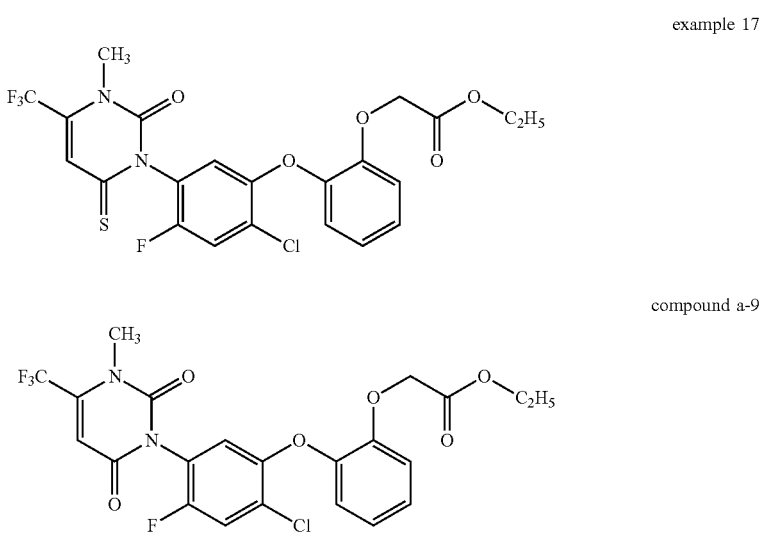

TABLE 11-continued pre-emergence application, control 21 days after treatment (greenhouse):

| compound | example 17 | cmpd no. a-9 (WO 02/098227) |
|---|---|---|
| application rate [g/ha] | 32 | 32 |
| | damages | |
| unwanted plants AMARE | 100 | 100 |
| crop plants ZEAMX | 0 | 40 |

The data clearly demonstrate the superior crop compatibility of the inventive compounds of formula (I) of the present invention over the compounds known from the prior art.

The replacement of the uracil ring by an thiouracil ring leads not only to the same herbicidal activity, but also to a much better crop compatibility as achieved by the compound known from WO 02/098227.

The invention claimed is:

1. A phenylether of formula (I)

wherein the variables have the following meanings:
$R^1$ is H or halogen;
$R^2$ is halogen;
$R^3$ is H;
$R^4$ is H;
$R^5$ is $OR^6$, wherein
$R^6$ is hydrogen or $C_1$-$C_6$-alkyl;
n is 1;
Q is O;
W is O;
X is O;
Y is a heterocycle selected from the group consisting of Y2, Y13, Y20, Y31, Y37, Y38, Y39, Y67 and Y69 wherein
A$^1$, A$^3$ are oxygen or sulfur;
A$^2$ is oxygen;
A$^4$ is sulphur;
R$^{19}$, R$^{23}$, R$^{24}$ are hydrogen, C$_1$-C$_6$-alkyl, C$_1$-C$_6$-haloalkyl or C$_1$-C$_6$-haloalkoxy;
R$^{21}$ and R$^{22}$ together with the atoms to which they are attached, form a five- to six-membered cycle, which is saturated or partial unsaturated, and which for its part may be partially halogenated or substituted by two C1-C6-alkylradicals;
R$^{26}$ and R$^{27}$ are C$_1$-C$_6$-alkyl;
R$^{28}$ is halogen or C$_1$-C$_6$-alkyl;
R$^{32}$ and R$^{33}$ are hydrogen;
R$^{35}$ and R$^{36}$ are C$_1$-C$_6$-alkyl;
Z is Z-1 or Z-7,

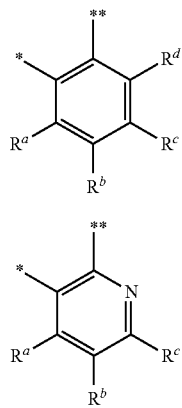

wherein
* denotes the point of attachment of Z to X;
** denotes the point of attachment of Z to Q; and
R$^a$, R$^b$, R$^c$ and R$^d$ are H;
including their agriculturally acceptable salts or amides, esters and thioesters.

2. The phenylether of formula (I) according to claim 1 wherein R$^1$ is H or F, and R$^2$ is F or Cl.

3. The phenylether of formula (I) according to claim 1 wherein Y is selected from the group consisting of Y$^2$, Y$^{13}$, Y$^{20}$ and Y$^{67}$.

4. The phenylether of formula (I) according to claim 1 wherein Y is selected from the group consisting of Y$^2$, Y$^{20}$, Y$^{37}$ and Y$^{67}$.

5. The phenylether of formula (I) according to claim 1 wherein Y is Y$^{67}$.

6. A herbicidal composition comprising an herbicidally effective amount of at least one phenylether of formula (I) as claimed in claim 1 and at least one inert liquid and/or solid carrier.

7. The herbicidal composition according to claim 6, further comprising at least one surface-active substance.

8. A process for the preparation of an herbicidal effective composition, which comprises mixing an herbicidally effective amount of at least one phenylether of formula (I) as claimed in claim 1 and at least one inert liquid and/or solid carrier.

9. The process according to claim 8 further comprising mixing at least one surface-active substance with the herbicidally effective amount of the at least one phenylether of formula (I) and the at least one inert liquid and/or solid carrier.

10. A method of controlling weeds, comprising applying an herbicidally effective amount of at least one phenylether of formula (I) as claimed in claim 1 to plant propagation material or to said weeds, or their environment.

* * * * *